US010533159B2

(12) United States Patent
Ly et al.

(10) Patent No.: US 10,533,159 B2
(45) Date of Patent: Jan. 14, 2020

(54) PICHINDE VIRUS REVERSE GENETICS SYSTEMS AND METHODS OF USE

(71) Applicant: REGENTS OF THE UNIVERSITY OF MINNESOTA, Minneapolis, MN (US)

(72) Inventors: Hinh Ly, Woodbury, MN (US); Yuying Liang, Woodbury, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 15/513,045

(22) PCT Filed: Sep. 22, 2015

(86) PCT No.: PCT/US2015/051337
§ 371 (c)(1),
(2) Date: Mar. 21, 2017

(87) PCT Pub. No.: WO2016/048949
PCT Pub. Date: Mar. 31, 2016

(65) Prior Publication Data
US 2017/0292119 A1 Oct. 12, 2017

Related U.S. Application Data

(60) Provisional application No. 62/053,443, filed on Sep. 22, 2014.

(51) Int. Cl.
*C12N 7/00* (2006.01)
*C12N 15/86* (2006.01)
*A61K 39/00* (2006.01)

(52) U.S. Cl.
CPC .............. *C12N 7/00* (2013.01); *C12N 15/86* (2013.01); *A61K 2039/5256* (2013.01); *A61K 2039/70* (2013.01); *C12N 2760/10043* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 8,592,205 | B2 | 11/2013 | Pinschewer |
| 2003/0148325 | A1 | 8/2003 | Sanchez |
| 2010/0297172 | A1 | 11/2010 | Pinschewer |
| 2011/0123567 | A1 | 5/2011 | Bird |
| 2012/0219576 | A1 | 8/2012 | Branco |
| 2017/0292119 | A1 | 10/2017 | Ly |

FOREIGN PATENT DOCUMENTS

| | | | |
|---|---|---|---|
| WO | WO 2009083210 A1 | 7/2009 | |
| WO | WO 2011141451 A1 | 11/2011 | |
| WO | WO 2011156273 A1 | 12/2011 | |

OTHER PUBLICATIONS

Auperin et al. "Sequencing Studies of Pichinde Arenavirus S RNA Indicate a Novel Coding Strategy, an Ambisense Viral S RNA" 52(3) Journal of Virology 897-904 (1984).*
Lan et al. "Development of Infectious Clones for Virulent and Avirulent Pichinde Viruses: a Model Virus to Study Arenavirus-Induced Hemorrhagic Fevers" 83(13) Journal of Virology 6357-6362 (2009).*
International Patent Application No. PCT/US2015/051337, filed Sep. 22, 2015 International Search Report/Written Opinion; dated Dec. 2, 2015; 15 pages.
International Patent Application No. PCT/US2015/051337, filed Sep. 22, 2015; International Search Report; dated Apr. 6, 2017; 8 pages.
Aronson, "Pathological and virological features of arenavirus disease in guinea pigs. Comparison of two Pichinde virus strains" 1994 *Am J Pathol.*, 145:228-235.
Auperin, "Sequencing Studies of Pichinde Arenavirus S RNA Indicate a Novel Coding Strategy, an Ambisense Viral S RNA" Dec. 1984 *J Virol.*, 52(3):897-904.
Buchmeier, "Serological evidence of infection by Pichinde virus among laboratory workers" 1974 *Infect Immun.*, 9(5):821-823.
Buchmeier, "Arenaviridae: the viruses and their replication" , in Knipe DM, Howley PM (ed), *Fields Virology, 5th ed.*; Lippincott Williams & Wilkins, Philadelphia, PA; 2007. Cover page, publisher's page, and pp. 1791-1827.
Burri, "Envelope glycoprotein of arenaviruses" 2012 *Viruses,* 4:2162-2181.
Carnec, "Lassa virus nucleoprotein mutants generated by reverse genetics induce a robust type I interferon response in human dendritic cells and macrophages" Nov. 2011 *J Virol.*, 85:12093-12097.
Carter, "Characterization of Nucleic Acid of Pichinde Virus" Jan. 1973 Journal of Virology, 11(1):61-68.
CDC, Prevention Lymphocytic Choriomeningitis (LCM), May 2014. Online: https://www.cdc.gov/vhf/lcm/prevention/index.html.

(Continued)

*Primary Examiner* — Nancy J Leith
(74) *Attorney, Agent, or Firm* — Mueting, Raasch & Gebhardt, P.A.

(57) ABSTRACT

Provided herein are genetically engineered Pichinde viruses that include three ambisense genomic segments. The first genomic segment includes a coding region encoding a Z protein and a coding region encoding a L RdRp protein. The second genomic segment includes a coding region encoding a nucleoprotein (NP) and the third genomic segment includes a coding region encoding a glycoprotein. Each of the second and third genomic segments optionally include an additional coding region that may encode an antigen or a detectable marker. Also provided herein is a reverse genetics system for making a genetically engineered Pichinde virus, and a collection of vectors that can be used to produce a genetically engineered Pichinde virus. Further provided are methods for using a reverse genetics system, and methods for producing an immune response in a subject.

60 Claims, 30 Drawing Sheets
Specification includes a Sequence Listing.

(56) References Cited

OTHER PUBLICATIONS

Dhanwani, "A Novel Live Pichinde Virus-Based Vaccine Vector Induces Enhanced Humoral and Cellular Immunity after a Booster Dose" Mar. 2016 *Amer Soc Microbiol.*, 90(5):2551-2560.
Emonet, "Arenavirus Reverse Genetics: New Approaches for the Investigation of Arenavirus Biology and Development of Antiviral Strategies" Mar. 2011 *Virol.*, 411(2):416-425.
Emonet, "Generation of recombinant lymphocytic choriomeningitis viruses with trisegmented genomes stably expressing two additional genes of interest" 2009 *Proc Natl Acad Sci USA*, 106:3473-3478.
Fehling, "Multifunctional nature of the arenavirus RING finger protein Z" Nov. 2012 *Viruses*, 4:2973-3011.
Fiore, "Seasonal influenza vaccines" 2009 *Curr Top Microbiol Immunol.*, 333:43-82.
Flatz, "Development of replication-defective lymphocytic choriomeningitis virus vectors for the induction of potent CD8+ T cell immunity" Mar. 2010 *Nat Med.*, 16:339-345.
Hastie, "Structure of the Lassa virus nucleoprotein reveals a dsRNA-speci:fic 3' to 5' exonuclease activity essential for immune suppression" 2011 *Proc Natl Acad Sci USA*, 108:2396-2401.
Hastie, "Structural Basis for the dsRNA Specificity of the Lassa Virus NP Exonuclease" Aug. 2012 *PLoS One*, 7:e44211.
Huang, "In vitro and in vivo characterizations of the Pichinde viral NP exoribonuclease function" Jul. 2015 *J Virol.*, 6395-6407.
Jang, "Options and obstacles for designing a universal influenza vaccine" Aug. 2014 *Viruses*, 6:3159-3180.
Jiang, "Structures of arenaviral nucleoproteins with triphosphate dsRNA reveal a unique mechanism of immune suppression" Jun. 2013 *J Biol Chem.*, 288:16949-16959.
Krammer, "Hemagglutinin Stalk-Reactive Antibodies Are Boosted following Sequential Infection with Seasonal and Pandemic H1N1 Influenza Virus in Mice" 2012 *J Virol.*, 86:10302-10307.
Kumar, "Characterization of virulence-associated determinants in the envelope glycoprotein of Pichinde virus" Nov. 2012 *Virology* 433:97-103.
Lan, "Development of infectious clones for virulent and avirulent pichinde viruses: a model virus to study arenavirus-induced hemorrhagic fevers" 2009 *J Virol.*, 83:6357-6362.
Lan, "Genome Comparison of Virulent and Avirulent Strains of the Arenavirus Pichinde" 2008 *Arch Virol.*, 153(7): 1241-1250.
Larkin, "ClustalW and ClustalX version 2" Nov. 2007 *Bioinformatics* 23(21):2947-2948.
Lee, "NP and L proteins of lymphocytic choriomeningitis virus (LCMV) are sufficient for efficient transcription and replication of LCMV genomic RNA analogs" Apr. 2000 *J Virol.*, 74:3470-3477.
Liang, "Molecular determinants of Pichinde virus infection of guinea pigs—a small animal model system for arenaviral hemorrhagic fevers" Mar. 2009 *Ann NY Acad Sci.*, 1171 Suppl 1:E65-74.
Margine, "H3N2 influenza virus infection induces broadly reactive hemagglutinin stalk antibodies in humans and mice" Apr. 2013 *J Virol.*, 87:4728-4737.
Martinez-Sobrido, "Inhibition of the type I interferon response by the nucleoprotein of the prototypic arenavirus lymphocytic choriomeningitis virus" Sep. 2006 *J Virol.*, 80:9192-9199.
Martinez-Sobrido, "Differential inhibition of type I interferon induction by arenavirus nucleoproteins" Nov. 2007 *J Virol.*, 81: 12696-12703.
Matsuoka, "The mouse model for influenza" 2009 *Curr Protoc Microbiol* Chapter 15:Unit 15G 13.
McLay, "Comparative analysis of disease pathogenesis and molecular mechanisms of New World and Old World arenavirus infections" Jan. 2014 *J Gen Virol.*, 95:1-15.
McLay, "Targeting virulence mechanisms for the prevention and therapy of arenaviral hemorrhagic fever" 2013 *Antiviral Res.*, 97:81-92.
McLay, "Identification of virulence determinants within the L genomic segment of the pichinde arenavirus" 2013 *J Virol.*, 87:6635-6643.
Miller, "1976 and 2009 H1N1 influenza virus vaccines boost anti-hemagglutinin stalk antibodies in humans" 2013 *J Infect Dis.*, 207:98-105.
Miller, "Neutralizing antibodies against previously encountered influenza virus strains increase over time: a longitudinal analysis" Aug. 2013 *Sci Transl Med.*, 5:198ra107.
National Center for Biotechnology Information, National Library of Medicine, National Institutes of Health, GenBank Accession No. ABU39910.1, "Z protein [Pichinde mammarenavirus]," [online]. Bethesda, MD [retrieved on Jun. 21, 2018]. Retrieved from the Internet: https://www.ncbi.nlm.nih.gov/protein/ABU39910.1; 1 pg.
National Center for Biotechnology Information, National Library of Medicine, National Institutes of Health, GenBank Accession No. ABU39911.1, "L polymerase [Pichinde mammarenavirus]," [online]. Bethesda, MD [retrieved on Jun. 21, 2018]. Retrieved from the Internet: https://www.ncbi.nlm.nih.gov/protein/ ABU39911.1; 2 pgs.
National Center for Biotechnology Information, National Library of Medicine, National Institutes of Health, GenBank Accession No. ABU39909.1, "nucleoprotein [Pichinde mammarenavirus]," [online]. Bethesda, MD [retrieved on Jun. 21, 2018]. Retrieved from the Internet: https://www.ncbi.nlm.nih.gov/protein/ ABU39909.1; 1 pg.
National Center for Biotechnology Information, National Library of Medicine, National Institutes of Health, GenBank Accession No. ABU39908.1, "glycoprotein precursor [Pichinde mammarenavirus]," [online]. Bethesda, MD [retrieved on Jun. 21, 2018]. Retrieved from the Internet: https://www.ncbi.nlm.nih.gov/protein/ ABU39908.1; 1 pg.
National Center for Biotechnology Information, National Library of Medicine, National Institutes of Health, GenBank Accession No. EF529746.1, "Pichinde virus strain Munchique CoAn4763 isolate P18 segment S, complete sequence," [online]. Bethesda, MD [retrieved on Jun. 21, 2018]. Retrieved from the Internet: https://www.ncbi.nlm.nih.gov/protein/EF529746.1; 3 pgs.
National Center for Biotechnology Information, National Library of Medicine, National Institutes of Health, GenBank Accession No. EF529747.1, "Pichinde virus strain Munchique CoAn4763 isolate P18 segment L, complete sequence," [online]. Bethesda, MD [retrieved on Jun. 21, 2018]. Retrieved from the Internet: https://www.ncbi.nlm.nih.gov/protein/EF529747.1; 2 pgs.
NG, "Networking at the level of host immunity: immune cell interactions during persistent viral infections" Jun. 2013 *Cell Host Microbe*, 13:652-664.
Ortiz-Riano, "Arenavirus reverse genetics for vaccine development" 2013 J Gen Virol., 94:1175-1188.
Park, "Newcastle disease virus (NDV)-based assay demonstrates interferon-antagonist activity for the NDV V protein and the Nipah virus V, W, and C proteins" Jan. 2003 *J Virol.*, 77:1501-1511.
Pica, "Toward a universal influenza virus vaccine: prospects and challenges" Mar. 2013 *Annu Rev Med.*, 64:189-202.
Pinschewer, "Role of the virus nucleoprotein in the regulation of lymphocytic choriomeningitis virus transcription and RNA replication" 2003 *J Virol.*, 77:3882-3887.
Pinschewer, "Kinetics of protective antibodies are determined by the viral surface antigen" Oct. 2004 *J Clin Invest.*, 114:988-993.
Popkin, "Expanded potential for recombinant trisegmented lymphocytic choriomeningitis viruses: protein production, antibody production, and in vivo assessment of biological function of genes of interest" 2011 J Virol., 85:7928-7932.
Qi, "Cap binding and immune evasion revealed by Lassa nucleoprotein structure" May 2010 Nature 468:779-783.
Ramos, "Structural Proteins of Pichinde Virus" Oct. 1972 *J Virol.*, 10(4):661-667.
Reber, "Immunological assessment of influenza vaccines and immune correlates of protection" May 2013 *Expert Rev Vaccines*, 12:519-536.
Robert-Guroff, "Replicating and non-replicating viral vectors for vaccine development" Dec. 2007 *Curr Opin Biotechnol.*, 18:546-556.
Rollier, "Viral vectors as vaccine platforms: deployment in sight" Jun. 2011 *Curr Opin Immunol* 23(3):377-382.
Rosenthal, "Studies concerning the relationship of Pichinde virus-induced natural killer cells and cytotoxic T lymphocytes" 1986 *Med Microbiol Immunol* 175:133-136.

(56) References Cited

OTHER PUBLICATIONS

Salvato, "The primary structure of the lymphocytic choriomeningitis virus L gene encodes a putative RNA polymerase" 1989 *Virology* 169:377-384.
Sambrook, *Molecular Cloning: A Laboratory Manual*, Cold Spring Harbor Laboratory Press: Cold Spring Harbor, NY; 1989. Title page, publisher's page, and table of contents; 30 pgs.
Shaw, "New technologies for new influenza vaccines" Jul. 2012 *Vaccine*, 30(33):4927-4933.
Small, "Viruses—from pathogens to vaccine carriers" Oct. 2011 *Curr Opin Virol* 1:241-245.
Tatusova, "Blast 2 Sequences, a new tool for comparing protein and nucleotide sequences" 1999 *FEMS Microbiol Lett,* 174, 247-250 (1999.
Tober, "VSV-GP: a potent viral vaccine vector that boosts the immune response upon repeated applications" May 2014 *J Virol.,* 88:4897-4907.
Trapido, "Pichinde virus, a new virus of the Tacaribe group from Colombia" 1971 *Am J Trop Med Hyg.,* 20:631-641.
Wang, "Biological roles and functional mechanisms of arenavirus z protein in viral replication" Sep. 2012 *J Virol* 86:9794-9801.
Wei, "Induction of broadly neutralizing H1N1 influenza antibodies by vaccination" Aug. 2010 *Science* 329:1060-1064.
Wei, "Elicitation of broadly neutralizing influenza antibodies in animals with previous influenza exposure" 2012 *Sci Transl Med.,* 4:147ra114.
World Health Organization (WHO) Network WGIS. "Manual for the laboratory diagnosis and virological surveillance of influenza" 2011.
Wrammert, "Broadly cross-reactive antibodies dominate the human B cell response against 2009 pandemic H1N1 influenza virus infection" Jan. 2011 *J Exp Med.,* 208:181-193.
Xing, "The Z Proteins of Pathogenic but Not Nonpathogenic Arenaviruses Inhibit RIG-i-Like Receptor-Dependent Interferon Production" Mar. 2015 *J Virol.,* 89:2944-2955.
Zhou, "Role of lymphocytic choriomeningitis virus (LCMV) in understanding viral immunology: past, present and future" Nov. 2012 Viruses, 4:2650-2669.

\* cited by examiner

| HAI titer | Route | 0 | 14 | 23 |
|---|---|---|---|---|
| Formalin-inactivated PR8 (50ug) | IN | <10 | 40, 80, 80 | 40, 640, 80 |
| rP18tri-HA | IN | <10 | 20, 40, 80 | 40, 80, 160 |
| rP18tri-HA | IM | <10 | 80, 80, 160 | 80, 160, 320 |
| rP18tri-HA | IP | <10 | 40, 40, 80 | 80, 80, 320 |

HA rP18tri-GFP/GFP      rP18tri-HA/NP      rP18tri-NP/HA

| NP+CD8/<br>NP+CD44 | 7 d post-prime | | 7 d post-boost | |
|---|---|---|---|---|
| | Blood | Spleen | Blood | Spleen |
| rP18triGFP/NP<br>IP | 2.98/<br>2.98 | 2.63/<br>2.58 | 5.55/<br>4.48 | 6.48/<br>6.08 |

```
                         SEQUENCE LISTING

<160> NUMBER OF SEQ ID NOS: 14

<210> SEQ ID NO 1
    <211> LENGTH: 95
    <212> TYPE: PRT
    <213> ORGANISM: Pichinde mammarenavirus

<400> SEQUENCE: 1

Met Gly Leu Arg Tyr Ser Lys Glu Val Arg Lys Arg His Gly Asp Glu
    1               5                   10                  15

Asp Val Val Gly Arg Val Pro Met Thr Leu Asn Leu Pro Gln Gly Leu
                    20                  25                  30

Tyr Gly Arg Phe Asn Cys Lys Ser Cys Trp Phe Val Asn Lys Gly Leu
                35                  40                  45

Ile Arg Cys Lys Asp His Tyr Leu Cys Leu Gly Cys Leu Thr Lys Met
        50                  55                  60

His Ser Arg Gly Asn Leu Cys Glu Ile Cys Gly His Ser Leu Pro Thr
    65                  70                  75                  80

Lys Met Glu Phe Leu Glu Ser Pro Ser Ala Pro Pro Tyr Glu Pro
                    85                  90                  95

<210> SEQ ID NO 2
    <211> LENGTH: 2194
    <212> TYPE: PRT
    <213> ORGANISM: Pichinde mammarenavirus

<400> SEQUENCE: 2

Met Glu Glu Tyr Val Phe Glu Leu Lys Asp Ile Val Arg Lys Trp Val
    1               5                   10                  15

Pro Glu Trp Glu Glu Leu Ser Glu Gln Lys Asn Asn Val Leu Ala Gln
                    20                  25                  30

Val Lys Asp Arg Ala Ile Thr Ile Glu Gly Leu Lys Leu Leu Ser Met
                35                  40                  45

Leu Val Glu Val Asp Ser Cys Lys Lys His Ser Cys Lys His Asn Thr
        50                  55                  60

Lys Met Thr Val Asn Ala Ile Leu Arg Glu Leu Arg Val Thr Cys Pro
    65                  70                  75                  80

Thr Leu Pro Asp Val Thr Pro Asp Gly Tyr Cys Met Val Gly Asp Val
                    85                  90                  95

Leu Ile Leu Leu Glu Val Phe Val Arg Thr Ser Gln Glu Ala Phe Glu
                    100                 105                 110

Lys Lys Tyr Asn Gln Asp Phe Leu Lys Leu Leu Gln Leu Ser Ser Asp
                115                 120                 125
```

```
Leu Lys Arg Gln Asn Ile Thr Leu Val Pro Val Ile Asp Gly Arg Ser
    130                 135                 140

Ser Tyr Tyr Val Glu Phe Val Pro Asp Trp Val Glu Arg Leu Arg
145                 150                 155                 160

Trp Leu Leu Leu Lys Leu Met Asp Gly Leu Arg Thr Ser Gly Glu Glu
                165                 170                 175

Val Glu Glu Leu Glu Tyr Glu Arg Leu Ile Ser Ser Leu Ser Ser Leu
                180                 185                 190

Glu Asn Gln Ser Leu Gly Leu Glu Ser Leu Leu Ala Val Lys Glu Arg
        195                 200                 205

Gly Leu Pro Tyr Lys Val Arg Leu Glu Lys Ala Leu Met Ser Gly Ile
210                 215                 220

Asn Asn Lys Leu Thr Thr Asp Gln Cys Arg Thr Lys Ile Met Glu Ile
225                 230                 235                 240

Phe Gln Gln Phe Lys Met Leu Gln Leu Ala Gly Gln Leu Asp Arg Lys
                245                 250                 255

Leu Gln Ala Thr Asp Arg Glu Asp Met Ile Ser Arg Leu Gln Asn His
                260                 265                 270

Glu Phe Ile Gln Cys Ser Val Lys Asp Val Pro Lys Ser Glu Ile Arg
        275                 280                 285

Leu Cys Glu Phe Cys Ser Val His Ile Leu Gly Ile Ile Gly Gln Leu
    290                 295                 300

Arg Gln Ser Glu Val Lys His Ser Ser Thr Glu Ser Arg Glu Tyr Phe
305                 310                 315                 320

Arg Val Leu Ser Ile Cys Asn Lys Ile Lys Ser Gln Lys Val Phe Asn
                325                 330                 335

Thr Arg Arg Asn Thr Met Leu Val Leu Asp Leu Ile Met Tyr Asn Ile
                340                 345                 350

Leu Cys Asp Leu Asp Lys Ser Ser Pro Gly Ala Val Phe Arg Glu Val
        355                 360                 365

Leu Leu Met Gln Gly Leu Pro Ser Val Asn Asp Arg Leu Ile Asn Val
    370                 375                 380

Asp Phe Leu Met Glu Gln Ile Thr Lys Lys Phe Ile Lys Asn Pro Asn
385                 390                 395                 400

Trp Leu Glu Lys Ala Lys Lys Arg Leu Ser Ser Val Cys Gly Glu Leu
                405                 410                 415

Pro Leu Asp Asp Ile Leu Pro Leu Leu Arg Glu Pro Asp Val Glu Tyr
                420                 425                 430

Tyr Phe Asn Leu Lys Thr Ser Val Leu Asp Glu Trp Gly Ala Lys Pro
        435                 440                 445

Cys Leu Gln Tyr Lys Thr Lys Ser Gln Cys Met Cys Gly Gly Arg Pro
450                 455                 460

Gly Arg Gly Gln Pro Asp Tyr Thr Ile Met Gly Glu Ser Glu Phe Glu
465                 470                 475                 480

Glu Leu Leu Lys Thr Leu Ser Ser Leu Ser Leu Ile Asn Ser
                485                 490                 495

Met Lys Thr Ala Ala Val Pro Lys Met Lys Val Asn Asn Ala Asp Glu
        500                 505                 510

Phe Tyr Gly Lys Val Tyr Cys Asp Glu Val Phe Phe Gln Arg Phe Gly
        515                 520                 525

Glu Gly Gly Ser Leu Thr Leu Leu Tyr Gln Lys Thr Gly Glu Arg Ser
530                 535                 540
```

-continued

Arg Cys Tyr Ala Val Ala Tyr Arg Ser Lys Ser Gly Gly Leu Tyr Glu
545                 550                 555                 560

Thr Lys Ala Ser Phe Tyr Cys Asp Pro Lys Arg Phe Phe Leu Pro Ile
                565                 570                 575

Phe Ser Ala Asp Val Ile Gln Arg Thr Cys Val Glu Met Leu Ser Trp
            580                 585                 590

Leu Asp Phe Met Ser Gln Pro Leu Leu Asp Ser Val Ser Asp Leu Leu
        595                 600                 605

Arg Arg Leu Ile Leu Cys Ile Leu Cys Thr Pro Ser Lys Arg Ile Gln
610                 615                 620

Val Tyr Leu Gln Gly Phe Arg Tyr Tyr Ile Met Ala Phe Val Asn Glu
625                 630                 635                 640

Val His Phe Lys Glu Leu Phe Glu Lys Leu Lys Val Val Met Leu Thr
                645                 650                 655

Pro Ser Glu Trp Gln Thr Ala Met Leu Ile Asp Asp Leu Ile Leu Leu
            660                 665                 670

Val Leu Ser Asn Ser Arg Glu Glu Asp Met Ala Lys Ile Phe Lys Phe
        675                 680                 685

Val Leu Asn Val Ser Tyr Leu Cys His Phe Ile Thr Lys Glu Thr Pro
690                 695                 700

Asp Arg Leu Thr Asp Gln Ile Lys Cys Phe Glu Lys Phe Leu Glu Pro
705                 710                 715                 720

Lys Leu Lys Phe Asp Ser Val Leu Val Asn Pro Ser Asn Ser Met Glu
                725                 730                 735

Leu Pro Thr Glu Glu Glu Lys Met Val His Asp Ile Glu Arg Leu
            740                 745                 750

Leu Gly Lys Lys Leu Glu Ser Lys Cys Glu Gly Arg Pro Gly Leu Asn
        755                 760                 765

Lys Asp Val Leu Ser Val Cys Leu Ser Leu Phe Asn Ser Ser Ser Leu
770                 775                 780

Glu Val Lys Pro Leu Leu Pro Cys Asp Pro Met Thr Pro Ser Phe Thr
785                 790                 795                 800

Ser Thr Ala Leu Asp Met Ser Ser Asn Lys Ser Val Val Pro Lys
                805                 810                 815

Leu Asn Glu Val Gly Glu Val Ile Thr Glu Tyr Asp Tyr Ser Ser Ile
            820                 825                 830

Val Ser Ala Val Val Glu Met Ile Glu His Phe Lys Thr Lys Gly
        835                 840                 845

Lys Tyr Lys Leu Asp Pro Lys Glu Val Asn Phe Lys Ile Leu Lys Arg
850                 855                 860

Leu Ser Ser Leu Ile Gln Ile Lys Lys Glu Ser Ile Glu Pro Asp Gly
865                 870                 875                 880

Val Glu Glu Leu Leu Ser Glu Asp Gln Gly Asp Cys Leu Lys Glu Ile
                885                 890                 895

Glu Thr Arg Val Ala Lys Val Leu Ser Lys Val Asp Thr Asn Val Lys
            900                 905                 910

Thr Asn Leu Lys Thr Ser Cys Pro Leu Glu Arg Leu Trp Pro Lys Ser
        915                 920                 925

Thr Met Val Val Ile Lys Arg Glu Thr Ser Leu His Asp Val Lys Asp
930                 935                 940

Phe Asp Tyr Ser Leu Phe Ser Ala Glu Val Tyr Glu Asp Leu Val Asn
945                 950                 955                 960

Leu Ile Tyr Glu Asp Val Thr Ala Arg Ser Val Tyr Phe Ala Asp Arg

-continued

```
            965                 970                 975
Leu Met Asn Pro Cys Pro Leu Glu Phe Leu Ile Lys Asn Leu Thr Leu
                980                 985                 990
Lys Ala Tyr Lys Glu Ala Asp Tyr Phe Glu Cys Phe Lys Tyr Ile Leu
                995                 1000                1005
Ile Ala Ser Asp Tyr Asp Asn Arg Val Gly Arg Tyr Asp His Lys
            1010                1015                1020
Ser Arg Ser Arg Leu Gly Phe Thr Asp Ala Ala Leu Gln Ile Arg
            1025                1030                1035
Glu Thr Ser Arg Ile Ser Ser Arg Glu Ser Asn Ser Glu Ser Ile
            1040                1045                1050
Ala Lys Arg Leu Asp Gln Ser Phe Phe Thr Asn Ser Ser Leu Arg
            1055                1060                1065
Asn Leu Cys Phe Tyr Ser Asp Glu Ser Pro Thr Glu Arg Ser Gly
            1070                1075                1080
Val Ser Thr Asn Val Gly Arg Leu Lys Phe Gly Leu Ser Tyr Lys
            1085                1090                1095
Glu Gln Val Gly Gly Asn Arg Glu Leu Tyr Val Gly Asp Leu Asn
            1100                1105                1110
Thr Lys Leu Thr Thr Arg Leu Ile Glu Asp Tyr Ser Glu Ser Leu
            1115                1120                1125
Met Gln Asn Met Arg Tyr Thr Cys Leu Asn Asn Glu Lys Glu Phe
            1130                1135                1140
Glu Arg Ala Leu Leu Asp Met Lys Ser Val Val Arg Gln Ser Gly
            1145                1150                1155
Leu Ala Val Ser Met Asp His Ser Lys Trp Gly Pro His Met Ser
            1160                1165                1170
Pro Val Ile Phe Ala Ala Leu Leu Lys Gly Leu Glu Phe Lys Leu
            1175                1180                1185
Lys Asp Gly Ser Glu Val Pro Asn Ala Ala Val Ile Asn Ile Leu
            1190                1195                1200
Leu Trp His Ile His Lys Met Val Glu Val Pro Phe Asn Val Val
            1205                1210                1215
Glu Ala Tyr Met Lys Gly Phe Leu Lys Arg Gly Leu Gly Met Met
            1220                1225                1230
Asp Lys Gly Gly Cys Thr Ile Ala Glu Glu Phe Met Phe Gly Tyr
            1235                1240                1245
Phe Glu Lys Gly Lys Val Pro Ser His Ile Ser Ser Val Leu Asp
            1250                1255                1260
Met Gly Gln Gly Ile Leu His Asn Thr Ser Asp Leu Tyr Gly Leu
            1265                1270                1275
Ile Thr Glu Gln Phe Ile Asn Tyr Ala Leu Glu Leu Cys Tyr Gly
            1280                1285                1290
Ala Arg Phe Ile Ser Tyr Thr Ser Ser Asp Asp Glu Ile Met Leu
            1295                1300                1305
Ser Leu Asn Glu Gly Phe Lys Phe Lys Asp Arg Asp Glu Leu Asn
            1310                1315                1320
Val Glu Leu Val Leu Asp Cys Met Glu Phe His Tyr Phe Leu Ser
            1325                1330                1335
Asp Lys Leu Asn Lys Phe Val Ser Pro Lys Thr Val Val Gly Thr
            1340                1345                1350
Phe Ala Ser Glu Phe Lys Ser Arg Phe Phe Ile Trp Ser Gln Glu
            1355                1360                1365
```

```
Val Pro Leu Leu Thr Lys Phe Val Ala Ala Leu His Asn Ile
    1370            1375            1380

Lys Ala Lys Ala Pro Asn Gln Gln Ala Asp Thr Ile Asp Thr Ile
    1385            1390            1395

Leu Asp Gln Cys Val Ala Asn Gly Val Ser Ile Glu Val Val Gly
    1400            1405            1410

Ala Ile Ala Lys Arg Thr Asn Ser Met Ile Ile Tyr Ser Gly Phe
    1415            1420            1425

Pro Asn Asp Pro Phe Leu Cys Leu Glu Glu Met Asp Val Leu Asp
    1430            1435            1440

Trp Val Asn Gly Ser Arg Gly Tyr Arg Leu Gln Arg Ser Ile Glu
    1445            1450            1455

Thr Leu Phe Pro Asp Asp Leu Leu Leu Ser Ile Ile Arg Lys Ala
    1460            1465            1470

Cys Arg Lys Ile Phe Tyr Lys Ile Gln Ser Gly Ala Leu Glu Glu
    1475            1480            1485

Ser Tyr Ile Val Thr Thr Leu Gln Gln Ser Pro Asp Asp Cys Leu
    1490            1495            1500

Lys Gln Leu Leu Glu Thr Cys Asp Val Glu Thr Glu Ala Ile Glu
    1505            1510            1515

Asp Ala Leu Asn Ile Arg Trp Leu Asn Leu Arg Val His Gly Asp
    1520            1525            1530

Leu Arg Leu Val Leu Arg Thr Lys Leu Met Ser Thr Thr Arg Thr
    1535            1540            1545

Val Gln Arg Glu Glu Ile Pro Ser Leu Val Lys Ser Val Gln Ser
    1550            1555            1560

Lys Leu Ser Lys Asn Tyr Val Arg Gly Ala Lys Lys Ile Leu Ala
    1565            1570            1575

Asp Ala Ile Asn Lys Ser Ala Phe Gln Ser Ser Ile Ala Ser Gly
    1580            1585            1590

Phe Ile Gly Val Cys Lys Ser Met Gly Ser Lys Cys Val Arg Asp
    1595            1600            1605

Gly Lys Gly Gly Phe Lys Tyr Ile Arg Asp Ile Thr Ser Lys Ile
    1610            1615            1620

Ile Leu His Arg Asp Cys His Phe Cys Asn Gln Arg Lys Gly Val
    1625            1630            1635

Tyr Cys Lys Ala Ala Leu Gly Glu Val Ser Glu Tyr Ser Arg Pro
    1640            1645            1650

Leu Ile Trp Asp Tyr Phe Ala Leu Val Leu Thr Asn Ala Cys Glu
    1655            1660            1665

Leu Gly Asn Trp Val Phe Gln Lys Ala Glu Val Pro Lys Ile Val
    1670            1675            1680

Thr His Leu Asn Asn Pro Asn His Phe Trp Pro Ile Lys Pro Ser
    1685            1690            1695

Thr His Ser Glu Leu Glu Asp Lys Val Gly Ile Asn His Ile Leu
    1700            1705            1710

Tyr Ser Ile Arg Arg Asn Phe Pro Thr Leu Phe Asp Glu His Ile
    1715            1720            1725

Ser Pro Phe Leu Ser Asp Leu Asn Met Leu Arg Leu Ser Trp Val
    1730            1735            1740

Gln Arg Ile Lys Phe Leu Asp Leu Cys Val Ala Ile Asp Ile Thr
    1745            1750            1755
```

-continued

```
Ser Glu Cys Leu Gly Ile Val Ser His Ile Ile Lys His Arg Arg
    1760                1765                1770
Glu Glu Leu Tyr Ile Val Lys Gln Asn Glu Leu Ala Met Ser His
    1775                1780                1785
Ser Arg Glu Ser His Pro Leu Glu Arg Gly Phe Asn Leu Glu Pro
    1790                1795                1800
Glu Glu Val Cys Thr Asn Phe Leu Ile Gln Ile Leu Phe Glu Ser
    1805                1810                1815
Met Leu Val Pro Val Ile Met Ser Thr Ser Gln Phe Lys Lys Tyr
    1820                1825                1830
Phe Trp Phe Gly Glu Leu Glu Leu Leu Pro Asn Asn Ala Gln His
    1835                1840                1845
Asp Leu Lys Gln Leu Thr Gln Phe Ile Cys Asp Cys Lys Lys Asn
    1850                1855                1860
Asn Thr Ser Arg Thr Met Asn Leu Asp Asp Leu Asp Val Gly Phe
    1865                1870                1875
Val Ser Ser Lys Leu Ile Leu Ser Cys Val Asn Leu Asn Ile Ser
    1880                1885                1890
Val Phe Ile Asn Glu Leu Asp Trp Val Asn Arg Asp Asn Tyr Glu
    1895                1900                1905
Asn Ile Glu Gln Leu Ile Leu Ala Ser Pro Ser Glu Val Ile Pro
    1910                1915                1920
Ile Glu Leu Asn Leu Thr Phe Ser His Lys Arg Val Ser His Lys
    1925                1930                1935
Phe Arg Tyr Glu Arg Ser Thr Asn Tyr Ile Leu Lys Leu Arg Phe
    1940                1945                1950
Leu Ile Glu Arg Glu Ser Leu Leu Asp Ser Leu Asp Ser Asp Gly
    1955                1960                1965
Tyr Leu Leu Leu Asn Pro His Ser Val Glu Tyr Tyr Val Ser Gln
    1970                1975                1980
Ser Ser Gly Asn His Ile Ser Leu Asp Gly Val Ser Leu Leu Val
    1985                1990                1995
Leu Asn Pro Leu Ile Asn Gly Lys Asp Val Leu Asp Phe Asn Asp
    2000                2005                2010
Leu Leu Glu Gly Gln Asp Ile His Phe Lys Ser Arg Ser Thr Val
    2015                2020                2025
Phe Gln Lys Val Arg Ile Asp Leu Lys Asn Arg Phe Lys Asp Leu
    2030                2035                2040
Lys Asn Lys Phe Ser Tyr Lys Leu Ile Gly Pro Asp Val Gly Met
    2045                2050                2055
Gln Pro Leu Ile Leu Glu Gly Gly Leu Ile Lys Glu Gly Asn Arg
    2060                2065                2070
Val Val Ser Arg Leu Glu Val Asn Leu Asp Ser Lys Val Val Ile
    2075                2080                2085
Ile Ala Leu Glu Ala Leu Glu Pro Glu Lys Arg Pro Arg Phe Ile
    2090                2095                2100
Ala Asn Leu Phe Gln Tyr Leu Ser Ser Ala Gln Ser His Asn Lys
    2105                2110                2115
Gly Ile Ser Met Asn Glu Gln Asp Leu Arg Leu Met Ile Glu Asn
    2120                2125                2130
Phe Pro Glu Val Phe Glu His Met Leu His Asp Ala Lys Asp Trp
    2135                2140                2145
Leu Asn Cys Gly His Phe Ser Ile Ile Arg Ser Lys Thr Leu Gly
```

```
        2150                2155                2160
Ser Val Met Ile Ala Asp Glu Thr Gly Pro Phe Lys Ile Lys Gly
        2165                2170                2175

Ile Arg Cys Arg Lys Leu Phe Glu Asp Asn Glu Ser Val Glu Ile
        2180                2185                2190

Glu

<210> SEQ ID NO 3
<211> LENGTH: 560
<212> TYPE: PRT
<213> ORGANISM: Pichinde mammarenavirus

<400> SEQUENCE: 3

Met Ser Asp Asn Ile Pro Ser Phe Arg Trp Val Gln Ser Leu Arg Arg
1               5                   10                  15

Gly Leu Ser Asn Trp Thr His Pro Val Lys Ala Asp Val Leu Ser Asp
            20                  25                  30

Thr Arg Ala Leu Leu Ser Ala Leu Asp Phe His Lys Val Ala Gln Val
        35                  40                  45

Gln Arg Met Met Arg Lys Asp Lys Arg Thr Asp Ser Asp Leu Thr Lys
    50                  55                  60

Leu Arg Asp Met Asn Lys Glu Val Asp Ala Leu Met Asn Met Arg Ser
65                  70                  75                  80

Ile Gln Arg Asp Asn Val Leu Lys Val Gly Gly Leu Ala Lys Glu Glu
                85                  90                  95

Leu Met Glu Leu Ala Ser Asp Leu Asp Lys Leu Arg Lys Lys Val Thr
            100                 105                 110

Arg Thr Glu Ser Leu Ser Gln Pro Gly Val Tyr Gly Gly Asn Leu Thr
        115                 120                 125

Asn Thr Gln Leu Glu Gln Arg Ala Glu Ile Leu Arg Ser Met Gly Phe
    130                 135                 140

Ala Asn Ala Arg Pro Thr Gly Asn Arg Asp Gly Val Val Lys Ile Trp
145                 150                 155                 160

Asp Ile Lys Asp Asn Thr Leu Leu Ile Asn Gln Phe Gly Ser Met Pro
                165                 170                 175

Ala Leu Thr Ile Ala Cys Met Thr Glu Gln Gly Gly Glu Gln Leu Asn
            180                 185                 190

Asp Val Val Gln Ala Leu Ser Ala Leu Gly Leu Leu Tyr Thr Val Lys
        195                 200                 205

Phe Pro Asn Met Thr Asp Leu Glu Lys Leu Thr Gln Gln His Ser Ala
    210                 215                 220

Leu Lys Ile Ile Ser Asn Glu Pro Ser Ala Ile Asn Ile Ser Gly Tyr
225                 230                 235                 240

Asn Leu Ser Leu Ser Ala Ala Val Lys Ala Ala Ala Cys Met Ile Asp
                245                 250                 255

Gly Gly Asn Met Leu Glu Thr Ile Gln Val Lys Pro Ser Met Phe Ser
            260                 265                 270

Thr Leu Ile Lys Ser Leu Leu Gln Ile Lys Asn Arg Glu Gly Met Phe
        275                 280                 285

Val Ser Thr Thr Pro Gly Gln Arg Asn Pro Tyr Glu Asn Leu Leu Tyr
    290                 295                 300

Lys Ile Cys Leu Ser Gly Asp Gly Trp Pro Tyr Ile Gly Ser Arg Ser
305                 310                 315                 320

Gln Val Gln Gly Arg Ala Trp Asp Asn Thr Thr Val Asp Leu Asp Ser
```

```
              325                 330                 335
Lys Pro Ser Ala Ile Gln Pro Val Arg Asn Gly Gly Ser Pro Asp
            340                 345                 350
Leu Lys Gln Ile Pro Lys Glu Lys Asp Thr Val Val Ser Ser Ile Gln
            355                 360                 365
Met Leu Asp Ser Lys Ala Thr Thr Trp Ile Asp Ile Glu Gly Thr Pro
            370                 375                 380
Asn Asp Pro Val Glu Met Ala Ile Tyr Gln Pro Asp Thr Gly Asn Tyr
385                 390                 395                 400
Ile His Cys Tyr Arg Phe Pro His Asp Glu Lys Ser Phe Lys Glu Gln
                405                 410                 415
Ser Lys Tyr Ser His Gly Leu Leu Leu Lys Asp Leu Ala Asp Ala Gln
            420                 425                 430
Pro Gly Leu Ile Ser Ser Ile Ile Arg His Leu Pro Gln Asn Met Val
            435                 440                 445
Phe Thr Ala Gln Gly Ser Asp Asp Ile Ile Ser Leu Phe Glu Met His
            450                 455                 460
Gly Arg Arg Asp Leu Lys Val Leu Asp Val Lys Leu Ser Ala Glu Gln
465                 470                 475                 480
Ala Arg Thr Phe Glu Asp Glu Ile Trp Glu Arg Tyr Asn Leu Leu Cys
                485                 490                 495
Thr Lys His Lys Gly Leu Val Ile Lys Lys Lys Lys Gly Ala Ala
                500                 505                 510
Gln Thr Thr Ala Asn Pro His Cys Ala Leu Leu Asp Thr Ile Met Phe
            515                 520                 525
Asp Ala Thr Val Thr Gly Trp Val Arg Asp Gln Lys Pro Met Arg Cys
            530                 535                 540
Leu Pro Ile Asp Thr Leu Tyr Arg Asn Asn Thr Asp Leu Ile Asn Leu
545                 550                 555                 560

<210> SEQ ID NO 4
<211> LENGTH: 508
<212> TYPE: PRT
<213> ORGANISM: Pichinde mammarenavirus

<400> SEQUENCE: 4

Met Gly Gln Val Val Thr Leu Ile Gln Ser Ile Pro Glu Val Leu Gln
1               5                   10                  15
Glu Val Phe Asn Val Ala Leu Ile Ile Val Ser Thr Leu Cys Ile Ile
                20                  25                  30
Lys Gly Phe Val Asn Leu Met Arg Cys Gly Leu Phe Gln Leu Ile Thr
                35                  40                  45
Phe Leu Ile Leu Ala Gly Arg Ser Cys Asp Gly Met Met Ile Asp Arg
            50                  55                  60
Arg His Asn Leu Thr His Val Glu Phe Asn Leu Thr Arg Met Phe Asp
65                  70                  75                  80
Asn Leu Pro Gln Ser Cys Ser Lys Asn Asn Thr His His Tyr Tyr Lys
                85                  90                  95
Gly Pro Ser Asn Thr Thr Trp Gly Ile Glu Leu Thr Leu Thr Asn Thr
                100                 105                 110
Ser Ile Ala Asn Glu Thr Thr Gly Asn Phe Ser Asn Ile Arg Ser Leu
            115                 120                 125
Ala Tyr Gly Asn Ile Ser Asn Cys Asp Lys Thr Glu Glu Ala Gly His
            130                 135                 140
```

-continued

```
Thr Leu Lys Trp Leu Leu Asn Glu Leu His Phe Asn Val Leu His Val
145                 150                 155                 160

Thr Arg His Val Gly Ala Arg Cys Lys Thr Val Glu Gly Ala Gly Val
                165                 170                 175

Leu Ile Gln Tyr Asn Leu Thr Val Gly Asp Arg Gly Gly Glu Val Gly
            180                 185                 190

Arg His Leu Ile Ala Ser Leu Ala Gln Ile Ile Gly Asp Pro Lys Ile
        195                 200                 205

Ala Trp Val Gly Lys Cys Phe Asn Asn Cys Ser Gly Gly Ser Cys Arg
    210                 215                 220

Leu Thr Asn Cys Glu Gly Gly Thr His Tyr Asn Phe Leu Ile Ile Gln
225                 230                 235                 240

Asn Thr Thr Trp Glu Asn His Cys Thr Tyr Thr Pro Met Ala Thr Ile
                245                 250                 255

Arg Met Ala Leu Gln Lys Thr Ala Tyr Ser Ser Val Ser Arg Lys Leu
            260                 265                 270

Leu Gly Phe Phe Thr Trp Asp Leu Ser Asp Ser Thr Gly Gln His Val
        275                 280                 285

Pro Gly Gly Tyr Cys Leu Glu Gln Trp Ala Ile Val Trp Ala Gly Ile
    290                 295                 300

Lys Cys Phe Asp Asn Thr Val Met Ala Lys Cys Asn Lys Asp His Asn
305                 310                 315                 320

Glu Glu Phe Cys Asp Thr Met Arg Leu Phe Asp Phe Asn Gln Asn Ala
                325                 330                 335

Ile Lys Thr Leu Gln Leu Asn Val Glu Asn Ser Leu Asn Leu Phe Lys
            340                 345                 350

Lys Thr Ile Asn Gly Leu Ile Ser Asp Ser Leu Val Ile Arg Asn Ser
        355                 360                 365

Leu Lys Gln Leu Ala Lys Ile Pro Tyr Cys Asn Tyr Thr Lys Phe Trp
    370                 375                 380

Tyr Ile Asn Asp Thr Ile Thr Gly Arg His Ser Leu Pro Gln Cys Trp
385                 390                 395                 400

Leu Val His Asn Gly Ser Tyr Leu Asn Glu Thr His Phe Lys Asn Asp
                405                 410                 415

Trp Leu Trp Glu Ser Gln Asn Leu Tyr Asn Glu Met Leu Ile Lys Glu
            420                 425                 430

Tyr Glu Glu Arg Gln Gly Lys Thr Pro Leu Ala Leu Thr Asp Ile Cys
        435                 440                 445

Phe Trp Ser Leu Val Phe Tyr Thr Ile Thr Val Phe Leu His Leu Val
    450                 455                 460

Gly Ile Pro Thr His Arg His Ile Ile Gly Asp Gly Cys Pro Lys Pro
465                 470                 475                 480

His Arg Ile Thr Arg Asn Ser Leu Cys Ser Cys Gly Tyr Tyr Lys Ile
                485                 490                 495

Pro Lys Lys Pro Tyr Lys Trp Val Arg Leu Gly Lys
            500                 505
```

<210> SEQ ID NO 5
<211> LENGTH: 7057
<212> TYPE: DNA
<213> ORGANISM: Pichinde mammarenavirus

<400> SEQUENCE: 5

```
cgcaccgggg atcctaggca tctttgggtc acgcttcaaa tttgtccaat ttgaacccag     60
```

```
ctcaagtcct ggtcaaaact tgggatggga ctcagatata gcaaagaggt caggaagaga    120
catggcgacg aagatgtggt gggaagggtc cccatgaccc tcaatctacc acagggcctg    180
tatggcaggt tcaactgcaa atcttgctgg ttcgtcaaca aaggtctcat caggtgcaaa    240
gaccactatc tgtgtcttgg gtgcttaacc aaaatgcact ccagaggcaa tctctgcgag    300
atatgcggcc actcactgcc aaccaagatg gagttcctag aaagcccctc tgcaccaccc    360
tacgagccat aaaccagggc ccctgggcgc accccctcc ggggtgcgc cggggccc       420 ccggcccat ggggccggtt gtttactcga tctccactga ctcattgtcc tcaaacaact    480
ttcgacacct gattcccttg atcttgaagg gtcctgtctc gtctgcaatc ataacagatc    540
ctagagtctt acttcttatt atactaaagt gaccacaatt caaccaatct ttggcatcat    600
gcaacatgtg ttcaaacact tcggggaaat tttcaatcat gagtcttaaa tcctgctcgt    660
tcatacttat tcccttgttg tgagactgtg cacttgaaag gtactgaaaa aggttggcaa    720
taaatcttgg ccttttctca ggttctaatg cttccagtgc aatgatgacc acctttgagt    780
ctaagttcac ttccaatcta gaaaccactc tgttgccctc tttgatcaac ccaccctcta    840
aaatgagggg ttgcatccca acatcaggac caatcaactt ataggaaaat ttgtttttca    900
aatccttgaa acgattttc aaatctattc tcaccttctg gaacacagtt gaccttgact    960
tgaagtgaat gtcttgacct tccaatagat cattgaagtc tagaacatct tttccgttga   1020
tgagaggatt cagaaccaaa agtgacacac catccgagact tatgtgattc ccggaagatt   1080
gagaaacata atactcaaca gaatgggggt tcaacaatag gtaaccatca gagtccaatg   1140
agtccagcaa tgactcccctt tcaataagaa atcttaattt taatatgtaa ttggtagacc   1200
tctcatatct aaatttgtgg ctcactctct tatgagaaaa tgttaggttg agctcaatgg   1260
gaatgacctc agaaggtgat gctaaaatga gttgttcaat gttctcatag ttatctctat   1320
tcacccagtc aagttcatta ataaatacac taatgttcaa attaacacag gacaaaatca   1380
gtttgctgct tacaaagcca acatccaagt catccagatt cattgtccta gaagtgttat   1440 tcttttgca gtcacaaatg aactgggtta attgtttcag atcatgttgt gcattgtttg    1500
gcaacaattc aagctcacca aaccaaaaat atttcttgaa ctgagatgtt gacataatca   1560
caggcaccaa cattgactca aacaaaatct gtatcaagaa atttgtgcac acttcttctg   1620
gttcaaggtt gaatcctctc tccagtggat gagactctct gctatgggac attgcaagct   1680 catttttgctt tacaatatac aattcttctc tgcgatgttt tataatatga ctaacaatac   1740
caagacattc tgatgttata tcaattgcca cacaaaggtc taagaacttt atcctctgaa   1800
cccatgatag cctcagcata ttcaaatcag acaggaaagg ggatatgtgt tcatcaaata   1860
gtgtagggaa gttcctcctg attgagtaaa gtatgtggtt gatgcccacc ttgtcctcaa   1920
gctcagaatg tgtgcttggt tttattggcc agaagtgatt gggattgttt aggtgagtga   1980
ctatcttggg tacttcagct ttttgaaaca cccagttacc caactcgcaa gcattggtta   2040
acacaagagc aaaataatcc caaattaagg gtctggagta ctcacttact tcaccaagtg   2100
ctgctttaca ataaacacct ttgcgctgat tacaaaagtg acaatcacgg tgtaagataa   2160
tcttgcttgt aatatccctg atatacttaa atcctccttt cccgtctctt acacattttg   2220
agcccatact tttgcaaact cctatgaatc ctgatgctat gctgctctga aaagctgatt   2280
tgttgatagc atcagccaaa atcttcttag cccctctgac atagttcttt gataaatttgg   2340 actgtacgga tttgacaaga ctgggtattt cttctcgctg cacagttctt gttgtgctca   2400
ttaacttagt acgaagcacc aatctgagat caccatgaac ccttaaattt aaccacctaa   2460
```

```
tattaagagc atcctcaata gcctcagtct cgacatcaca agtctctaat aactgtttta    2520
agcagtcatc cggtgattgc tgaagagttg ttacaatata actttcttcc agggctccag    2580
actgtatttt gtaaaatatt ttcctgcatg cctttctgat tattgaaagt agcagatcat    2640
caggaaatag tgtctcaatt gatcgctgaa gtctgtaccc tctcgaccca ttaacccaat    2700
cgagtacatc catttcttcc aggcacaaaa atggatcatt tggaaaccca ctatagatta    2760
tcatgctatt tgttcgtttt gcaatggccc ctacaacctc tattgacacc ccgttagcaa    2820
cacattggtc cagtattgtg tcaattgtat ctgcttgctg attgggtgct ttagccttta    2880
tgttgtgtag agctgcagca acaaactttg taaggagggg gacttcttgt gaccaaatga    2940
agaatctcga tttgaactca cttgcaaagg tccccacaac tgttttaggg ctcacaaact    3000
tgttgagttt gtctgataga aagtagtgaa actccataca gtccaatacc aattcaacat    3060
tcaactcatc tctgtcctta aatttgaaac cctcattcaa ggataacatg atctcatcat    3120
cactcgaagt atatgagatg aaccgtgctc cataacaaag ctccaatgcg taattgatga    3180
actgctcagt gattagacca tataagtcag aggtgttgtg taggatgccc tgacccatat    3240
ctaagactga agagatgtgt gatggtacct tgcccttctc aaagtaccca aacataaatt    3300
cctctgcaat tgtgcaccccc cctttatcca tcatacccaa ccccctttttc aagaaacctt    3360 tcatgtatgc ctcaacgaca ttgaagggca cttccaccat cttgtgaatg tgccatagca    3420
atatgttgat gactgcagca ttgggaactt ctgacccatc tttgagtttg aactcaagac    3480
cttttaataa tgcggcaaag ataaccggcg acatgtgtgg ccccatttt gaatggtcca    3540 ttgacaccgc aagaccactt tgcctaacaa ctgacttcat gtctaataat gctctctcaa    3600 actcttttctc gttgttcaga caagtatacc tcatgtttttg cataagggat tcagagtaat    3660
cctcaatgag tctggttgtg agtttagtat ttaaatcacc gacataaagc tccctgttgc    3720
cacccacctg ttctttataa gaaagaccaa atttcaatct ccctacattg gtggatacac    3780
cagacctctc tgtgggagac tcatctgaat agaaacagag atttcgtaag gatgagttgg    3840
taaaaaagct ttgatccaat cttttagcta tcgattcaga attgctctct cttgagctta    3900
tacgtgatgt ctctctaatt tgtagtgctg catctgtgaa cccaagtctg cttctacttt    3960
tgtgatcata tcttccgact cgattatcat aatcgcttgc aatgagaatg tatttaaagc    4020
actcaaaata atcagcttct ttgtacgcct tcaatgtgag gttctttatt aaaaactcca    4080
gaggacacgg attcattagt ctgtctgcaa agtacactga tctagcagtg acatcctcat    4140
agatcaagtt tacaagatcc tcatacactt ctgctgaaaa caggctgtaa tcaaaatcct    4200
ttacatcatg aagtgaagtc tctcttttga tgacaaccat tgtcgatttg ggccataatc    4260
tctctagtgg acatgaagtc ttaaggttgg ttttgacatt ggtgtcaacc ttagacaata    4320
cttttgcaac tctggtctca atttcttttaa gacagtcacc ctgatcttct gatagtaact    4380
cttcaactcc atcaggctct attgactcct ttttatttg atcaatgat gacaacctct    4440 tcagaatctt gaaatttacc tcctttggat ccaacttgta tttacccctta gttttgaaat    4500 gttcaatcat ttccacaaca acagcagaca caatggaaga gtaatcatat tcagtgatga    4560
cctcaccaac ttcattgagt tttggaacca ccacactttt gttgctggac atatccaagg    4620
ctgtacttgt gaaggaggga gtcatagggt cacaaggaag caggggtttc acttccaatg    4680
agctactgtt aaatagtgat agacaaacac taagtacatc cttattcaac cccggccttc    4740
cctcacattt ggattccagc ttttaccaa gtagtctctc tatatcatgc accatcttct    4800
```

```
cttcttcctc agtaggaagt tccatactat tagaagggtt gaccaagact gaatcaaact    4860
ttaactttgg ttccaagaac ttctcaaaac atttgatttg atcagttaat ctatcagggg    4920
tttctttggt tataaaatgg cataaatagg agacattcaa aacaaactta aagatcttag    4980
ccatatcttc ctctctggag ttgctgagta ccagaagtat caaatcatca ataagcattg    5040
ctgtctgcca ttctgaaggt gttagcataa cgactttcaa tttctcaaac aattctttaa    5100
aatgaacttc atttacaaag gccataatgt aatatctaaa gccttgcaag taaacttgaa    5160
tacgcttgga aggggtgcac agtatgcaga gaataagtcg tctgagtaaa tcagaaacag    5220
aatccaagag gggttgggac ataaagtcca accaggataa catctccaca caagtccttt    5280
gaatcacatc tgcactaaag atcggtaaga aaaatctctt gggatcacag taaaaagacg    5340
cttttgtttc atacaaaccc ccacttttgg atctataagc aacagcataa cacctggacc    5400
tctcccctgt cttctggtac agtagtgtga gagaacctcc ttctccaaat cgctggaaga    5460
aaacttcgtc acagtaaacc ttcccataaa actcatcagc attgttcacc ttcatcttag    5520
gaactgctgc tgtcttcatg ctattaatga gtgacaaact caaacttgac aatgttttca    5580
gcaattcctc aaactcactt tcgcccatga tggtataatc aggctgccct cttcctggcc    5640
tacccccaca catacactgt gactttgtct tgtattgaag acagggttta gcaccccatt    5700
catctaacac tgatgttttc agattgaagt aatattcaac atcaggttcc cgtagaagag    5760
ggagaatgtc atcaagggga agttcaccac agaccgagct cagtctcttc ttagccttct    5820
ctaaccagtt ggggtttttta atgaattttt tagtgatttg ttccatcagg aagtcgacat    5880
taatcaacct gtcatttaca gacggtaacc cttgcattag gagcacctct ctgaacacag    5940
cacctggaga agacttgtcc aagtcacaca aaatgttgta catgataagg tccagaacca    6000
acatggtgtt cctccttgtg ttaaaaacct tttgagactt aattttgttg catattgaaa    6060
gtactctaaa atattctctg ctttcagttg atgaatgctt gacctcagat tgcctgagtt    6120
ggcctattat gcccaaaatg tgtactgagc aaaactcaca taatctgatt tctgatttag    6180
gtacatcttt gacagaacat tggataaatt catggttctg aagtctagaa atcatatctt    6240
ccctatctgt agcctgcagt ttcctatcga gttgaccagc aagttgcaac atttaaatt    6300
gctgaaagat ttccatgatt tttgttctac attgatctgt tgtcagttta ttattaatgc    6360
cagacattaa tgccttttcc aacctcactt tgtaaggaag tcccctttcc tttacagcaa    6420
gtagtgactc cagaccgaga ctctgatttt ctaaggatga gagggaactt ataaggcgtt    6480
cgtactccaa ctcctcaact tcttcaccag atgtccttaa tccatccatg agttttaaaa    6540
gcaaccaccg aagtctctct accacccaat caggaacaaa ttctacataa taactggatc    6600
taccgtcaat aacaggtact aaggttatgt tctgtctctt gagatcagaa ctaagctgca    6660
acagcttcaa aaagtcctgg ttgtatttct tctcaaatgc ttcttgactg gtcctcacaa    6720
acacttccaa aagaatgagg acatctccaa ccatacagta accatctggt gtaacatccg    6780
gcaatgtagg acatgttact ctcaactccc taaggatagc attgacagtc atctttgtgt    6840
tgtgtttgca ggagtgtttc ttgcatgaat ccacttccac tagcatggac aaaagcttca    6900
ggccctctat cgtgatggcc ctatctttga cttgtgcaag aacgttgttt ttctgttcag    6960
atagctcttc ccattcggga acccattttc tgactatgtc tttaagttcg aaaacgtatt    7020
cctccatgat caagaaatgc ctaggatcct cggtgcg                             7057
```

<210> SEQ ID NO 6
<211> LENGTH: 3421

<212> TYPE: DNA
<213> ORGANISM: Pichinde mammarenavirus

<400> SEQUENCE: 6

| | | | | | |
|---|---|---|---|---|---|
| cgcaccgggg | atcctaggca | taccttggac | gcgcatatta | cttgatcaaa | gatgggacaa | 60 |
| gttgtgactt | tgatccagtc | tatacccgaa | gtcctgcagg | aggtcttcaa | tgtcgcctta | 120 |
| atcattgtct | caaccctatg | catcatcaaa | ggatttgtca | atctgatgag | atgtggccta | 180 |
| ttccaactca | tcaccttcct | cattttggct | ggcagaagtt | gtgatggcat | gatgattgat | 240 |
| aggaggcaca | atctcaccca | cgttgagttc | aacctcacaa | gaatgtttga | caacttgcca | 300 |
| caatcatgta | gcaagaacaa | cacacatcat | tactacaaag | gaccatctaa | cacaacatgg | 360 |
| ggaattgaac | tcactttgac | aaacacatcc | attgcaaatg | aaactactgg | aaacttttcc | 420 |
| aacatcagaa | gccttgcata | tggtaacatt | agtaattgtg | ataagacaga | gaagcaggt | 480 |
| cacacattaa | atggttgct | taatgagtta | cacttcaatg | tgctccatgt | cactcgtcat | 540 |
| gtaggtgcca | gatgcaaaac | agttgagggt | gctggggtgt | tgatccagta | caacttgaca | 600 |
| gttggggata | gaggaggtga | ggttggcaga | catcttattg | cgtcgcttgc | tcaaatcatt | 660 |
| ggggacccaa | aaattgcgtg | ggttggaaaa | tgtttcaata | actgtagtgg | agggtcttgc | 720 |
| agactaacaa | actgtgaagg | tgggacacat | tacaatttcc | tgatcataca | gaacaccaca | 780 |
| tgggaaaatc | actgtacata | tactccaatg | gcaacaataa | ggatggctct | ccaaaaaact | 840 |
| gcttatagtt | ctgtgagcag | gaaactcctt | ggcttttca | cttgggactt | gagtgactct | 900 |
| actgggcaac | atgtcccagg | tggttactgt | ttggagcaat | gggctattgt | ttgggctgga | 960 |
| ataaaatgtt | ttgataacac | tgtgatggca | aaatgcaaca | agatcacaa | tgaagaattt | 1020 |
| tgcgatacga | tgaggttatt | tgatttcaat | cagaatgcta | tcaaaacctt | acaacttaat | 1080 |
| gttgagaatt | cgttgaatct | ctttaaaaag | actatcaacg | gacttatttc | tgactcactt | 1140 |
| gtgattagaa | acagtctcaa | acagcttgcc | aaaatccctt | attgcaacta | tacaaaattt | 1200 |
| tggtacatca | atgataccat | cacaggaaga | cattctttac | cgcagtgttg | gttagttcac | 1260 |
| aatggctcgt | acctcaatga | aacgcatttt | aagaatgatt | ggttgtggga | gagccagaat | 1320 |
| ctgtacaatg | aaatgctgat | aaaagaatat | gaagaaagac | aaggtaagac | tccactagca | 1380 |
| ttgacagaca | tttgcttctg | gtcttttggtg | ttttacacca | tcacagtgtt | tctccactta | 1440 |
| gttgaatac | ccactcatag | gcacatcatt | ggtgatggct | gtccgaagcc | acataggatt | 1500 |
| actaggaact | ctcttttgcag | ctgtgggtat | tataaaatcc | caagaaaacc | ctacaaatgg | 1560 |
| gtgagactgg | gtaaataagc | cctagcctcg | acatgggcct | cgacgtcact | ccccaatagg | 1620 |
| ggagtgacgt | cgaggcctct | gaggacttga | gctcagaggt | tgatcagatc | tgtgttgttc | 1680 |
| ctgtacagcg | tgtcaatagg | caagcatctc | atcggcttct | ggtccctaac | ccagcctgtc | 1740 |
| actgttgcat | caaacatgat | ggtatcaagc | aatgcacagt | gaggattcgc | agtggtttgt | 1800 |
| gcagcccct | tcttcttctt | ctttatgacc | aaacctttat | gtttggtgca | gagtagattg | 1860 |
| tatctctccc | agatctcatc | ctcaaaggtg | cgtgcttgct | cggcactgag | tttcacgtca | 1920 |
| agcacttttta | agtctcttct | cccatgcatt | tcgaacaaac | tgattatatc | atctgaacct | 1980 |
| tgagcagtga | aaaccatgtt | ttgaggtaaa | tgtctgatga | ttgaggaaat | caggcctggt | 2040 |
| tgggcatcag | ccaagtcctt | taaaagaaga | ccatgtgagt | acttgctttg | ctctttgaag | 2100 |
| gacttctcat | cgtggggaaa | tctgtaacaa | tgtatgtagt | tgcccgtgtc | aggctggtag | 2160 |
| atggccattt | ccaccggatc | atttggtgtt | ccttcaatgt | caatccatgt | ggtagctttt | 2220 |

```
gaatcaagca tctgaattga ggacacaaca gtgtcttctt tctccttagg gatttgttta    2280
aggtccggtg atcctccgtt tcttactggt ggctggatag cactcggctt cgaatctaaa    2340
tctacagtgg tgttatccca agccctccct tgaacttgag accttgagcc aatgtaaggc    2400
caaccatccc ctgaaagaca atcttgtat agtaaatttt cataaggatt tctctgtccg     2460
ggtgtagtgc tcacaaacat accttcacga ttctttattt gcaatagact ctttatgaga    2520
gtactaaaca tagaaggctt cacctggatg gtctcaagca tattgccacc atcaatcatg    2580
caagcagctg ctttgactgc tgcagacaaa ctgagattgt accctgagat gtttatggct    2640
gatggctcat tactaatgat ttttaggca ctgtgttgct gtgtgagttt ctctagatct      2700
gtcatgttcg ggaacttgac agtgtagagc aaaccaagtg cactcagcgc ttggacaaca    2760
tcattaagtt gttcaccccc ttgctcagtc atacaagcga tggttaaggc tggcattgat    2820
ccaaattgat tgatcaacaa tgtattatcc ttgatgtccc agatcttcac aaccccatct    2880
ctgttgcctg tgggtctagc attagcgaac cccattgagc gaaggatttc ggctcttgt     2940 tccaactgag tgtttgtgag attgcccca taaacaccag gctgagacaa actctcagtt     3000
ctagtgactt tctttcttaa cttgtccaaa tcagatgcaa gctccattag ctcctctttg    3060
gctaagcctc ccaccttaag cacattgtcc ctctggattg atctcatatt catcagagca    3120
tcaacctctt tgttcatgtc tcttaacttg gtcagatcag aatcagtcct tttatctttg    3180
cgcatcattc tttgaacttg agcaactttg tgaaagtcaa gagcagataa cagtgctctt    3240
gtgtccgaca acacatcagc cttcacagga tgggtccagt tggatagacc cctcctaagg    3300
gactgtaccc agcggaatga tgggatgttg tcagacattt tggggttgtt tgcacttcct    3360
ccgagtcagt gaagaagtga acgtacagcg tgatctagaa tcgcctagga tccactgtgc    3420
g                                                                    3421
```

```
<210> SEQ ID NO 7
<211> LENGTH: 9
<212> TYPE: PRT
<213> ORGANISM: nucleoprotein epitope

<400> SEQUENCE: 7

Ala Ser Asn Glu Asn Met Glu Thr Met
1               5

<210> SEQ ID NO 8
<211> LENGTH: 84
<212> TYPE: RNA
<213> ORGANISM: Pichinde mammarenavirus

<400> SEQUENCE: 8
cgcaccgggg auccuaggca ucuuuggguc acgcuucaaa uuugaccaau uugaacccag    60
cucaaguccu ggucaaaacu uggg                                           84

<210> SEQ ID NO 9
<211> LENGTH: 30
<212> TYPE: RNA
<213> ORGANISM: Pichinde mammarenavirus

<400> SEQUENCE: 9
cgcaccgagg auccuaggca uuucuugauc                                      30

<210> SEQ ID NO 10
<211> LENGTH: 51
<212> TYPE: RNA
```

```
<213> ORGANISM: Pichinde mammarenavirus

<400> SEQUENCE: 10
cgcaccgggg auccuaggca uaccuuggac gcgcauauua cuugaucaaa g         51

<210> SEQ ID NO 11
<211> LENGTH: 83
<212> TYPE: RNA
<213> ORGANISM: Pichinde mammarenavirus

<400> SEQUENCE: 11
cgcacagugg auccuaggcg auucuagauc acgcuguacg uucacuucuu cacugacucg    60
gaggaagugc aaacaacccc aaa                                           83

<210> SEQ ID NO 12
<211> LENGTH: 71
<212> TYPE: RNA
<213> ORGANISM: Pichinde mammarenavirus

<400> SEQUENCE: 12
accagggccc cugggcgcac cccccuccgg gggugcgccc gggggccccc ggccccaugg    60
ggccgguugu u                                                        71

<210> SEQ ID NO 13
<211> LENGTH: 75
<212> TYPE: RNA
<213> ORGANISM: Pichinde mammarenavirus

<400> SEQUENCE: 13
gcccuagccu cgacaugggc cucgacguca cuccccaaua ggggagugac gucgaggccu    60
cugaggacuu gagcu                                                    75

<210> SEQ ID NO 14
<211> LENGTH: 87
<212> TYPE: DNA
<213> ORGANISM: hepatitis delta virus ribozyme

<400> SEQUENCE: 14
agctctccct tagccatccg agtggacgac gtcctccttc ggatgcccag gtcggaccgc    60
gaggaggtgg agatgccatg ccgaccc                                       87
```

PICHINDE VIRUS REVERSE GENETICS SYSTEMS AND METHODS OF USE

CROSS-REFERENCE TO RELATED APPLICATIONS

This application is the § 371 U.S. National Stage of International Application No. PCT/US2015/051337, filed 22 Sep. 2015, which claims the benefit of U.S. Provisional Application Ser. No. 62/053,443, filed Sep. 22, 2014, which are incorporated by reference herein.

GOVERNMENT FUNDING

This invention was made with government support under AI083409 awarded by the National Institutes of Health. The government has certain rights in the invention.

SEQUENCE LISTING

This application contains a Sequence Listing electronically submitted to the United States Patent and Trademark Office via EFS-Web as an ASCII text file entitled "2015-09-22-SequenceListing_ST25.txt" having a size of 45 KB and created on Sep. 22, 2015. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein

BACKGROUND

Arenavirus family includes a group of bi-segmented enveloped RNA viruses with genomes encoding a total of four genes in opposite orientation (Buchmeier et al., 2007, p. 1791-1827. In Knipe D M, Howley P M (ed.), Fields Virology, 5th ed. Lippincott Williams & Wilkins, Philadelphia, Pa.). The Z protein produced from the large (L) genomic segment is a small RING-domain containing matrix protein that mediates virus budding and also regulates viral RNA synthesis. The large L protein (~200 kDa) encoded also on the L segment is the RNA-dependent RNA polymerase (RdRp) protein that is required for viral RNA synthesis. The glycoprotein (GPC) encoded on the small (S) segment is post-translationally processed into a stable signal peptide (SSP), the receptor-binding G1 protein, and the transmembrane G2 protein. The nucleoprotein (NP) of the S segment encapsidates viral genomic RNAs, is required for viral RNA synthesis, and also suppresses host innate immune responses.

Arenaviruses are zoonotic RNA viruses with rodents as their primary natural hosts (for a review, see McLay et al., 2014, J Gen Virol 95(Pt 1):1-15). Humans can be infected with arenaviruses through direct contact of skin lesions with rodent excretions, eating foods contaminated with rodent excretions, or inhalation of tainted aerosols. Only a few arenaviruses can cause diseases in humans (for a review, see McLay et al., 2013, Antiviral Res 97:81-92). For example, lymphocytic choriomeningitis virus (LCMV) can cause central nerve system diseases, whereas Lassa virus (LASV) and several other arenaviruses can cause hemorrhagic fevers that can potentially result in terminal shock and death. Limited therapeutic options are available for treating these viral infections. The only available antiviral drug (ribavirin) shows some beneficial effects but it has many side effects and must be administered soon after the infection when the disease is often mis-diagnosed as the symptoms are only flu-like and insidious.

Due to the high containment requirement (BSL-4) to work with pathogenic arenaviruses and the cost associated with working with non-human primates, only limited vaccine studies have been done. There are currently no vaccines for these pathogenic arenaviruses, except for the Candid #1 that is not FDA-approved but is available only for off-labeled usage against Junin virus, which causes Argentine hemorrhagic fever. Several safe and convenient systems have been developed to study arenavirus replication and pathogenesis in the conventional BSL-2 laboratory, such as the Pichinde virus model system (Lan et al., 2009, J Virol 83:6357-6362, Liang et al., 2009, Ann NY Acad Sci 1171 Suppl 1:E65-74, Kumar et al., 2012, Virology 433:97-103, Wang et al., 2012, J Virol 86:9794-9801, McLay et al., 2013, J Virol 87:6635-6643). Pichinde virus (PICV) was isolated from rice rats in Columbia. It does not cause disease in humans, but can cause hemorrhagic fever-like symptoms in guinea pigs and thus is an ideal surrogate model to study arenavirus-induced hemorrhagic fevers. Serological evidence suggests a very low seroprevalence in humans (2 out of 82 people living or working in close association with habitats of infected rodents and 6 out of 13 laboratory workers have shown anti-PICV serum positivity but no distinct illnesses (Trapido et al., 1971, Am J Trop Med Hyg 20:631-641, Buchmeier et al., 1974, Infect Immun 9:821-823). Therefore, there is little to no preexisting immunity against PICV in the general human population, in contrast to LCMV, a prototypic arenavirus, which shows 2-5% seroprevalence in humans.

SUMMARY OF THE APPLICATION

Provided herein is a genetically engineered Pichinde virus. In one embodiment, the virus includes three ambisense genomic segments. The first genomic segment includes a coding region encoding a Z protein and a coding region encoding a L RdRp protein. The second genomic segment includes a coding region encoding a nucleoprotein (NP) and a first restriction enzyme site. The third genomic segment includes a coding region encoding a glycoprotein and a second restriction enzyme site. In one embodiment, the NP protein includes an amino acid sequence having at least 80% identity to SEQ ID NO:3. In one embodiment, nucleoprotein includes at least one mutation that reduces the exoribonuclease activity of the nucleoprotein, wherein the mutation is selected from an aspartic acid at about amino acid 380, a glutamic acid at about amino acid 382, an aspartic acid at about amino acid 525, a histidine at about amino acid 520, and an aspartic acid at about amino acid 457, wherein the aspartic acid, the glutamic acid, or the histidine is substituted with any other amino acid. In one embodiment, the glycoprotein includes at least one mutation that alters the activity of the glycoprotein, wherein the mutation is selected from an asparagine at about amino acid 20 and an asparagine at about amino acid 404, and wherein the asparagine is substituted with any other amino acid. D, E, or H is substituted with any other amino acid.

In one embodiment, the second genomic segment includes a multiple cloning site, and the first restriction enzyme site is part of the multiple cloning site. The second genomic segment may further include a coding region encoding a first protein inserted at the first restriction site. In one embodiment, the third genomic segment includes a multiple cloning site, and the second restriction enzyme site is part of the multiple cloning site. In one embodiment, the third genomic segment may further include a coding region encoding a second protein inserted at the first restriction site. In one embodiment, the second genomic segment further includes a coding region encoding a first protein inserted at the first restriction site, and the third genomic segment further includes a coding region encoding a second protein inserted at the first restriction site. In one embodiment, the first protein and the second protein are selected from an antigen and a detectable marker. In one embodiment, the antigen is a protein expressed by a viral pathogen, a prokaryotic pathogen, or a eukaryotic pathogen. The first protein and the second protein may be the same or may be different.

Also provided herein is a collection of vectors. In one embodiment, the vectors are plasmids. In one embodiment, the collection includes a first vector encoding a first genomic segment including a coding region encoding a Z protein and a coding region encoding a L RdRp protein, wherein the first genomic segment is antigenomic, a second vector encoding a second genomic segment including a coding region encoding a nucleoprotein (NP) and a first restriction enzyme site, wherein the second genomic segment is antigenomic, and a third vector encoding a third genomic segment includes a coding region encoding a glycoprotein and a second restriction enzyme site, wherein the third genomic segment is antigenomic. In one embodiment, the NP protein includes an amino acid sequence having at least 80% identity to SEQ ID NO:3.

In one embodiment, the second genomic segment includes a multiple cloning site, and the first restriction enzyme site is part of the multiple cloning site. The second genomic segment may further include a coding region encoding a first protein inserted at the first restriction site. In one embodiment, the third genomic segment includes a multiple cloning site, and the second restriction enzyme site is part of the multiple cloning site. In one embodiment, the third genomic segment may further include a coding region encoding a second protein inserted at the first restriction site. In one embodiment, the second genomic segment further includes a coding region encoding a first protein inserted at the first restriction site, and the third genomic segment further includes a coding region encoding a second protein inserted at the first restriction site. In one embodiment, the first protein and the second protein are selected from an antigen and a detectable marker. In one embodiment, the antigen is a protein expressed by a viral pathogen, a prokaryotic pathogen, or a eukaryotic pathogen. The first protein and the second protein may be the same or may be different.

Further provided are methods. In one embodiment, a method includes making a genetically engineered Pichinde virus as described herein. The method includes introducing into a cell the collection of vectors described herein, and incubating the cells in a medium under conditions suitable for expression and packaging of the first, second, and third genomic segments into a virus particle. The method may also include isolating an infectious virus particle from the medium.

Also provided herein is a reverse genetics system for making a genetically engineered Pichinde virus, wherein the system includes three vectors. The first vector encodes a first genomic segment including a coding region encoding a Z protein and a coding region encoding a L RdRp protein, wherein the first genomic segment is antigenomic, the second vector encodes a second genomic segment including a coding region encoding a nucleoprotein (NP) and a first restriction enzyme site, wherein the second genomic segment is antigenomic, and the third vector encodes a third genomic segment includes a coding region encoding a glycoprotein and a second restriction enzyme site, wherein the third genomic segment is antigenomic. In one embodiment, the NP protein includes an amino acid sequence having at least 80% identity to SEQ ID NO:3.

In one embodiment, a method includes using a reverse genetics system, including introducing into a cell three vectors of genomic segments described herein, incubating the cell under conditions suitable for the transcription of the three genomic segments and expression of the coding regions of each genomic segment. In one embodiment, the method also includes isolating infectious virus particles produced by the cell, wherein each infectious virus particle includes the three genomic segments. In one embodiment, the introducing includes transfecting a cell with the three genomic segments. In one embodiment, the introducing includes contacting the cell with an infectious virus particle including the three genomic segments. In one embodiment, the cell is ex vivo, such as a vertebrate cell. In one embodiment, the vertebrate cell may be a mammalian cell, such as a human cell, or the vertebrate cell may be an avian cell, such as a chicken embryonic fibroblast.

In one embodiment, a method includes producing an immune response in a subject. The method includes administering to a subject an infectious virus particle described herein, wherein the second genomic segment includes a coding region encoding a first antigen, and the third genomic segment further includes a coding region encoding a second antigen. In one embodiment, the cell is ex vivo, such as a vertebrate cell. In one embodiment, the vertebrate cell may be a mammalian cell, such as a human cell, or the vertebrate cell may be an avian cell. The immune response may include a humoral immune response, a cell-mediated immune response, or a combination thereof. In one embodiment, the antigen is a protein expressed by a viral pathogen, a prokaryotic pathogen, or a eukaryotic pathogen, or a fragment thereof. The subject may have been exposed to, or is at risk of exposure to the viral pathogen, the prokaryotic pathogen, or the eukaryotic pathogen. In one embodiment, the administering includes administering at least two populations of infectious virus particles, wherein each population of infectious virus particle encodes a different antigen.

Also provided herein is an infectious virus particle as described herein, and a composition that includes an infectious virus particle described herein.

BRIEF DESCRIPTION OF THE FIGURES

FIG. 5. Generation of tri-segmented PICV carrying influenza HA or NP antigen.

FIG. 9. HAI titers induced by the rP18tri-GFP/HA virus via different routes of vaccination. IN, intranasal; IM, intramuscular; IP, intraperitoneal.

FIG. 13. Vaccine conferred long lasting immunity and protection. C57BL6 mice were challenged with $10LD_{50}$ A/PR/8 after 1 or 2 months of boosting with the rP18tri-GFP/HA vaccine vector. A. HI titres at day 14 and day 30 post prime (dpp), day 30 and day 60 post boost (dpb). B. Viral titre in lungs at 6 dpi. C. Percent weight loss. D. H&E stained lung sections.

Figure 15:
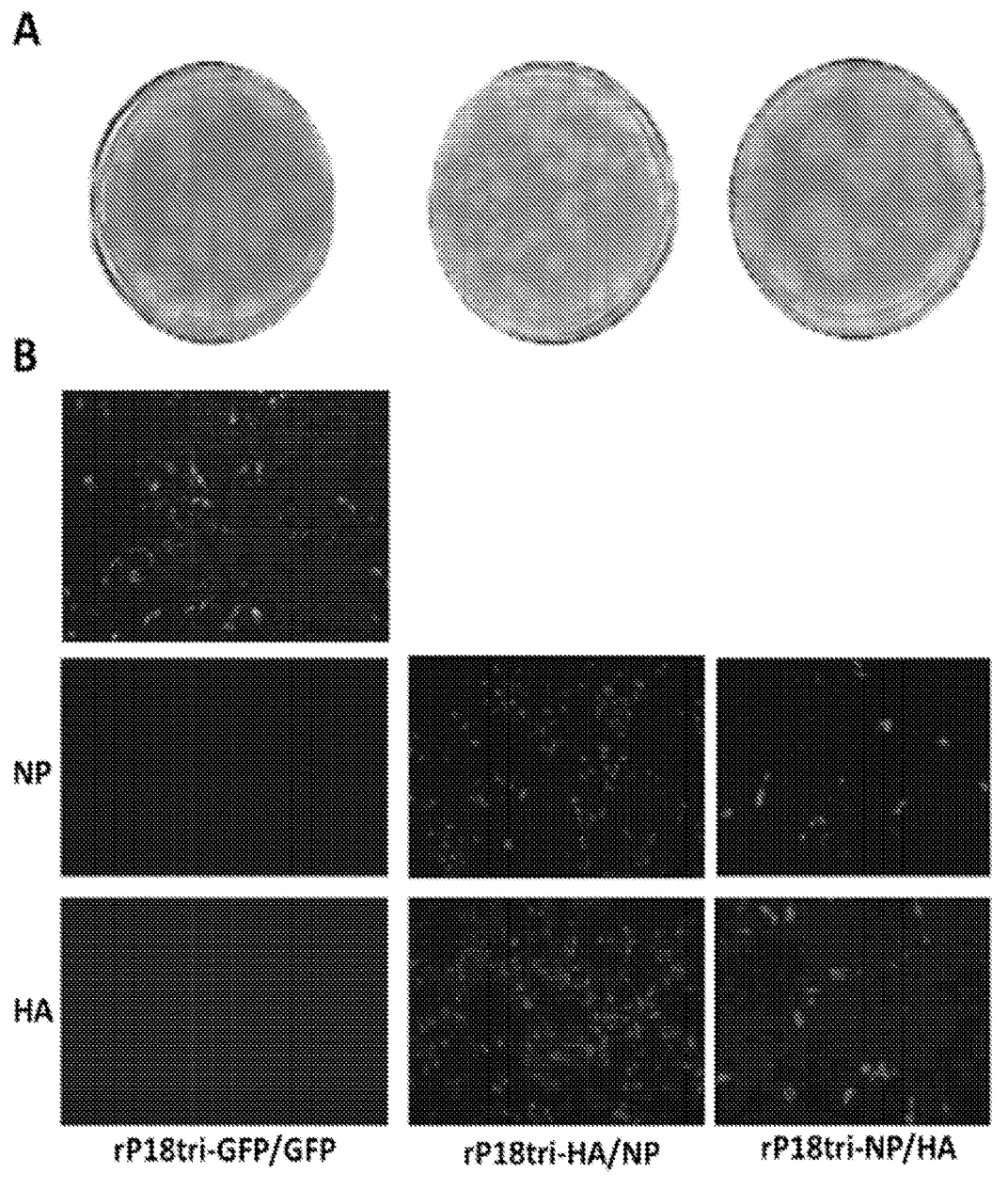

FIG. 15. Plaque size and expression of HA and NP from the rP18tri-HA/NP and the rP18tri-NP/HA. Titers and plaque formation on Vero cells (FIG. 15A), and expression level of the influenza viral protein antigens by rP18tri-GFP/GFP, rP18tri-HA/NP, and rP18tri-NP/HA (FIG. 15B).

FIG. 17. Protection conferred by the rP18tri-based vaccine expressing both influenza viral HA and NP. A. Stained lung sections from animals vaccinated with either a prime-boost of rP18tri-GFP/GFP, rP18tri-HA/NP or rP18tri-NP/HA. B. Virus titre in lungs. C. Percent weight loss after PR8 challenge.

FIG. 20. rP18tri vector induces stronger CTL responses after boosting

Body weight of each animal was monitored daily and normalized to day 0. The results shown are the average of the normalized body weight for each group.

Figure 23:
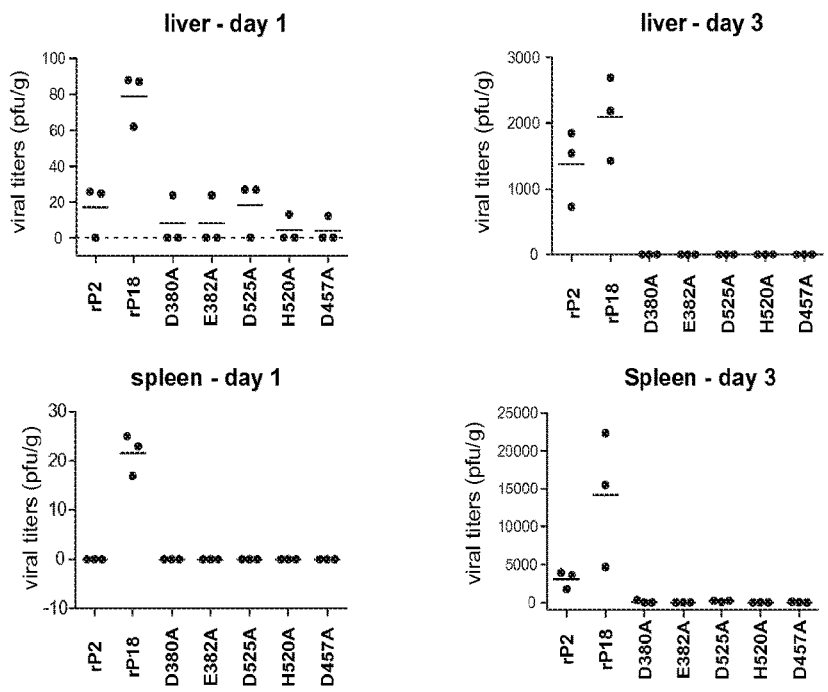
Figure 23:
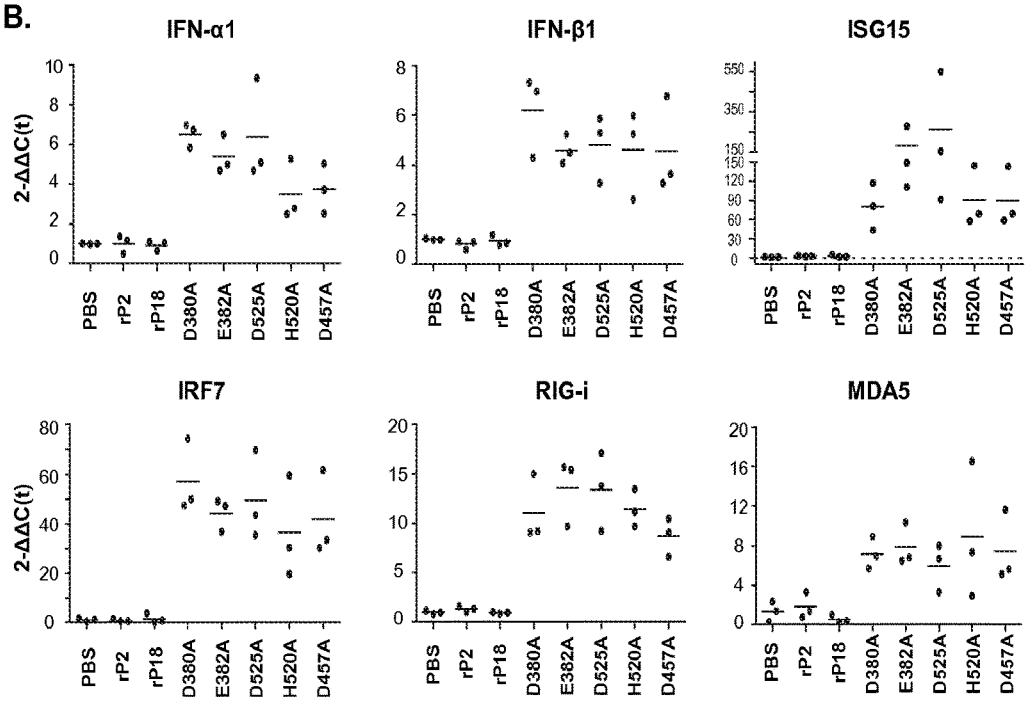

FIG. 23. The PICV NP RNase mutants induced strong IFN responses to block the establishment of virus infection. Guinea pigs were infected i.p. with $1\times10^4$ pfu of the respective recombinant viruses (n=3 animals per virus group) for 1 and 3 days. (A) Viral titers in the livers and spleens at 1 and 3 dpi. (B) The levels of type I IFNs and selective interferon-stimulating genes (ISGs) in the peritoneal cavity cells at day 1 were measured by qRT-PCR. Primer sequences will be provided upon request. Each dot represents a single animal. Statistical analyses were conducted by the student's t test.

Figure 24:
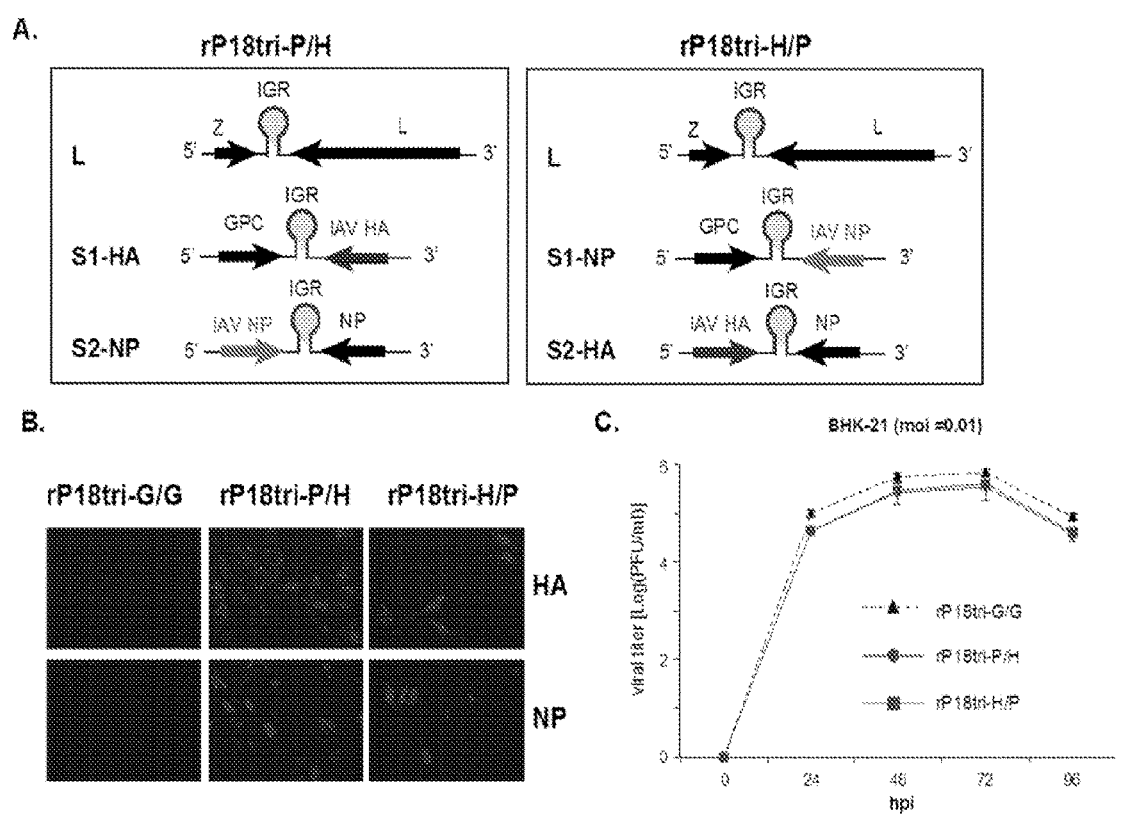

FIG. 24. Generation of rP18tri expressing dual antigens flu HA and NP. (A) Schematic diagram of rP18tri vectors expressing dual antigens HA and NP of influenza A virus (IAV) A/PR8 on S1 and S2 segments, rP18tri-P/H, and rP18tri-H/P. IGR, intergenic region. (B) The rP18tri dual antigen vectors express both HA and NP as shown by immunofluorescence assay (IFA). (C) Growth curve analysis of the recombinant viruses expressing the dual antigens in BHK-21 cells.

Figure 25:
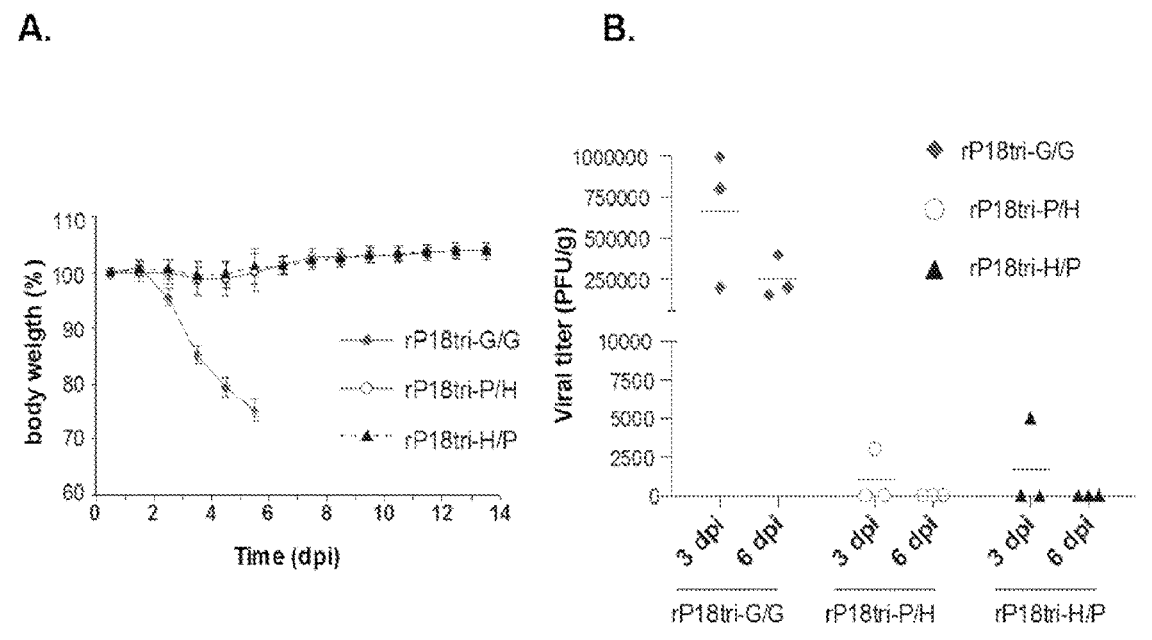

FIG. 25. The HA/NP dual antigen expressing vaccine vectors can induce protective immunity in mice. A group of C57BL6 mice (n=3) were given two doses of respective rP18tri vectors at $1\times10^4$ pfu and challenged intranasally (IN) with $10\times MLD_{50}$ (median lethal dose) of the mouse-adapted influenza A/PR8 virus. Body weight (A) and viral lung titers at 3 and 6 dpi (B) are shown.

Figure 26:
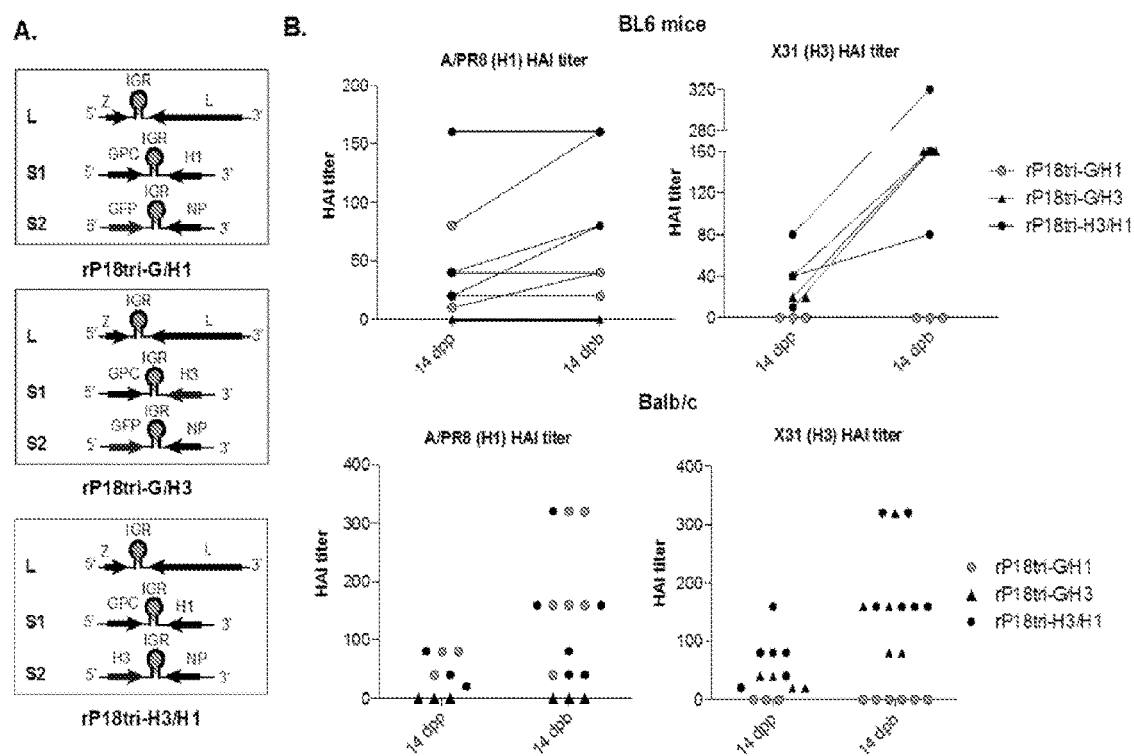

FIG. 26. The H1/H3 dual antigen vector induces balanced HA neutralizing antibodies. (A) Schematic diagram of rP18tri vectors expressing eGFP and H1 HA (rP18tri-G/H1), eGFP and H3 HA (rP18tri-G/H3), and H1 and H3 (rP18tri-H3/H1). (B) The rP18tri-H3/H1 induces balanced neutralizing antibodies against both H1 and H3 HA subtypes. Groups of C57BL6 (top panels) and Balb/c mice (bottom panels) were immunized with the respective rP18tri vectors (n>=3) twice through the IM route. Blood collected at 14 days post prime and post boost were quantified for the levels of neutralizing antibodies against A/PR8 (H1N1) and A/x31 (H3N2) by HAI assay.

Figure 27:
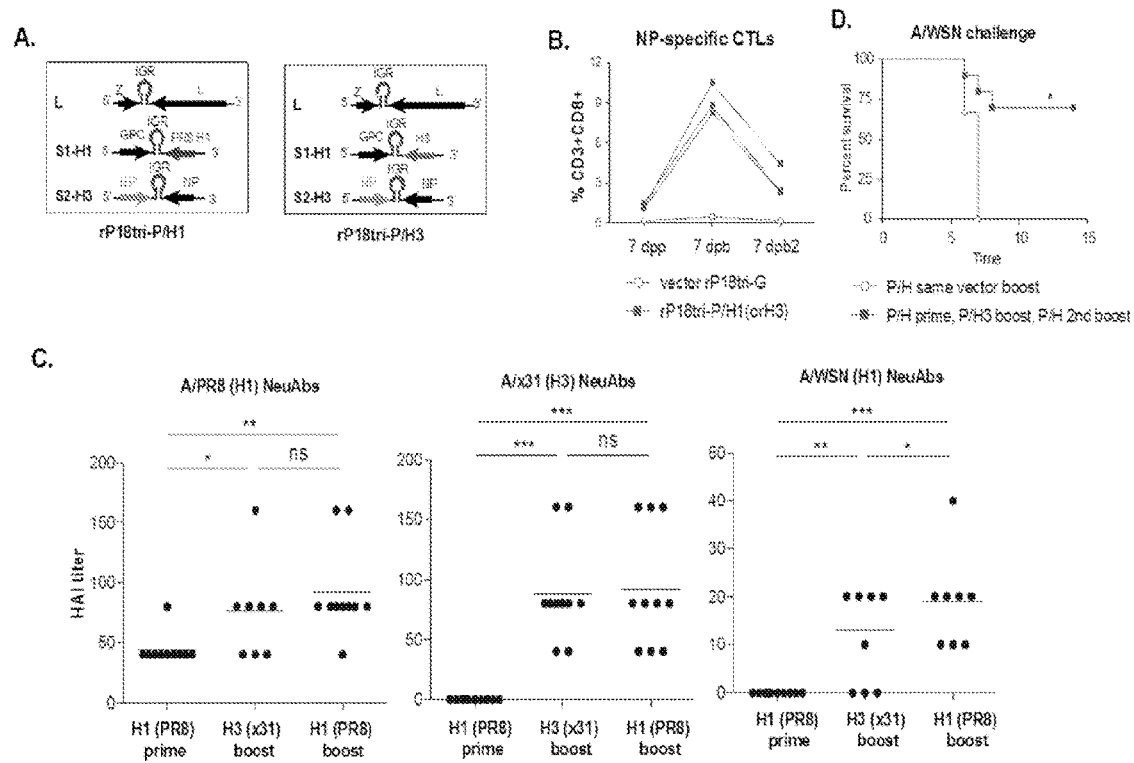

FIG. 27. Induction of heterosubtypic neutralizing antibodies by a prime-and-boost strategy with different HA subtypes. (A) Schematic diagram of rP18tri vectors expressing A/PR8 NP together with either H1 HA from A/PR8 (rP18tri-P/H1) or H3 HA from A/x31 (rP18tri-P/H3). (B) NP-specific CTLs increased upon a booster dose. C57BL6 mice were primed with rP18tri-P/H1, boosted with rP18tri-P/H3, and boosted again with rP18tri-P/H1, at a 14-day interval. NP-specific effector T cells 7 days after prime (dpp), after the $1^{st}$ boost (dpb), and after the $2^{nd}$ boost (dpb2) were quantified by the established NP tetramer analysis. (C) Neutralizing antibodies against A/PR8 (H1), A/x31 (H3), and A/WSN (heterosubtypic H1) after prime and boosts were quantified by HAI assay.

Figure 28:
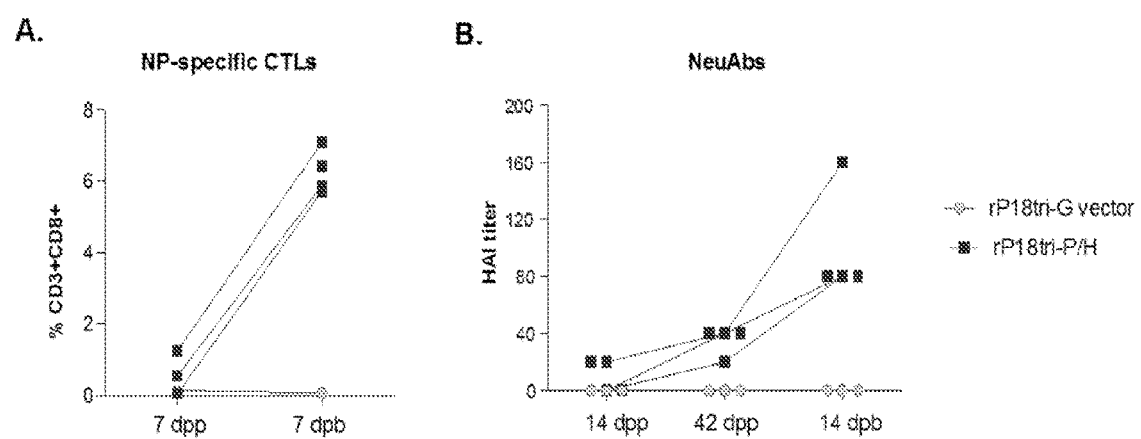

FIG. 28. The rP18tri vector can induce both humoral and T cell responses through oral route. Groups of BL6 mice were immunized twice with either rP18tri-G (n=3) vector or rP18tri-P/H (n=4) through oral gavage. NP-specific effector T cells (A) and H1-specific neutralizing antibodies (B) at different days after prime or boost are shown. dpp, days post-prime; dpb, days post-boost.

Figure 29:
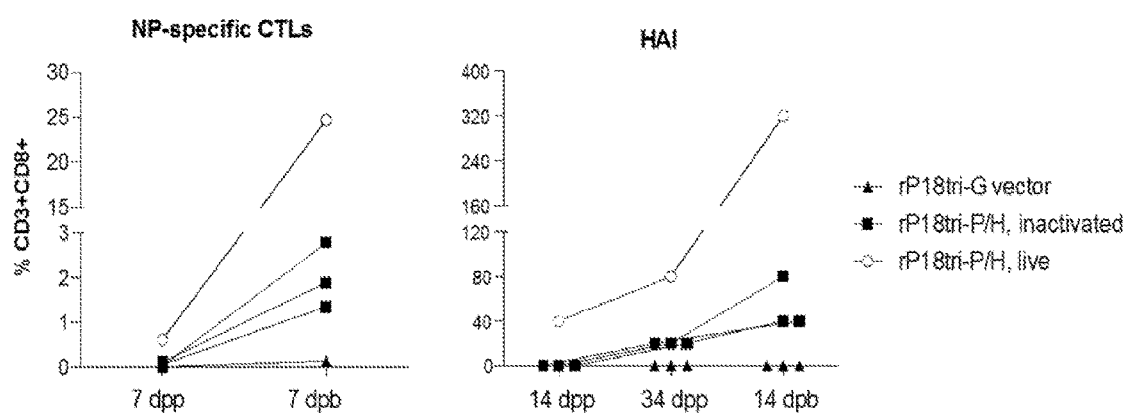

FIG. 29. Inactivated rP18tri vector can induce both humoral and T cell responses. Groups of C57BL6 mice were immunized twice with rP18tri-G vector (n=3), hydrogen peroxide-inactivated rP18tri-P/H (n=3), and live rP18tri-P/H (n=1), respectively. NP-specific effector T cells (left panel) and neutralization antibodies (right) at different days after immunization are shown. dpp, days post-prime; dpb, days post-boost.

Figure 30:
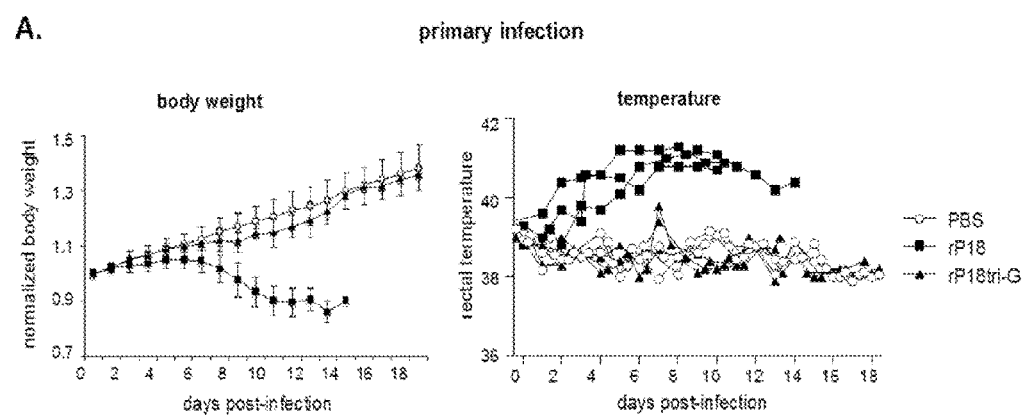
Figure 30:
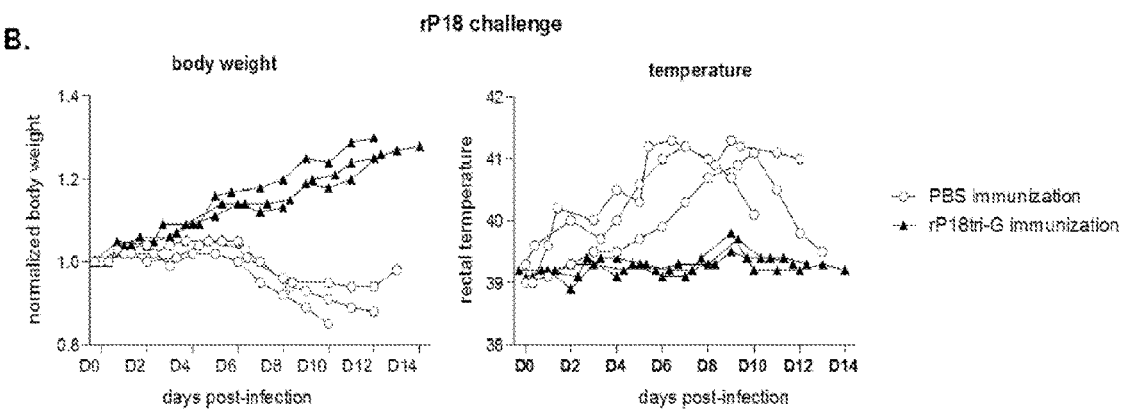

FIG. 30. The rP18tri vector does not show virulence in guinea pigs and can protect the animals from a lethal challenge with the WT rP18 virus. (A) The rP18tri-G does not cause virulent infections in guinea pigs. Groups of Hartley guinea pigs (n=3) were mock infected (PBS) or infected with WT rP18 ($1\times10^4$ pfu) or rP18tri-G ($1\times10^6$ pfu) through the IP route. Body weight was monitored daily and normalized to day 0 (left panel). Rectal temperature is shown on the right. (B) The rP18tri-G-immunized guinea pigs were protected from lethal rP18 challenge. Groups of guinea pigs (n=3) were immunized with either PBS or rP18tri-G at $1\times10^4$ pfu through the IP route and, 14 days later, challenged with $1\times10^4$ pfu of WT rP18 virus. Normalized body weight (left panel) and rectal temperature (right panel) are shown. Temperature above 39.5° C. is considered to be feverish.

DETAILED DESCRIPTION OF ILLUSTRATIVE EMBODIMENTS

Provided herein is a reverse genetics system for producing genetically modified Pichinde virus. The genetically modified Pichinde virus-based reverse genetics system described herein has multiple advantages over other arenavirus systems. Pichinde virus is not known to cause disease in humans, and there is evidence that Pichinde virus can cause asymptomatic human infections in a laboratory setting. For instance, 46% of laboratory personnel working with the virus are serum positive but do not show a distinct illness (Buchmeier et al., 2007, Arenaviridae: the viruses and their replication. In: Knipe and Howley (eds), Fields Virology. 5th ed. Philadelphia, Pa.: Lippincott Williams & Wilkins. pp. 1791-1827). The modified Pichinde virus described herein is further attenuated, compared to the parental virus used in the human-infection study reported by Buchmeier et al. The modified Pichinde virus is genetically stable through serial passages in cell cultures. General human populations are not known to have prior exposure to Pichinde virus, which makes it an ideal vector for vaccine development due to the lack of pre-existing immunity against this Pichinde virus vector. As used herein, "genetically modified" and "genetically engineered" refers to a Pichinde virus which has been modified and is not found in any natural setting. For example, a genetically modified Pichinde virus is one into which has been introduced an exogenous polynucleotide, such as a restriction endonuclease site. Another example of a genetically modified Pichinde virus is one which has been modified to include three genomic segments.

The reverse genetics system for this modified Pichinde virus includes two to three genomic segments. The first genomic segment includes two coding regions, one that encodes a Z protein and a second that encodes a RNA-dependent RNA polymerase (L RdRp). The second genomic segment includes a coding region that encodes a nucleoprotein (NP), and may include at least one restriction enzyme site, such as a multiple cloning site. The third genomic segment includes a coding region that encodes a glycoprotein, and may include at least one restriction enzyme site, such as a multiple cloning site. A "coding region" is a nucleotide sequence that encodes a protein and, when placed under the control of appropriate regulatory sequences expresses the encoded protein. As used herein, the term "protein" refers broadly to a polymer of two or more amino acids joined together by peptide bonds. The term "protein" also includes molecules which contain more than one protein joined by disulfide bonds, ionic bonds, or hydrophobic interactions, or complexes of proteins that are joined together, covalently or noncovalently, as multimers (e.g., dimers, tetramers). Thus, the terms peptide, oligopeptide, and polypeptide are all included within the definition of protein and these terms are used interchangeably. It should be understood that these terms do not connote a specific length of a polymer of amino acids, nor are they intended to imply or distinguish whether the protein is produced using recombinant techniques, chemical or enzymatic synthesis, or is naturally occurring.

The Z protein, L RdRp, NP protein, and glycoprotein are those encoded by a Pichinde virus. The Z protein is a small RING-domain containing matrix protein that mediates virus budding and also regulates viral RNA synthesis. One example of a Z protein from a Pichinde virus is the sequence available at Genbank accession number ABU39910.1 (SEQ ID NO:1). The L RdRp protein is a RNA-dependent RNA polymerase that is required for viral DNA synthesis. One example of a L RdRp protein from a Pichinde virus is the sequence available at Genbank accession number ABU39911.1 (SEQ ID NO:2). The NP protein encapsidates viral genomic RNAs, is required for viral RNA synthesis, and also suppresses host innate immune responses. One example of a NP protein from a Pichinde virus is the sequence available at Genbank accession number ABU39909.1 (SEQ ID NO:3). The glycoprotein is post-translationally processed into a stable signal peptide (SSP), the receptor-binding G1 protein, and the transmembrane G2 protein. One example of a glycoprotein from a Pichinde virus is the sequence available at Genbank accession number ABU39908.1 (SEQ ID NO:4).

Other examples of Z proteins, L RdRp proteins, NP proteins, and glycoprotein include proteins having structural similarity with a protein that is encoded by a Pichinde virus, for instance, SEQ ID NO:1, 2, 3, and/or 4. Structural similarity of two polypeptides can be determined by aligning the residues of the two polypeptides (for example, a candidate polypeptide and a reference polypeptide described herein) to optimize the number of identical amino acids along the lengths of their sequences; gaps in either or both sequences are permitted in making the alignment in order to optimize the number of identical amino acids, although the amino acids in each sequence must nonetheless remain in their proper order. A reference polypeptide may be a polypeptide described herein, such as SEQ ID NO:1, 2, 3, or 4. A candidate polypeptide is the polypeptide being compared to the reference polypeptide. A candidate polypeptide may be isolated, for example, from a cell of an animal, such as a mouse, or can be produced using recombinant techniques, or chemically or enzymatically synthesized. A candidate polypeptide may be inferred from a nucleotide sequence present in the genome of a Pichinde virus.

Unless modified as otherwise described herein, a pairwise comparison analysis of amino acid sequences can be carried out using the Blastp program of the blastp suite-2 sequences search algorithm, as described by Tatiana et al., (*FEMS Microbiol Lett,* 174, 247-250 (1999)), and available on the National Center for Biotechnology Information (NCBI) website. The default values for all blastp suite-2 sequences search parameters may be used, including general parameters: expect threshold=10, word size=3, short queries=on; scoring parameters: matrix=BLOSUM62, gap costs=existence:11 extension:1, compositional adjustments=conditional compositional score matrix adjustment. Alternatively, polypeptides may be compared using the BESTFIT algorithm in the GCG package (version 10.2, Madison Wis.).

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a polypeptide described herein may be selected from other members of the class to which the amino acid belongs. For example, it is known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH2.

The skilled person will recognize that the Z protein depicted at SEQ ID NO:1 can be compared to Z proteins from other arenaviruses, including Lassa virus (073557.4), LCMV Armstrong (AAX49343.1), and Junin virus (NP_899216.1) using readily available algorithms such as ClustalW to identify conserved regions of Z proteins. ClustalW is a multiple sequence alignment program for nucleic acids or proteins that produces biologically meaningful multiple sequence alignments of different sequences (Larkin et al., 2007, ClustalW and ClustalX version 2, Bioinformatics, 23(21):2947-2948). Using this information the skilled person will be able to readily predict with a reasonable expectation that certain conservative substitutions to an Z protein such as SEQ ID NO:1 will not decrease activity of the polypeptide.

The skilled person will recognize that the L RdRp protein depicted at SEQ ID NO:2 can be compared to L RdRp proteins from other arenaviruses, including Lassa virus (AAT49002.1), LCMV Armstrong (AAX49344.1), and Junin virus (NP_899217.1) using readily available algorithms such as ClustalW to identify conserved regions of L RdRp proteins. Using this information the skilled person will be able to readily predict with a reasonable expectation that certain conservative substitutions to an L RdRp protein such as SEQ ID NO:2 will not decrease activity of the polypeptide.

The skilled person will recognize that the NP protein depicted at SEQ ID NO:3 can be compared to NP proteins from other arenaviruses, including Lassa virus (P13699.1), LCMV Armstrong (AAX49342.1), and Junin virus (NP_899219.1) using readily available algorithms such as ClustalW to identify conserved regions of NP proteins. Using this information the skilled person will be able to readily predict with a reasonable expectation that certain conservative substitutions to a NP protein such as SEQ ID NO:3 will not decrease activity of the polypeptide.

The skilled person will recognize that the glycoprotein depicted at SEQ ID NO:4 can be compared to glycoproteins from other arenaviruses, including Lassa virus (P08669), LCMV Armstrong (AAX49341.1), and Junin virus (NP_899218.1) using readily available algorithms such as ClustalW to identify conserved regions of glycoproteins. Using this information the skilled person will be able to readily predict with a reasonable expectation that certain conservative substitutions to a glycoprotein such as SEQ ID NO:4 will not decrease activity of the polypeptide.

Thus, as used herein, a Pichinde virus Z protein, L RdRp protein, an NP protein, or a glycoprotein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to a reference amino acid sequence. Alternatively, as used herein, a Pichinde virus Z protein, L RdRp protein, an NP protein, or a glycoprotein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to a reference amino acid sequence. Unless noted otherwise, "Pichinde virus Z protein," "Pichinde virus L RdRp protein," "Pichinde virus NP protein," and "Pichinde virus glycoprotein" refer to a protein having at least 80% amino acid identity to SEQ ID NO:1, SEQ ID NO:2, SEQ ID NO:3, and SEQ ID NO:4, respectively.

A Pichinde virus Z protein, L RdRp protein, an NP protein, or a glycoprotein having structural similarity the amino acid sequence of SEQ ID NO:1, 2, 3, or 4, respectively, has biological activity. As used herein, "biological activity" refers to the activity of Z protein, L RdRp protein, an NP protein, or a glycoprotein in producing an infectious virus particle. The biological role each of these proteins play in the biogenesis of an infectious virus particle is known, as are assays for measuring biological activity of each protein.

In one embodiment, the NP protein may include one or more mutations. A mutation in the NP protein may result in a NP protein that continues to function in the production of infectious viral particles, but has a decreased ability to suppress the production of certain cytokines by a cell infected with a Pichinde virus. A Pichinde virus that has decreased ability to suppress cytokine production is expected to be useful in enhancing an immunological response to an antigen encoded by the virus. Examples of mutations include the aspartic acid at residue 380, the glutamic acid at residue 382, the aspartic acid at residue 457, the aspartic acid at residue 525, and the histidine at residue 520. A person of ordinary skill in the art recognizes that the precise location of these mutations can vary between different NP proteins depending upon the presence of small insertions or deletions in the NP protein, thus the precise location of a mutation is approximate, and can vary by 1, 2, 3, 4, or 5 amino acids.

In one embodiment, the mutation in the NP protein may be the replacement of the aspartic acid, glutamic acid, or histidine at residues 380, 382, 457, 525, and/or 520 with any other amino acid. In one embodiment, the mutation may be the conservative substitution of the aspartic acid, glutamic acid, or histidine at residues 380, 382, 457, 525, and/or 520. In one embodiment, the mutation may be the replacement of the aspartic acid, glutamic acid, or histidine at residues 380, 382, 457, 525, and/or 520 with a glycine or an alanine. In one embodiment, the NP protein may include a mutation at one, two, three, or four of the residues 380, 382, 457, 525, or 520, and in one embodiment the NP protein may include a mutation at all five residues.

In one embodiment, the glycoprotein may include one or more mutations. A mutation in the glycoprotein may result in a glycoprotein that impairs virus spreading in vivo. Examples of mutations include the asparagine at residue 20, and/or the asparagine at residue 404. A person of ordinary skill in the art recognizes that the precise location of these mutations can vary between different glycoproteins depending upon the presence of small insertions or deletions in the glycoprotein, thus the precise location of a mutation is approximate, and can vary by 1, 2, 3, 4, or 5 amino acids.

In one embodiment, the mutation in the glycoprotein may be the replacement of the asparagine residue 20 and/or 404 with any other amino acid. In one embodiment, the mutation may be the conservative substitution of the asparagine residue 20 and/or 404. In one embodiment, the mutation may be the replacement of the asparagine residue 20 and/or 404 with a glycine or an alanine.

Proteins as described herein also may be identified in terms the polynucleotide that encodes the protein. Thus, this disclosure provides polynucleotides that encode a protein as described herein or hybridize, under standard hybridization conditions, to a polynucleotide that encodes a protein as described herein, and the complements of such polynucleotide sequences. As used herein, the term "polynucleotide" refers to a polymeric form of nucleotides of any length, either ribonucleotides or deoxynucleotides, and includes both double- and single-stranded DNA and RNA. A polynucleotide may include nucleotide sequences having different functions, including for instance coding sequences, and non-coding sequences such as regulatory sequences. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment. An example of a polynucleotide is a genomic segment.

An example of a polynucleotide encoding a Z protein is the nucleotides 85-372 of the sequence available at Genbank accession number EF529747.1 (SEQ ID NO:5), an example of a polynucleotide encoding an L RdRp protein is the complement of nucleotides 443-7027 of the sequence available at Genbank accession number EF529747.1 (SEQ ID NO:5), an example of a polynucleotide encoding an NP protein is the complement of nucleotides 1653 . . . 3338 of the sequence available at Genbank accession number EF529746.1 (SEQ ID NO:6), and an example of a polynucleotide encoding a glycoprotein protein is the nucleotides 52-1578 of the sequence available at Genbank accession number EF529746.1 (SEQ ID NO:6). It should be understood that a polynucleotide encoding a Z protein, an L RdRp protein, an NP protein, or a glycoprotein represented by SEQ ID NO:1, 2, 3, or 4, respectively, is not limited to the nucleotide sequence disclosed at SEQ ID NO:5 or 6, but also includes the class of polynucleotides encoding such proteins as a result of the degeneracy of the genetic code. For example, the naturally occurring nucleotide sequence SEQ ID NO:5 is but one member of the class of nucleotide sequences encoding a protein having the amino acid sequence SEQ ID NO:1 and a protein having the amino acid sequence SEQ ID NO:2. The class of nucleotide sequences encoding a selected protein sequence is large but finite, and the nucleotide sequence of each member of the class can be readily determined by one skilled in the art by reference to the standard genetic code, wherein different nucleotide triplets (codons) are known to encode the same amino acid.

As used herein, reference to a polynucleotide as described herein and/or reference to the nucleic acid sequence of one or more SEQ ID NOs can include polynucleotides having a sequence identity of at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an identified reference polynucleotide sequence.

In this context, "sequence identity" refers to the identity between two polynucleotide sequences. Sequence identity is generally determined by aligning the bases of the two polynucleotides (for example, aligning the nucleotide sequence of the candidate sequence and a nucleotide sequence that includes, for example, a nucleotide sequence that encodes a protein of SEQ ID NO:1, 2, 3, or 4) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate sequence is the sequence being compared to a known sequence—e.g., a nucleotide sequence that includes the appropriate nucleotide sequence selected from, for example, SEQ ID NO:5 or 6. For example, two polynucleotide sequences can be compared using the Blastn program of the BLAST 2 search algorithm, as described by Tatiana et al., *FEMS Microbiol Lett.*, 1999; 174: 247-250, and available on the world wide web at ncbi.nlm.nih.gov/BLAST/. The default values for all BLAST 2 search parameters may be used, including reward for match=1, penalty for mismatch=-2, open gap penalty=5, extension gap penalty=2, gap x_dropoff=50, expect=10, wordsize=11, and filter on.

In one embodiment, the second and/or third genomic segments may each independently include a "multiple cloning site" with one restriction site or more than one restriction site.

In one embodiment, the second and/or third genomic segments may each independently include an additional coding region that encodes a protein, such as an antigen. Thus, the second genomic segment includes the coding region encoding the nucleoprotein and may include a second coding region that encodes an antigen. Likewise, the third genomic segment includes the coding region encoding the glycoprotein and may include a second coding region that encodes an antigen. The second and third genomic segments may encode the same antigen or different antigens. In both the second genomic segment and the third genomic segment this second coding region may be inserted into a restriction site present, such as a restriction site present in a multiple cloning site. The second coding region that may be present on the second genomic segment and/or the third genomic segment is not intended to be limiting.

In one embodiment, the second coding region may encode a protein that is useful as an antigen that can elicit an immune response in a subject. Examples 1, 2, and 3 show the use of influenza nucleoproteins and influenza hemagglutinins as model antigens to demonstrate the effectiveness of the reverse genetics systems and viruses disclosed herein, and accordingly the identity of the antigen is not intended to be limiting. An example of an antigen is a full length protein encoded by a prokaryotic cell, a eukaryotic cell (including, for instance a fungus, yeast, or protozoan) or a virus, or a fragment thereof. In one embodiment, the protein may be one that is naturally expressed by a pathogen, such as a viral pathogen, a prokaryotic pathogen, or a eukaryotic pathogen. Antigenic proteins encoded by a prokaryotic cell, a eukaryotic cell, or a virus are known to the skilled person in the art. Another example of an antigen is a protein engineered to include one or more epitopes. In one embodiment, the protein may be one that is expressed by a tumor cell or is present in a tumor environment.

Examples of prokaryotic pathogens from which an antigen may be obtained include gram negative pathogens and gram positive pathogens. Examples of gram negative pathogens include enteropathogens, such as members of the family Enterobacteriaceae, including members of the family Enterobacteriaceae that are members of the tribe Escherichieae or Salmonelleae. Examples of enteropathogens include members of the family Enterobacteriaceae, members of the family Vibrionaceae (including, for instance, *Vibrio cholerae*), and *Campylobacter* spp. (including, for instance, *C. jejuni*). Examples of preferred members of the family Enterobacteriaceae include, for instance, *E. coli, Shigella* spp., *Salmonella* spp., *Proteus* spp., *Klebsiella* spp. (for instance, *K. pneumoniae*), *Serratia* spp., and *Yersinia* spp. Examples of strains of *E. coli* include, for example, *E. coli* scrotypes O1a, O2a, O78, and O157, different O:H serotypes including 0104, 0111, 026, 0113, 091, hemolytic strains of enterotoxigenic *E. coli* such as K88+, F4+, F18ab+, and F18ac+, and non-hemolytic strains such as 987P, F41, and K99. As used herein, the term "strain" refers to members of a species of microbe where the members have different genotypes and/or phenotypes. Other examples of *E. coli* include five categories of diarrheagenic *Escherichia coli* that cause foodborne and waterborne diseases in humans: the enteropathogenic (EPEC), enterohemorrhagic (EHEC), enterotoxigenic (ETEC), enteroinvasive (EIEC) and enteroaggregative (EAEC) strains. Other gram negative microbes include members of the family Pasteurellaceae, preferably *Pasturella* spp., such as *P. multocida*, and *Mannheimia haemolytica*, and members of the family Pseudomonadaceae, such as *Pseudomonas* spp., including *P. aeruginosa*. Yet other gram negative microbes include *Bordetella* spp., *Burkholderia* spp., *Chlamydia* spp., *Enterobacter* spp., *Helobacter* spp., *Histophilus* spp., *Moraxella* spp., *Legionella* spp., *Leptospiria* spp., *Rickettsia* spp., *Treponnema* spp., *Neisseria* spp., *Actinobacillus* spp., *Haemophilus* spp., *Myxcobacteria* spp., *Sporocytophaga* spp., *Chondrococcus* spp., *Cytophaga* spp., *Flexibacter* spp., *Flavobacterium* spp., *Aeromonas* spp. Examples of *Yersinia* spp. include *Y. pestis, Y. pseudotuberculosis*, and *Y. enterocolitica*. Examples of *Fusobacterium* spp. belonging to the family Fusobacteriaceae include *F. necrophorum* (including subspecies *F. necrophorum* subsp. *necrophorum* and *F. necrophorum* subsp. *funduliforme*), *F. nucleatum, F. canifelinum, F. gonidiaformans, F. mortiferum, F. naviforme, F. necrogenes, F. russii, F. ulcerans*, and *F. variu.*

Examples of gram-positive pathogens include members of the family Micrococcaceae, including *Staphylococcus* spp., such as *S. aureus*. Other gram positive pathogens include members of the family Deinococcaceae, such as *Streptococcus agalactiae, Streptococcus uberis, Streptococcus bovis, Streptococcus equi, Streptococcus zooepidemicus*, and *Streptococcus dysgalatiae*. Other gram positive microbes from which an antigen may be obtained include *Bacillus* spp., *Clostridium* spp., *Corynebacterium* spp., *Erysipelothrix* spp., *Listeria* spp., *Mycobacterium* spp., Other gram positive pathogens include members of the Corynebacteriaceae, Enterococcaceae, Micrococcaceae, Mycobacteriaceae, Nocardiaceae, and Peptococcaceae, which include such bacterial species as *Actinomyces* spp., *Bifidobacterium* spp., *Enterococcus* spp., *Eubacterium* spp., *Kytococcus* spp., *Lactobacillus* spp., *Micrococcus* spp., *Mobiluncus* spp., *Mycobacteria* spp., *Peptostreptococcus* spp., and *Propionibacterium* spp., *Gardnerella* spp., *Mycoplasma, Norcardia* spp., *Streptomyces* spp., *Borrelia* spp., and *Bacillus* spp.

Examples of pathogenic protozoa include intestinal protozoa, urogenital protozoa, Systemic protozoa, and extraintestinal protozoa. Specific examples include, but are not limited to, e.g. Entamoeba histolytica, Giardia lamblia, Cryptosporidium parvum, Cystoisospora belli, Cyclospora cayetanensis, members of the phylum Microsporidia, Trichomonas vaginalis, Plamodium falciparum, Toxoplasma gondii, members of the subclass Coccidiosis such as members of the genus *Eimeria*, including *E. acervulina., E. necatrix* and *E. tenella, Nematodes, Trematodes*, and *Cestodes.*

Examples of viral pathogens include, but are not limited to members of the family Rhabdoviridae (including Vesicular stomatitis virus VSV), members of the genus *Aphthovirus* (including Foot-and-mouth disease virus FMDV), members of the genus *Pestivirus* (including Bovine viral diarrhea virus), members of the family Arterivirus (including porcine reproductive and respiratory syndrome virus PRRSV), Coronaviruses (including Porcine Epidemic Diarrhea virus EPDV, SARS-CoV, MERS-CoV), members of the genus *Torovirus* (including Equine torovirus), members of the family Orthomyxoviridae (including influenza virus), members of the family Reoviridae (including rotavirus, Bluetongue disease virus, avian reoviruses), members of the family Circovirus, members of the family Herpesviridae, members of the family Retroviridae (including HIV, FIV, SIV, ALV, BLV, RSV), members of the Asfariridae family (including African swine fever virus), members of the genus *Flavivirus* (including Dengue virus, Yellow fever virus), members of the family Paramyxoviridae (including Newcastle disease virus and Respiratory syncytial virus RSV), as well as members of the genus arenavirus (including members of the LCMV-Lassa virus (Old World) complex and the Tacaribe virus (New World) complex). Specific non-limiting examples of members of the genus arenavirus include Lymphocytic choriomeningitis virus, Pichinde virus, Lassa virus, Mopeia virus, Junin virus, Guanarito virus, Lujo virus, Machupo virus, Sabia virus, and Whitewater Arroyo virus.

In one embodiment, the protein encoded by the second coding region may be from an influenza virus, such as a nucleoprotein, a hemagglutinin, or a portion thereof. The nucleoprotein may be of any subtype, including but not limited to, A/PR8 NP (e.g., Genbank accession number NP_040982.1). The hemagglutinin may be of any subtype, including but not limited to, H1 and H3.

The protein encoded by the second coding region may be one that results in a humoral immune response, a cell-mediated immune response, or a combination thereof. In one embodiment, the protein encoded by the second coding region of the second and third genomic segments is at least 6 amino acids in length. The antigen may be heterologous to the cell in which the coding region is expressed. The nucleotide sequence of a second coding region present on a second and third genomic segment and encoding the antigen can be readily determined by one skilled in the art by reference to the standard genetic code. The nucleotide sequence of a second coding region present on a second and third genomic segment and encoding the antigen may be modified to reflect the codon usage bias of a cell in which the antigen will be expressed. The usage bias of nearly all cells in which a Pichinde virus would be expressed is known to the skilled person.

In one embodiment, the second coding region may encode a protein that is useful as a detectable marker, e.g., a molecule that is easily detected by various methods. Examples include fluorescent polypeptides (e.g., green, yellow, blue, or red fluorescent proteins), luciferase, chloramphenicol acetyl transferase, and other molecules (such as c-myc, flag, 6×his, HisGln (HQ) metal-binding peptide, and V5 epitope) detectable by their fluorescence, enzymatic activity or immunological properties.

When the second and/or third genomic segments include a coding region that encodes an antigen, the maximum size in nucleotides of the coding region(s) is determined by considering the total size of the second genomic segment and the third genomic segment. The total size of the two genomic segments may be no greater than 3.4 kilobases (kb), no greater than 3.5 kb, no greater than 3.6 kb, no greater than 3.7 kb, no greater than 3.8 kb, no greater than 3.9 kb, no greater than 4.0 kb, no greater than 4.1 kb, no greater than 4.2 kb, no greater than 4.3 kb, no greater than 4.4 kb, or no greater than 4.5 kb.

Pichinde virus is an arenavirus, and one characteristic of an arenavirus is an ambisense genome. As used herein, "ambisense" refers to a genomic segment having both positive sense and negative sense portions. For example, the first genomic segment of a Pichinde virus described herein is ambisense, encoding a Z protein in the positive sense and encoding a L RdRp protein in the negative sense. Thus, one of the two coding regions of the first genomic segment is in a positive-sense orientation and the other is in a negative-sense orientation. When the second and/or the third genomic segment includes a second coding region encoding an antigen, the coding region encoding the antigen is in a negative-sense orientation compared to the NP protein of the second genomic segment and to the glycoprotein of the third genomic segment.

Each genomic segment also includes nucleotides encoding a 5' untranslated region (UTR) and a 3' UTR. These UTRs are located at the ends of each genomic segment. Nucleotides useful as 5' UTRs and 3' UTRs are those present in Pichinde virus and are readily available to the skilled person (see, for instance, Buchmeier et al., 2007, Arenaviridae: the viruses and their replication. In: Knipe and Howley (eds), Fields Virology. 5th ed. Philadelphia, Pa.: Lippincott Williams & Wilkins. pp. 1791-1827). In one embodiment, a genomic segment that encodes a Z protein and an L RdRp protein includes a 5' UTR sequence that is 5' CGCACCGGGGAUCCUAGGCAUCUUUGGGUCACGCUUCAAAUUUGUCCAAUUUGAA CCCAGCUCAAGUCCUGGUCAAAACUUGGG (SEQ ID NO:8) and a 3' UTR sequence that is CGCACCGAGGAUCCUAGGCAUUUCUUGAUC (SEQ ID NO:9). In one embodiment, a genomic segment that encodes a NP protein or a glycoprotein includes a 5' UTR sequence that is 5' CGCACCGGGGAUCCUAGGCAUACCUUGGACGCGCAUAUUACUUGAUCAAAG (SEQ ID NO:10) and a 3' UTR sequence that is 5' CGCACAGUGGAUCCUAGGCGAUUCUAGAUCACGCUGUACGUUCACUUCUUCACUG ACUCGGAGGAAGUGCAAACAACCCCAAA (SEQ ID NO: 11). Alterations in these sequences are permitted, and the terminal 27-30 nucleotides are highly conserved between the genomic segments.

Each genomic segment also includes an intergenic region located between the coding region encoding a Z protein and the coding region encoding a L RdRp protein, between the coding region encoding a nucleoprotein and the at least one first restriction enzyme site, and between the coding region encoding a glycoprotein and at least one second restriction enzyme site. Nucleotides useful as an intergenic region are those present in Pichinde virus and are readily available to the skilled person. In one embodiment, an IGR sequence of a genomic segment that encodes a Z protein and an L RdRp protein includes 5' ACCAGGGCCCCUGGGCGCAC-CCCCCUCCGGGGGUGCGCCCGGGGGCCCCCGGC-CCC AUGGGGCCGGUUGUU (SEQ ID NO:12). In one embodiment, an IGR sequence of a genomic segment that encodes a NP protein or a glycoprotein includes 5' GCCCUAGCCUCGACAUGGGCCUCGACGUCACUC-CCCAAUAGGGGAGUGACGUCGA GGCCUCUGAG-GACUUGAGCU (SEQ ID NO:13).

In one embodiment, each genomic segment is present in a vector. In one embodiment, the sequence of a genomic segment in the vector is antigenomic, and in one embodiment the sequence of a genomic segment in the vector is genomic. As used herein, "anti-genomic" refers to a genomic segment that encodes a protein in the orientation opposite to the viral genome. For example, Pichinde virus is a negative-sense RNA virus. However, each genomic segment is ambisense, encoding proteins in both the positive-sense and negative-sense orientations. "Anti-genomic" refers to the positive-sense orientation, while "genomic" refers to the negative-sense orientation.

A vector is a replicating polynucleotide, such as a plasmid, phage, or cosmid, to which another polynucleotide may be attached so as to bring about the replication of the attached polynucleotide. Construction of vectors containing a genomic segment, and construction of genomic segments including insertion of a polynucleotide encoding an antigen, employs standard ligation techniques known in the art. See, e.g., Sambrook et al, *Molecular Cloning: A Laboratory Manual*, Cold Spring Harbor Laboratory Press (1989) or Ausubel, R. M., ed. *Current Protocols in Molecular Biology* (1994). A vector can provide for further cloning (amplification of the polynucleotide), i.e., a cloning vector, or for expression of an RNA encoded by the genomic segment, i.e., an expression vector. The term vector includes, but is not limited to, plasmid vectors, viral vectors, cosmid vectors, or artificial chromosome vectors. Typically, a vector is capable of replication in a prokaryotic cell and/or a eukaryotic cell. In one embodiment, the vector replicates in prokaryotic cells, and not in eukaryotic cells. In one embodiment, the vector is a plasmid.

Selection of a vector depends upon a variety of desired characteristics in the resulting construct, such as a selection marker, vector replication rate, and the like. Suitable host cells for cloning or expressing the vectors herein are prokaryote or eukaryotic cells.

An expression vector optionally includes regulatory sequences operably linked to the genomic segment. The term "operably linked" refers to a juxtaposition of components such that they are in a relationship permitting them to function in their intended manner. A regulatory sequence is "operably linked" to a genomic segment when it is joined in such a way that expression of the genomic segment is achieved under conditions compatible with the regulatory sequence. One regulatory sequence is a promoter, which acts as a regulatory signal that bind RNA polymerase to initiate transcription of the downstream (3' direction) genomic segment. The promoter used can be a constitutive or an inducible promoter. The invention is not limited by the use of any particular promoter, and a wide variety of promoters are known. In one embodiment, a T7 promoter is used. Another regulatory sequence is a transcription terminator located downstream of the genomic segment. Any transcription terminator that acts to stop transcription of the RNA polymerase that initiates transcription at the promoter may be used. In one embodiment, when the promoter is a T7 promoter, a T7 transcription terminator is also used. In one embodiment, a ribozyme is present to aid in processing an RNA molecule. A ribozyme may be present after the sequences encoding the genomic segment and before a transcription terminator. An example of a ribozyme is a hepatitis delta virus ribozyme. One example of a hepatitis delta virus ribozyme is 5' AGCTCTCCCTTAGCCATC-CGAGTGGACGACGTCCTCCTTCGGATGCCCAGGT-CGGAC CGCGAGGAGGTGGAGATGCCATGCCGAC-CC (SEQ ID NO:14).

Transcription of a genomic segment present in a vector results in an RNA molecule. When each of the three genomic segments is present in a cell the coding regions of the genomic segments are expressed and viral particles that contain one copy of each of the genomic segments are produced. The three genomic segments of the reverse genetics system described herein are based on Pichinde virus, an arenavirus with a segmented genome of two single-stranded ambisense RNAs. While the ability of the reverse genetics system to replicate and produce infectious virus typically requires the presence of the ambisense RNAs in a cell, the genomic segments described herein also include the complement thereof (i.e., complementary RNA), and the corresponding DNA sequences of the two RNA sequences.

The polynucleotide used to transform a host cell optionally includes one or more marker sequences, which typically encode a molecule that inactivates or otherwise detects or is detected by a compound in the growth medium. For example, the inclusion of a marker sequence can render the transformed cell resistant to an antibiotic, or it can confer compound-specific metabolism on the transformed cell. Examples of a marker sequence are sequences that confer resistance to kanamycin, ampicillin, chloramphenicol, tetracycline, and neomycin.

Also provided herein are compositions including a viral particle described herein, or the three genomic segments described herein. Such compositions typically include a pharmaceutically acceptable carrier. As used herein "pharmaceutically acceptable carrier" includes saline, solvents, dispersion media, coatings, antibacterial and antifungal agents, isotonic and absorption delaying agents, and the like, compatible with pharmaceutical administration. Additional active compounds can also be incorporated into the compositions.

A composition described herein may be referred to as a vaccine. The term "vaccine" as used herein refers to a composition that, upon administration to an animal, will increase the likelihood the recipient mounts an immune response to an antigen encoded by one of the genomic segments described herein.

A composition may be prepared by methods well known in the art of pharmaceutics. In general, a composition can be formulated to be compatible with its intended route of administration. Administration may be systemic or local. Examples of routes of administration include parenteral (e.g., intravenous, intradermal, subcutaneous, intraperitoneal, intramuscular), enteral (e.g., oral), and topical (e.g., epicutaneous, inhalational, transmucosal) administration. Appropriate dosage forms for enteral administration of the compound of the present invention may include tablets, capsules or liquids. Appropriate dosage forms for parenteral administration may include intravenous administration.

Appropriate dosage forms for topical administration may include nasal sprays, metered dose inhalers, dry-powder inhalers or by nebulization.

Solutions or suspensions can include the following components: a sterile diluent such as water for administration, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; electrolytes, such as sodium ion, chloride ion, potassium ion, calcium ion, and magnesium ion, and agents for the adjustment of tonicity such as sodium chloride or dextrose. pH can be adjusted with acids or bases, such as hydrochloric acid or sodium hydroxide. A composition can be enclosed in ampoules, disposable syringes or multiple dose vials made of glass or plastic.

Compositions can include sterile aqueous solutions (where water soluble) or dispersions and sterile powders for the extemporaneous preparation of sterile solutions or dispersions. For intravenous administration, suitable carriers include physiological saline, bacteriostatic water, phosphate buffered saline (PBS), and the like. A composition is typically sterile and, when suitable for injectable use, should be fluid to the extent that easy syringability exists. It should be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile solutions can be prepared by incorporating the active compound (e.g., a viral particle described herein) in the required amount in an appropriate solvent with one or a combination of ingredients enumerated above, followed by filtered sterilization. Generally, dispersions are prepared by incorporating the active compound into a sterile vehicle, which contains a basic dispersion medium and any other appropriate ingredients. In the case of sterile powders for the preparation of sterile injectable solutions, preferred methods of preparation include vacuum drying and freeze-drying which yields a powder of the active ingredient plus any additional desired ingredient from a previously sterilized solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the active compounds are delivered in the form of an aerosol spray from a pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds may be prepared with carriers that will protect the compound against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. Such formulations can be prepared using standard techniques. Liposomal suspensions can also be used as pharmaceutically acceptable carriers. These can be prepared according to methods known to those skilled in the art.

The data obtained from cell culture assays and animal studies can be used in formulating a range of dosage for use in an animal. The dosage of such compounds lies preferably within a range of circulating concentrations that include the $ED_{50}$ (the dose therapeutically effective in 50% of the population) with little or no toxicity. The dosage may vary within this range depending upon the dosage form employed and the route of administration utilized.

The compositions can be administered once to result in an immune response, or one or more additional times as a booster to potentiate the immune response and increase the likelihood immunity to the antigen is long-lasting. The skilled artisan will appreciate that certain factors may influence the dosage and timing required to effectively treat a subject, including but not limited to the severity of the disease or disorder, previous treatments, the general health and/or age of the subject, and other diseases present.

Also provided herein are methods for using the genomic segments. In one embodiment, a method includes making an infectious viral particle. Such a method includes, but is not limited to, providing a cell that includes each of the three genomic segments described herein (a first genomic segment, a second genomic segment, and a third genomic segment) and incubating the cell under conditions suitable for generating full-length genomic RNA molecules of each genomic segment. The full-length genomic RNA of each genomic segment is antigenomic. Production of full-length genomic RNA molecules of each genomic segment results in transcription and translation of each viral gene product and amplification of the viral genome to generate infectious progeny virus particles. As used herein, an "infectious virus particle" refers to a virus particle that can interact with a suitable eukaryotic cell, such as a mammalian cell (e.g., a murine cell or a human cell) or an avian cell, to result in the introduction of the three genomic segments into the cell, and the transcription of the three genomic segments in the cell. The method may also include introducing into the cell vectors that encode the three genomic segments. Infectious virus particles are released into supernatants and may be isolated and amplified further by culturing on cells. The method may include isolating a viral particle from a cell or a mixture of cells and cellular debris. The method may include inactivating virus particles using standard methods, such a hydrogen peroxide treatment. Also provided is a viral particle, infectious or inactivated, that contains three genomic segments described herein.

In one embodiment, a method includes expression of an antigen in a cell. Such a method includes, but is not limited to, introducing into a cell the three genomic segments described herein. In one embodiment, the introducing is by introduction of a virus particle that is infectious or inactivated. The second and/or the third genomic segment may include a second coding region that encodes an antigen. The second and third genomic segments may encode the same antigen or they may encode different antigens. More than one type of virus particle may be administered. For instance, two populations of virus particles may be administered where each population encodes different antigens. In this embodiment, a single administration can result in expressing multiple antigens in a cell. The cell is a suitable eukaryotic cell, such as a mammalian cell (e.g., a murine cell or a human cell) or an avian cell. In one embodiment, the avian cell is a chicken embryonic fibroblast. The cell may be ex vivo or in vivo. The three genomic segments may be introduced by contacting a cell with an infectious virus particle that contains the three genomic segments, or by introducing into the cell vectors that include the genomic segments. The method further includes incubating the cell under conditions suitable for expression of the coding regions present on the three genomic segments, including the one or two second coding regions present on the second and/or third genomic segments. As used herein, "ex vivo" refers to a cell that has been removed from the body of an animal. Ex vivo cells include, for instance, primary cells (e.g., cells that have recently been removed from a subject and are capable of limited growth in tissue culture medium), and cultured cells (e.g., cells that are capable of long term culture in tissue culture medium). "In vivo" refers to cells that are within the body of a subject.

In one embodiment, a method includes immunizing an animal. Such a method includes, but is not limited to, administering to an animal a viral particle that is infectious or inactivated, that contains the three genomic segments described herein. The second and/or the third genomic segment may include a second coding region that encodes an antigen. The second and third genomic segments may encode the same antigen or they may encode different antigens. More than one type of virus particle may be administered. For instance, two populations of virus particles may be administered where each population encodes different antigens. In this embodiment, a single administration can result in vaccinating an animal against multiple pathogens. The animal may be any animal in need of immunization, including a vertebrate, such as a mammal or an avian. The animal can be, for instance, avian (including, for instance, chicken or turkey), bovine (including, for instance, a member of the species *Bos taurus*), caprine (including, for instance, goat), ovine (including, for instance, sheep), porcine (including, for instance, swine), bison (including, for instance, buffalo), a companion animal (including, for instance, cat, dog, and horse), members of the family Muridae (including, for instance, rat or mouse), Guinea pig, or human. In one embodiment, the animal may be an animal at risk of exposure to an infectious disease, such as a disease caused by or associated with a viral, prokaryotic, or eukaryotic pathogen. In one embodiment, the animal may be an animal in need of immunization against an antigen that is associated with non-infectious disease, such as cancer. For instance, the antigen may be one that helps an animal mount an immune response that targets and eliminates cancer cells. The immune response may be a humoral response (e.g., the immune response includes production of antibody in response to an antigen), a cellular response (e.g. the activation of phagocytes, antigen-specific cytotoxic T-lymphocytes, and the release of cytokines in response to an antigen), or a combination thereof.

In another embodiment, a method includes treating one or more symptoms of certain conditions in an animal. In one embodiment, a condition is caused by infection by a virus or a microbe. As used herein, the term "infection" refers to the presence of and multiplication of a virus or microbe in the body of a subject. The infection can be clinically inapparent, or result in symptoms associated with disease caused by the virus or microbe. The infection can be at an early stage, or at a late stage. In another embodiment, a condition is caused by a disease, such as cancer. As used herein, the term "disease" refers to any deviation from or interruption of the normal structure or function of a part, organ, or system, or combination thereof, of a subject that is manifested by a characteristic symptom or set of symptoms. The method includes administering an effective amount of a composition described herein to an animal having or at risk of having a condition, or symptoms of a condition, and determining whether at least one symptom of the condition is changed, preferably, reduced.

Treatment of symptoms associated with a condition can be prophylactic or, alternatively, can be initiated after the development of a condition. As used herein, the term "symptom" refers to objective evidence in a subject of a condition caused by infection by disease. Symptoms associated with conditions referred to herein and the evaluations of such symptoms are routine and known in the art. Treatment that is prophylactic, for instance, initiated before a subject manifests symptoms of a condition, is referred to herein as treatment of a subject that is "at risk" of developing the condition. Accordingly, administration of a composition can be performed before, during, or after the occurrence of the conditions described herein. Treatment initiated after the development of a condition may result in decreasing the severity of the symptoms of one of the conditions, or completely removing the symptoms. In this aspect of the invention, an "effective amount" is an amount effective to prevent the manifestation of symptoms of a condition, decrease the severity of the symptoms of a condition, and/or completely remove the symptoms.

Also provided herein is a kit for immunizing an animal. The kit includes viral particles as described herein, where the second and/or third genomic segments each independently include a coding region that encodes an antigen, in a suitable packaging material in an amount sufficient for at least one immunization. In one embodiment, the kit may include more than one type of viral particle, e.g., the kit may include one viral particle that encodes one or two antigens and a second viral particle that encodes one or two other antigens. Optionally, other reagents such as buffers and solutions needed to practice the invention are also included. Instructions for use of the packaged viral particles are also typically included.

As used herein, the phrase "packaging material" refers to one or more physical structures used to house the contents of the kit. The packaging material is constructed by known methods, preferably to provide a sterile, contaminant-free environment. The packaging material has a label which indicates that the viral particles can be used for immunizing an animal. In addition, the packaging material contains instructions indicating how the materials within the kit are employed to immunize an animal. As used herein, the term "package" refers to a solid matrix or material such as glass, plastic, paper, foil, and the like, capable of holding within fixed limits viral particles. Thus, for example, a package can be a glass vial used to contain an appropriate amount of viral particles. "Instructions for use" typically include a tangible expression describing the amount of viral particles, route of administration, and the like.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

The present invention is illustrated by the following examples. It is to be understood that the particular examples, materials, amounts, and procedures are to be interpreted broadly in accordance with the scope and spirit of the invention as set forth herein.

Example 1

An Arenavirus-Based Vaccine Vector Carrying Influenza Virus Antigens Confers Long-Term Protection of Mice Against Lethal Influenza Virus Challenge Pichinde virus (PICV) is a non-pathogenic arenavirus that has been used as a model virus to study viral hemorrhagic fever infection. A reverse genetics system was previously developed to generate infectious PICV viruses from two plasmids that encode the viral large (L) and small (S) RNA segments (Lan et al., 2009, J Virol 83:6357-6362). In the current study, a second-generation reverse genetics system was created to produce recombinant infectious PICV viruses from 3 separate plasmids that are referred to as the tri-segmented PICV system. These recombinant viruses carry 3 viral genomic RNA segments that encode for all of the viral gene products as well as two foreign genes. This tri-segmented PICV system can be used as a novel vaccine vector to deliver the hemagglutination (HA) and the nucleoprotein (NP) of the influenza virus A/PR8 strain. Mice immunized with these recombinant viruses are protected against lethal influenza virus challenge as evidenced by the survival of the animals afforded by the high levels of HA neutralizing antibodies and NP-specific cytotoxic T lymphocyte (CTL) responses to viral infection. These tri-segmented recombinant PICV viruses do not induce strong anti-PICV vector immunity, thus making them ideal candidates in a prime-boost vaccination strategy in order to induce cross-reactive immunity. In summary, a novel live vaccine vector has been developed that can express multiple foreign antigens to induce strong humoral and cell-mediated immunity and little anti-vector immunity in vivo.

Introduction

We have developed the only available reverse-genetics system to generate infectious PICV viruses from plasmid transfection into appropriate mammalian cells (Lan et al., 2009, J Virol 83:6357-6362). This system consists of 2 plasmids to generate full-length genomic L and S RNAs from an engineered bacteriophage T7 regulatory (promoter/terminator) signals and the hepatitis delta ribozyme sequence located upstream and downstream of the PICV genomic sequences, respectively. When transfected into baby hamster's kidney epithelial cells that constitutively express the bacteriophage T7 RNA polymerase (BSRT7-5, a.k.a. BHK-T7), the L and S RNA segments of PICV are generated, from which all PICV viral gene products, including the L polymerase and NP nucleoprotein are transcribed and translated in order to amplify the viral genome and generate infectious progeny virus particles. Infectious PICV viruses are released into supernatants and are isolated and amplified further by culturing on African green-monkey epithelial (Vero) cells.

As described herein a second-generation reverse genetics system has been developed to produce recombinant infectious PICV viruses from 3 separate plasmids that are referred to as the tri-segmented PICV system. These recombinant viruses carry 3 viral genomic RNA segments that encode for all of the viral gene products as well as two foreign genes. This tri-segmented PICV system can be used as a novel vaccine vector to deliver other viral antigens, such as those of the influenza virus. Briefly summarized, tri-segmented PICV viruses expressing the hemagglutination (HA) or the nucleoprotein (NP) of the influenza virus A/PR8 strain have been produced, and these tri-segmented PICV vaccine vectors can induce strong humoral and cell-mediated immunity, such as a robust production of influenza-specific neutralizing antibodies and a strong influenza-specific cytotoxic T lymphocyte (CTL) response in vaccinated mice with little anti-PICV vector immunity, which makes them ideal candidates for the prime-boost vaccination strategy in order to induce long-lasting and cross-reactive immunity. Therefore, this novel PICV-based vaccine vector system described herein we have developed satisfies all required criteria of an ideal viral vector, such as safety, induction of strong and durable cellular and humoral immune responses, no pre-existing immunity and lack of anti-vector immunity.

Materials and Methods

Construction of Plasmids Encoding the Engineered Pichinde Virus P18 S RNA Segments with Multiple-Cloning-Sites (MCS) Replacing Either GPC or NP Gene.

A reverse genetics system for PICV was previously developed by transfection of 2 plasmids, encoding the L and S RNA segments in anti-genomic (ag) sense, into BHK-T7 cells (FIG. 1) (Lan et al., 2009, J Virol 83:6357-6362). The overlaping polymerase chain reaction (PCR) method was used to replace the open-reading-frame (ORF) of either the viral glycoprotein (GPC) or nucleoprotein (NP) gene with multiple cloning sites (MCS) in the S agRNA encoding plasmid. The resulting plasmids (FIG. 2A), P18S-GPC/MCS and P18S-MCS/NP, contain MCS with the restriction enzyme sequences (Nhe I-Mfe I-Acc65I-Kpn I-EcoR V-Xho I-Sph I) that are introduced into these plasmids for the convenience of cloning foreign genes (e.g., reporter genes and/or viral antigens).

Subcloning of GFP reporter gene, influenza HA or NP gene into P18S-GPC/MCS vector. PCR was used to subclone the green fluorescence protein (GFP) reporter gene and the influenza HA or NP gene from the A/PR8 (H1N1) strain into the vector P18S-GFP/MCS between Nhe I and Xho I sites, respectively. The amino acid sequence of the A/PR8 hemagglutinin can be found at Genbank Accession number NC_002017.1, and the amino acid sequence of the A/PR8 nucleoprotein can be found at Genbank Accession number NC_002019.1. The recombinant plasmid constructs were confirmed by DNA sequencing. The resulting plasmids (FIG. 5) are called P18S-GPC/GFP, P18S-GPC/H1, and P18S-GPC/NP, respectively.

Recovery of Recombinant Tri-Segmented Pichinde Viruses Expressing GFP, Influenza HA or NP.

Figure 5:
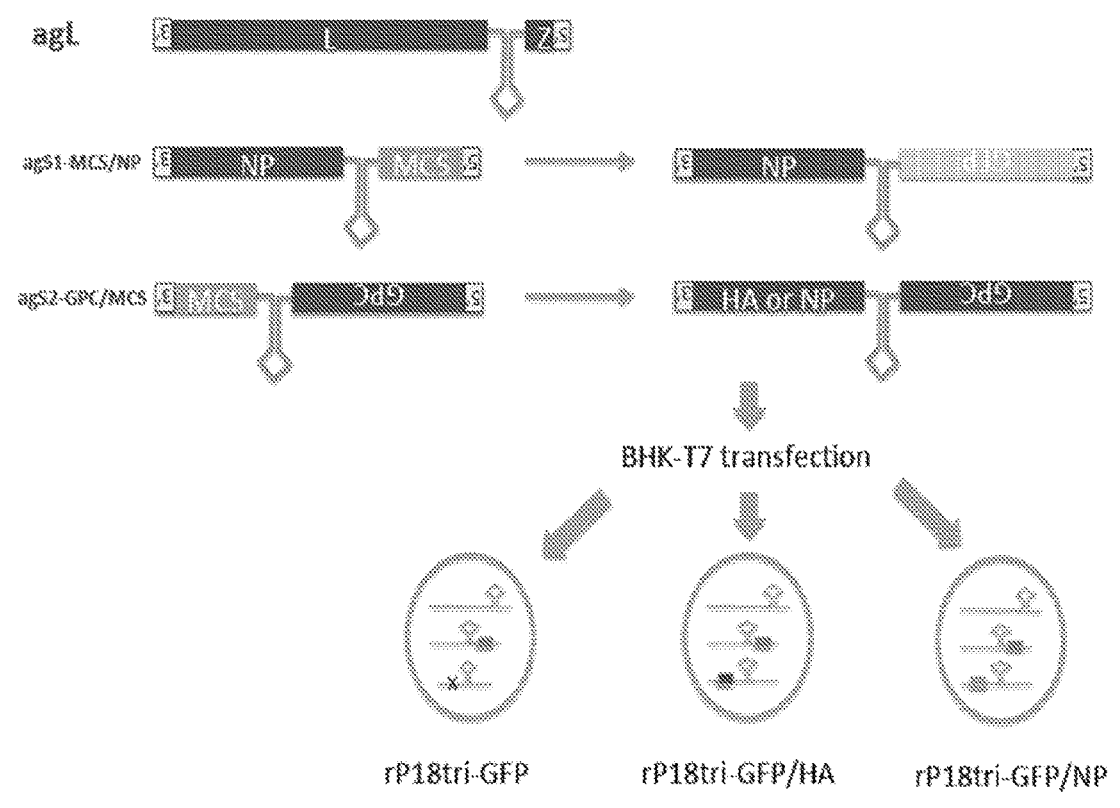

Recombinant viruses were recovered from plasmids by transfecting BSRT7-5 (a.k.a. BHK-T7) cells with 3 plasmids expressing the full-length P18 L agRNA segment, a P18S segment with MCS in place of GPC (P18S-MCS/NP), and a P18S segment with GFP, HA, or NP gene in place of NP (P18S-GPC/GFP, P18S-GPC/N1, or P18S-GPC/NP) (FIG. 2B and FIG. 5). The procedures to generate recombinant PICV are essentially the same as previously described (FIG. 1B) (Lan et al., 2009, J Virol 83:6357-6362). Briefly, BHK-T7 cells were grown to 80% confluency and 4 hours before transfection the cells were washed and incubated with antibiotic-free media. For transfection, 2 ug of each plasmid was diluted in 250 ul of Opti-MEM and incubated at room temperature for 15 minutes. An equal volume of Opti-MEM with 10 ul of lipofectamine (Invitrogen, Life technologies) was added and the mixture was incubated for 20 mins at room temperature. Following incubation, the cells were transfected with the plasmids and media was again replaced after 4 hours to remove lipofectamine. After 48 hours of transfection, cell supernatants were collected for plaque assay. Virus grown from individual plaques was used to prepare stocks that were grown on BHK-21 cells and was stored at −80 C.

Detection of Influenza Antigen Expression in Cells Infected with Recombinant Tri-Segmented PICV Vectors.

BHK-21 cells grown on coverslips were infected with wild type Pichinde virus (PICV) or recombinant PICV viruses expressing either the influenza HA (rPICV-HA) or NP gene (rPICV-NP). After 24 hours of virus infection, cells were fixed with 4% paraformaldehyde for 15 mins at room temperature followed by 3 washes with phosphate buffer saline (PBS). Cells were then incubated in 0.1% Triton X-100 for 12 minutes followed by 1 hour incubation with primary antibody (mouse anti-NP influenza A). Cells were then washed and incubated with secondary antibody (anti mouse alexa flour-647) for 1 hour at room temperature.

Mouse Immunization and Challenge.

Six- to eight-week old female C57BL/6 mice were obtained from Charles River Laboratories and housed for at least 1 week for acclimatization. Mice were housed in microisolator cages in BSL-2 equipped animal facility. Mice were injected with 100,000 pfu of rPICV virus in 100 ul of total volume through intra-peritoneal route. After 14 days of last booster, mice were challenged intra-nasally with 10 $LD_{50}$ (10,000 pfu) of the mouse-adapted influenza A/PR8 strain.

Analysis of Virus Specific CTL by Tetramer Staining.

Single-cell splenocytes were obtained and red blood cells (RBCs) were lysed using ACK lysis buffer. The splenocytes were then washed with FACS buffer (PBS+2% FBS) twice. Cells ($1 \times 10^5$) were stained with CD8-PerCP-Cy5.5, CD3-APC and H-2Db-PE tetramer with the $NP_{366-374}$ epitope ASNENMETM (SEQ ID NO:7) for 1 hr at room temperature. After incubation, cells were washed with FACS buffer three times and the labeled cells were analyzed by flow cytometry. The FACS data was analyzed using FloJo software.

Hemagglutination Inhibition Assay.

Blood was collected after 14 days of each immunization and serum was harvested. Non-specific inhibitors were removed from the serum by an overnight treatment with 5 volumes of receptor destroying enzyme (Sigma), followed by 45 min incubation at 56° C. to inactivate the enzyme and serum. Each serum sample was then serially diluted in 25 ul of PBS and then mixed with an equal volume of PBS containing 4 HA units of A/PR8. After 15 min incubation at room temperature, 50 ul of 0.5% turkey RBC was added and the mixture was incubated for 1 hour at 4 C before evaluation of agglutination. The titre was recorded as the inverse of the last dilution that inhibited agglutination.

Determination of Virus Titers in the Lungs.

To evaluate the replication of influenza A/PR8 in mice, lungs were collected on day 6 of post challenge, weighed and homogenized in L15 media. Tissue homogenate was centrifuged at 10,000 rpm for 10 mins and virus was titrated in 12-well plate on monolayers of Madin-Darby canine kidney (MDCK) cells.

Results

1. Generation of Recombinant Tri-Segmented Pichinde Virus Expressing the GFP Reporter Gene.

Figure 1:
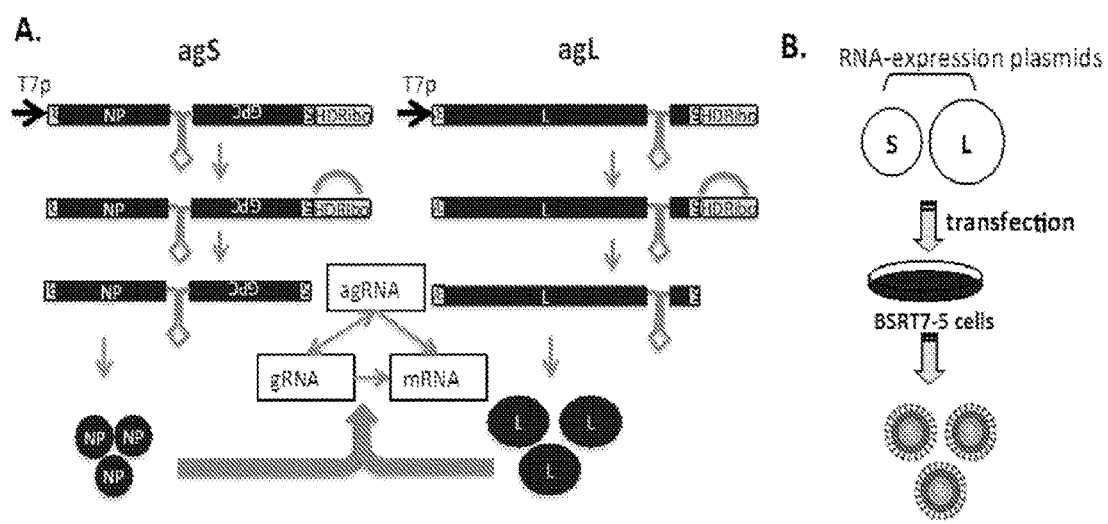
FIG. 1. Diagram of the 2-plasmid PICV reverse genetics system (Lan et al., 2009, J Virol 83:6357-6362). A reverse genetics system for PICV was previously developed by transfection of 2 plasmids, encoding the L and S RNA segments in anti-genomic (ag) sense (FIG. 1A), into BHK-T7 (a.k.a. BSRT7-5) cells (FIG. 1B). This system consists of 2 plasmids expressing the L and S segments of PICV when they are transfected into the BSRT7-5 (a.k.a. BHKT7) cells (FIG. 1). The overlaping polymerase chain reaction (PCR) method was used to replace the open-reading-frame (ORF) of either the viral glycoprotein (GPC) or nucleoprotein (NP) gene with multiple cloning sites (MCS) in the S agRNA encoding plasmid FIG. 2. The 3-plasmid system to generate infectious tri-segmented PICV rP18tri-GFP. The plasmids resulting from the reverse genetics system of FIG. 1 were designated P18S-GPC/MCS and P18S-MCSNP. A second-generation of the PICV reverse genetic system was generated that consists of 3 plasmids that produce two distinct S RNA segments, one carrying a deletion in GPC and the other S segment contains a deletion of the NP gene, and in place of the deleted viral genes multiple cloning sites (MCSs) were inserted (FIG. 2A). The GFP reporter gene was subcloned into the P18 S2 segment at the deleted GPC position, and infectious viruses were generated from the supernatants of BSRT7-5 cells transfected with three plasmids, one encoding the viral Z and L genes on the full-length P18 L segment, and the other two S1 and S2 plasmids (i.e., P18 S1-MCS and P18 S2-GFP) expressing either the viral GPC gene alone or both NP and GFP reporter genes (FIG. 2B).

A tri-segmented arenavirus system was first reported for LCMV by de la Torre group (Emonet et al., 2009, Proc Natl Acad Sci USA 106:3473-3478), which has generated infectious recombinant LCMV that packages 3 RNA segments, one full-length L segment, and two S segments with deletion in either GPC or NP. We have previously developed a reverse genetics system for the Pichinde virus (PICV) (Lan et al., 2009, J Virol 83:6357-6362), which is a prototypic arenavirus that is non-pathogenic in humans. This system consists of 2 plasmids expressing the L and S segments of PICV when they are transfected into the BSRT7-5 (a.k.a. BHKT7) cells (FIG. 1).

Figure 2:
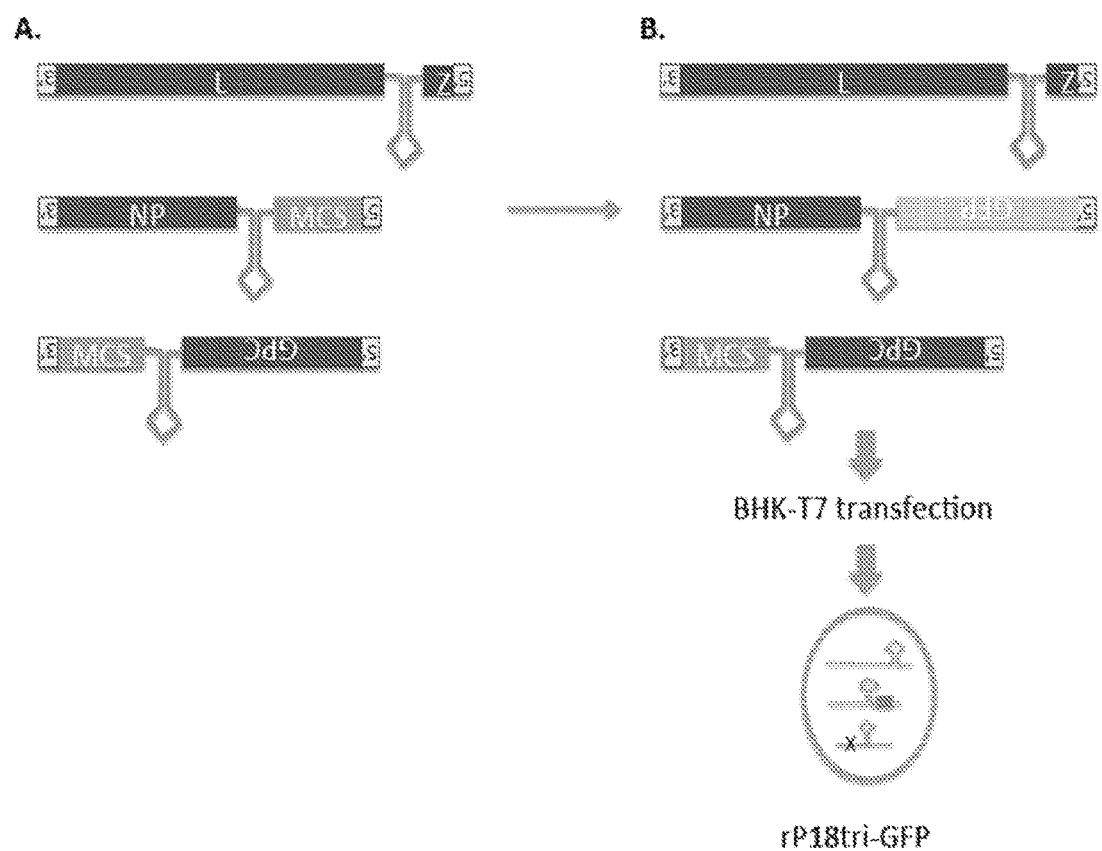
Figure 3:
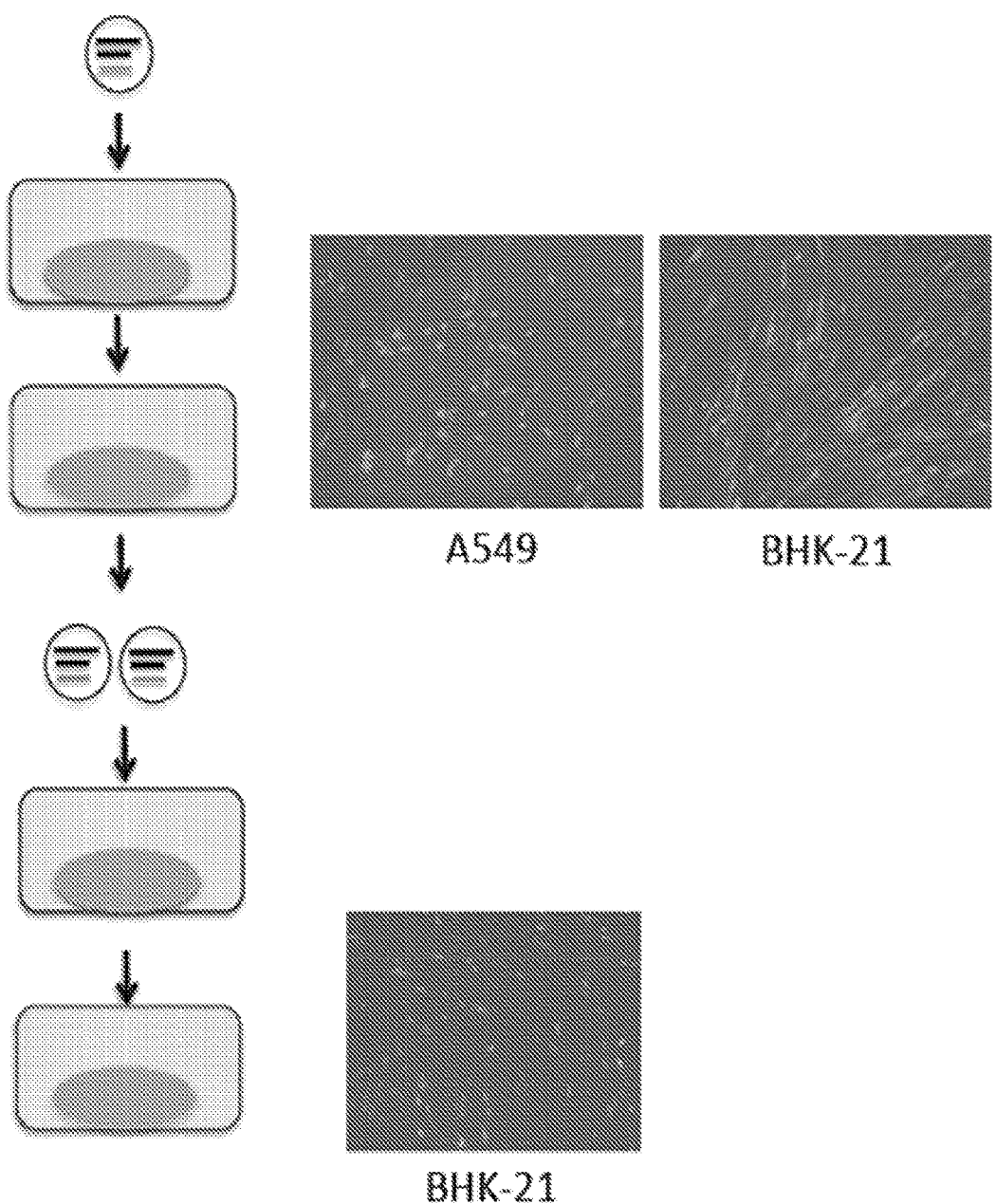
FIG. 3. Characterization of rP18tri-GFP virus. A549 or BHK-21 cells were infected with rP18tri-GFP virus for 24 hours, and GFP expression was detected in the infected cells. Virus supernatants were harvested and used to infect a fresh culture of the BHK-21 cells, in which GFP expression was also detected.
Figure 4:
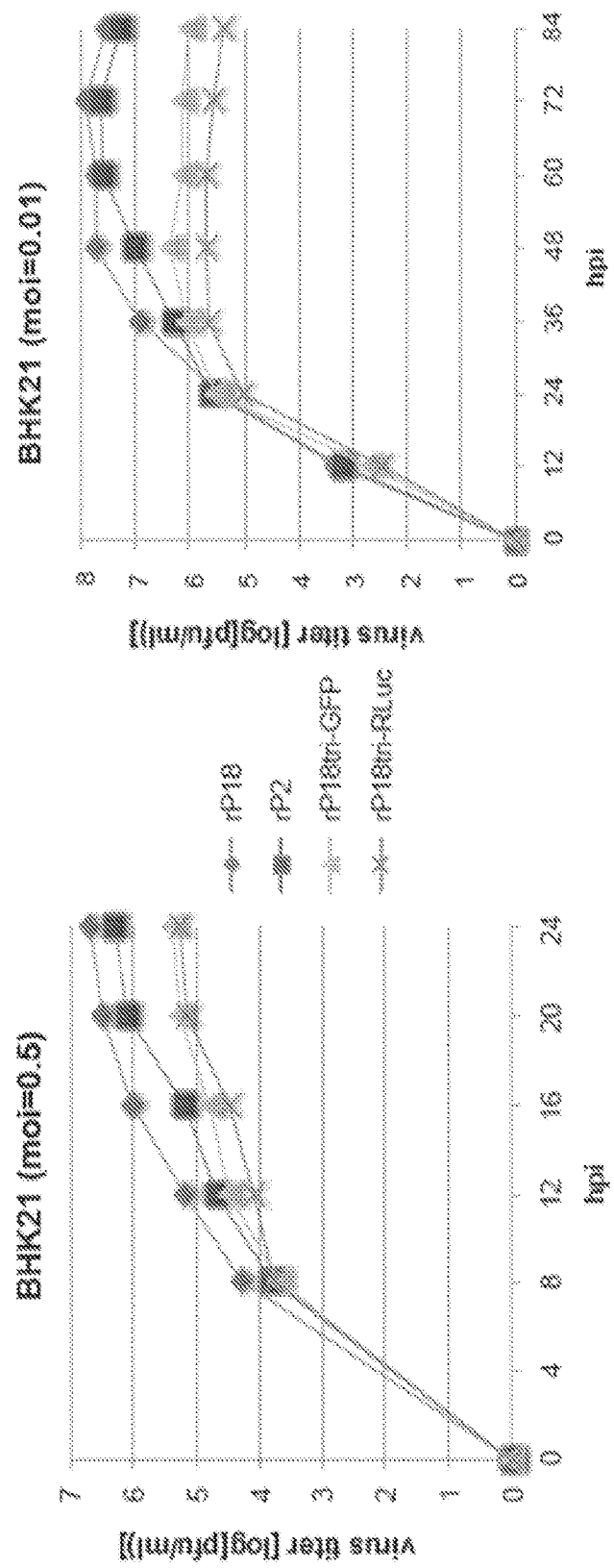
FIG. 4. Virus growth comparison of rP2, rP18, tri-segmented viruses rP18tri-GFP and rP18tri-RLuc in BHK-21 cell at high (moi=0.5) and low (moi=0.01) moi.

In the current study, a second-generation of the PICV reverse genetic system has been generated that consists of 3 plasmids that produce two distinct S RNA segments, one carrying a deletion in GPC and the other S segment contains a deletion of the NP gene (FIG. 2). In place of the deleted viral genes, we have inserted the multiple cloning sites (MCSs) (FIG. 2A). We then subcloned the GFP reporter gene into the P18 S2 segment at the deleted GPC position using Nhe I/Kpn I sites within MCS, and generated infectious viruses from the supernatants of BSRT7-5 cells transfected with three plasmids, one encoding the viral Z and L genes on the full-length P18 L segment, and the other two S1 and S2 plasmids (i.e., P18 S1-MCS and P18 S2-GFP) expressing either the viral GPC gene alone or both NP and GFP reporter genes (FIG. 2B). Stock viruses were prepared from plaque-purified viruses. All plaques appeared green under fluorescence microscopy, demonstrating the successful recovery of the rP18tri-GFP virus. In addition to Vero cells (data not shown), rP18tri-GFP virus infection expressed GFP in other permissive cells such as BHK-21 and A549 (FIG. 3), and released more infectious progeny viruses that expressed GFP upon infection of a fresh culture of BHK-21 target cells (FIG. 3), demonstrating the stability and integrity of the rP18tri-GFP virus in cell cultures. Time course studies demonstrated that GFP was strongly expressed after 12 h post-infection and that the complete life cycle of rP18tri-GFP was about 16 h as the concentration of the rP18tri-GFP virus in the supernatants sharply increased at ~16 hpi (FIG. 4). In a preliminary experiment it was found that the PICV-tri-GFP virus vector can infect chicken embryonic fibroblasts (CEF cell line) in cell culture (data not shown).

Virus growths of the bi- and tri-segmented PICVs was compared by performing the growth curve analysis of the rP2, rP18, and rP18tri-GFP on BHK-21 cells at the multiplicity of infection (moi) of 0.01. As expected, the known virulent rP18 virus grew slightly faster and better than rP2 by ~0.5 log in virus titer. The tri-segmented rP18tri-GFP virus grew at a similar kinetic as the rP2 and rP18 viruses albeit at ~1 to 1.5 log lowered virus titers (FIG. 4). In summary, the tri-segmented PICV virus appears to be retarded in growth rate and titers as compared to the bi-segmented rP2 and rP18 PICV viruses.

In order to determine the stability of the rP18tri-GFP virus, that is to test whether in vitro culturing of the rP18tri-GFP virus will select for a bi-segmented wild-type virus revertant that have lost GFP gene due to genome recombination, the rP18tri-GFP was passaged in the BHK-21 cell cultures continuously, and conducted plaque assay at various passages to examine GFP expression in each of the plaques. At any tested passages (up to 23 passages), all plaques still expressed strong GFP reporter gene levels, suggesting that the GFP reporter gene could be stably maintained in the infectious viral particles even after extensive passages in cell culture.

2. Generation of Recombinant Tri-Segmented Pichinde Virus Expressing Influenza Virus Antigens.

HA and NP genes of the influenza virus A/PR8/H1N1 strain were molecularly cloned into the MSC of the P18 S2 plasmid, respectively (FIG. 5). The resulting P18 S2-HA and P18 S2-NP were separately transfected into BHK-T7 cells along with the full-length P18L and P18S1-GFP in order to generate the rP18tri-GFP/HA and rP18tri-GFP/NP viruses, respectively.

Figure 6:
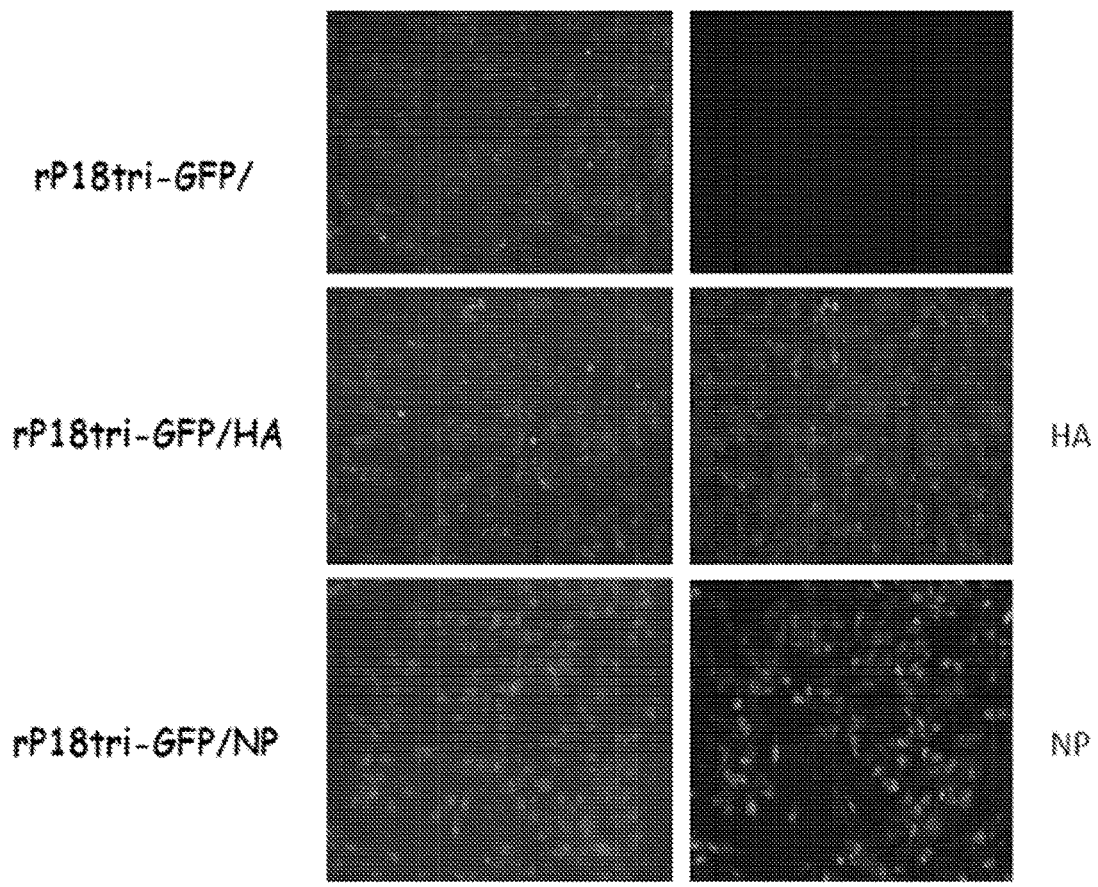
FIG. 6. Detection of expression of the GFP reporter gene product and the influenza HA or NP proteins that were expressed from the rP18tri-based vaccine vectors.

All infected cells (i.e., plaques) were green under fluorescence microscopy as the recombinant viruses carried the GFP reporter gene on the P18S2-GFP segment (FIG. 6). In addition, HA and NP protein expressions were detected by immunofluorescence assay using specific anti-HA and anti-NP antibodies in Vero cells at 24 hr post infection (hpi) (FIG. 6). Taken together, we have shown that the tri-segmented viruses can be made to express different foreign genes, including the GFP reporter gene and two different influenza viral antigens (HA and NP) upon cellular infection.

3. The rP18tri-based Influenza Vaccines Induce Protective Immunity in Mice.

Figure 7:
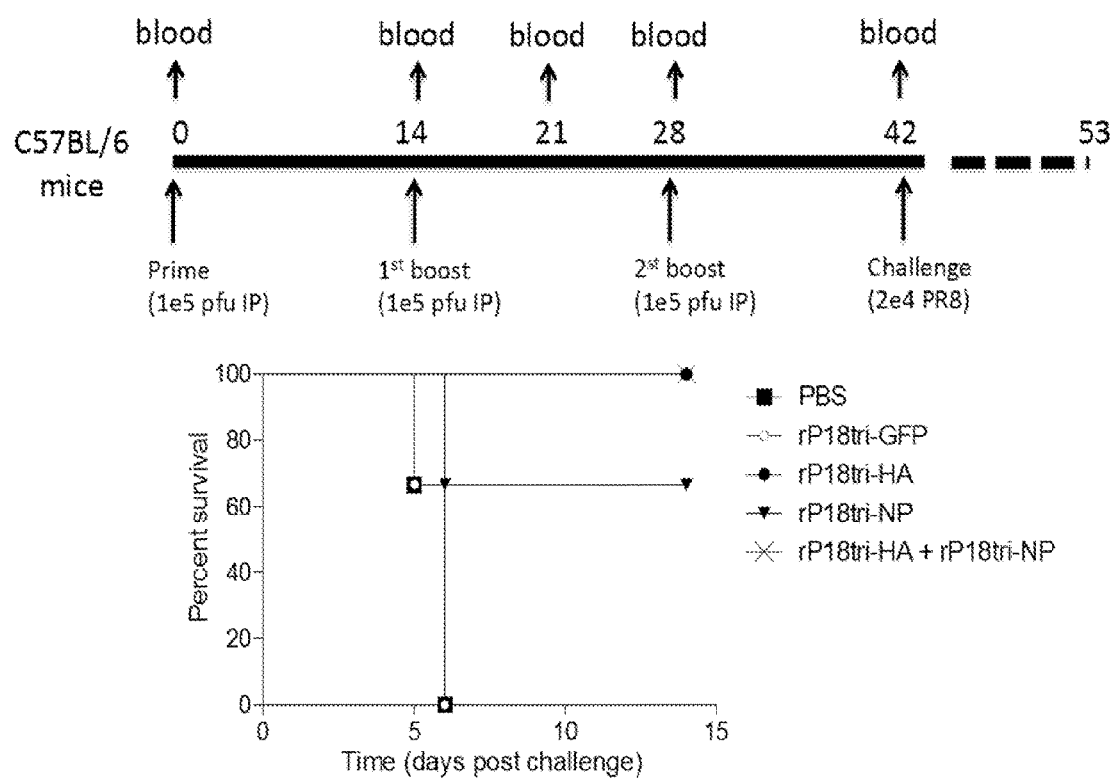
FIG. 7. The rP18tri-based influenza vaccines confer protective immunity in mice. 1e5, $1 \times 10^5$; 2e4, $2 \times 10^4$; IP, intraperitoneal.

Previous work from our laboratory demonstrated that infection of mice with PICV even at high doses via different routes does not cause diseases as PICV is cleared by 4 days post infection (dpi) (data not shown). Here, we have examined whether rP18tri-based vaccine vectors can induce protective immunity in mice. C57BL6 mice were mock infected or infected intranasally (i.n.) with a low dose (50 pfu) of A/PR8 or via i.p. route with $1 \times 10^5$ pfu of rP18tri-GFP, rP18tri-GFP/HA, and rP18tri-GFP/NP viruses, respectively. Mice were boosted twice with the same virus at the same dosage at day 14 and 28. Blood samples were collected at different time points post priming and post boosting for neutralizing antibody titer determination. Mice were challenged at 14 d after the $2^{nd}$ boost with a known lethal dose of A/PR8 (10×MLD50) and monitored for body weight and disease symptoms for up to 21 days. All challenged animals that have previously received PBS or rP18tri-GFP vaccination reached terminal points by 7 dpi, whereas all mice vaccinated with rP18tri-GFP/HA were completely protected from lethal influenza virus infection. Two out of three mice vaccinated with rP18tri-GFP/NP survived (FIG. 7). For rP18tri-GFP/HA vaccination, challenged mice maintained body weight, while the two survivors in the rP18tri-GFP/NP group showed a slight body weight loss at the early stage but quickly recovered (data now shown). Consistent with the mortality data, mice vaccinated with HA or NP had minimal pathological changes in the lungs at 3 dpi, compared to those with PBS or vector alone. Similarly, virus titers in the lungs at 3 dpi also correlated with protection. A/PR8 virus replicated to high levels in mouse lungs at 3 dpi when the animals were vaccinated with mock or the rP18tri-GFP vector alone. In contrast, virus titer was not detectable in the rP18tri-GFP/HA vaccination group and was significantly reduced in the rP18tri-GFP/NP group.

Taken together, these results suggest that the rP18tri-based vaccine vector can induce protective immunity from lethal influenza virus infection in mice. Consistent with previous influenza vaccine studies, HA vaccination can induce a complete protection from influenza virus-induced disease while NP vaccination normally leads to partial protection by reducing disease severity and controlling virus replication in vivo.

4. The rP18tri-GFP/HA Vaccine Induces High Neutralizing Antibody Titers in Mice.

Figure 8:
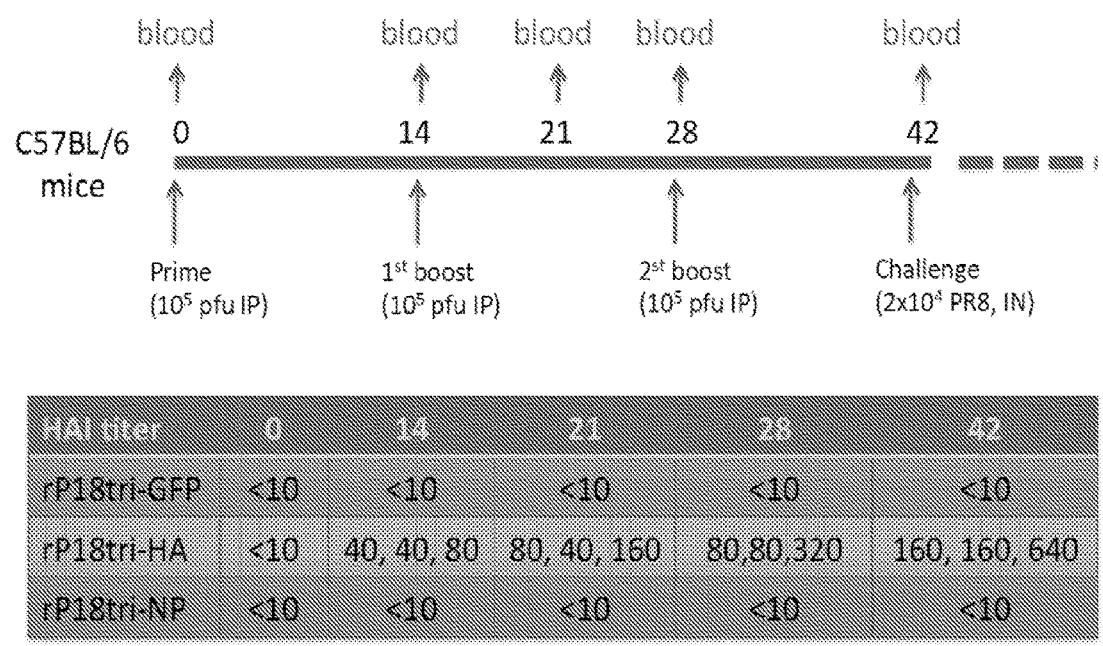
FIG. 8. HAI titers induced by the rP18tri-based influenza vaccines." Timing of vaccination, boost, and blood collection (top schematic) and hemagglutination inhibition (HAI) (lower table) are shown.

The hemagglutination inhibition (HAI) titers was measured in peripheral blood collected from vaccinated mice at different time points: 14 d post-prime, 7 d and 14 d post-$1^{st}$ boost, and 14 d post-$2^{nd}$-boost (FIG. 8). As expected, HAI titers from the rP18tri-GFP and rP18tri-GFP/NP groups did not surpass the background level, because neither GFP nor NP is expected to induce HA-specific neutralizing antibodies. In contrast, HAI titers from the rP18tri-GFP/HA vaccination group reached the level of 40 at 14 d post-prime, and increased substantially after boosting (FIG. 8), suggesting that the rP18tri-GFP/HA vaccine can induce high levels of neutralizing antibody titers in vivo. As a threshold HAI titer of >=40 is generally used as a measure of success, i.e., in providing 50% reduction in the risk of influenza (seroprotective titer) (Reber et al., 2013, Expert Rev Vaccines 12:519-536), the HAI data suggests that a single dose of rP18tri-GFP/HA may be sufficient to confer protection.

Figure 10:
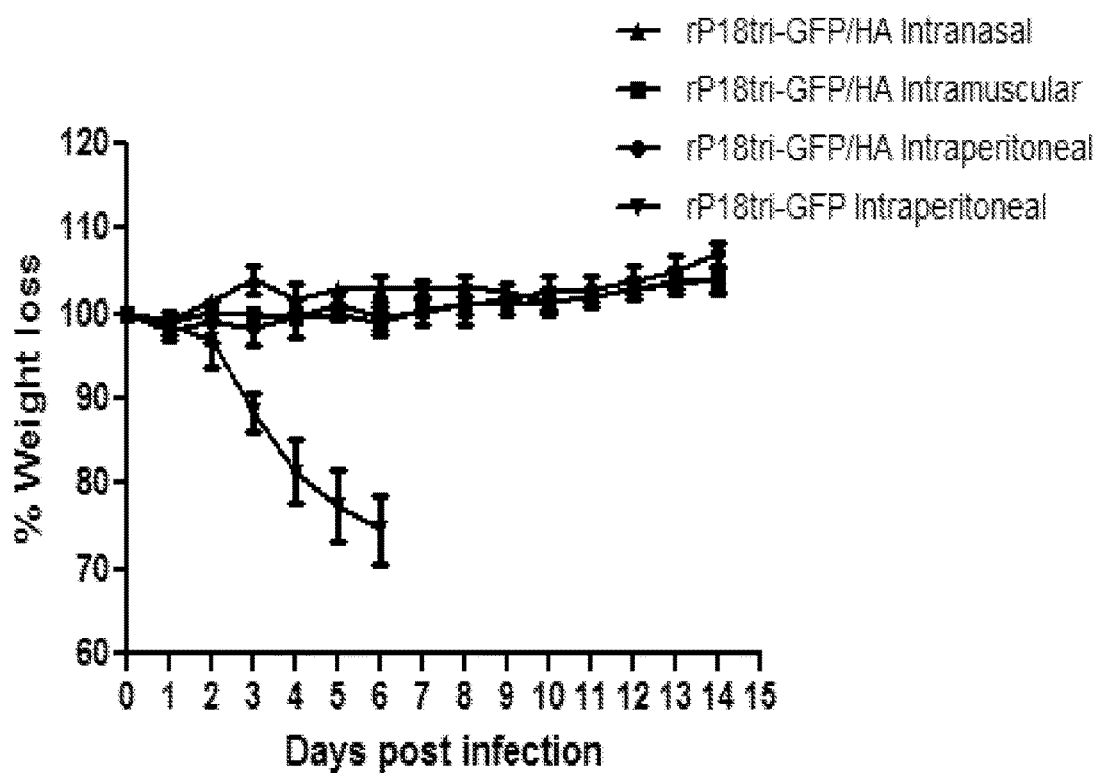
FIG. 10. Protection conferred by rP18tri-GFP/HA following different routes of vaccination.

HAI titers generated by different vaccination routes were compared (FIG. 9). Mice were vaccinated with rP18tri-GFP/HA by one prime and one boost via intraperitoneal (i.p.), intramuscular (i.m.), or intranasal (i.n.) route. All three routes of immunization elicited significant levels of humoral response as demonstrated by relatively high HAI titers overall. However, it appears that the HAI titres in sera of the i.m and i.p injected routes were relatively higher than those of the i.n. group. Regardless, these HAI titers were high enough to confer complete protection against a lethal challenge with the PR8 influenza virus. As shown in FIG. 10 there was no significant weight loss observed in the vaccinated animals.

5. The rP18tri-GFP/NP Vaccine Induces Strong CTL Responses in Mice.

Figure 11:
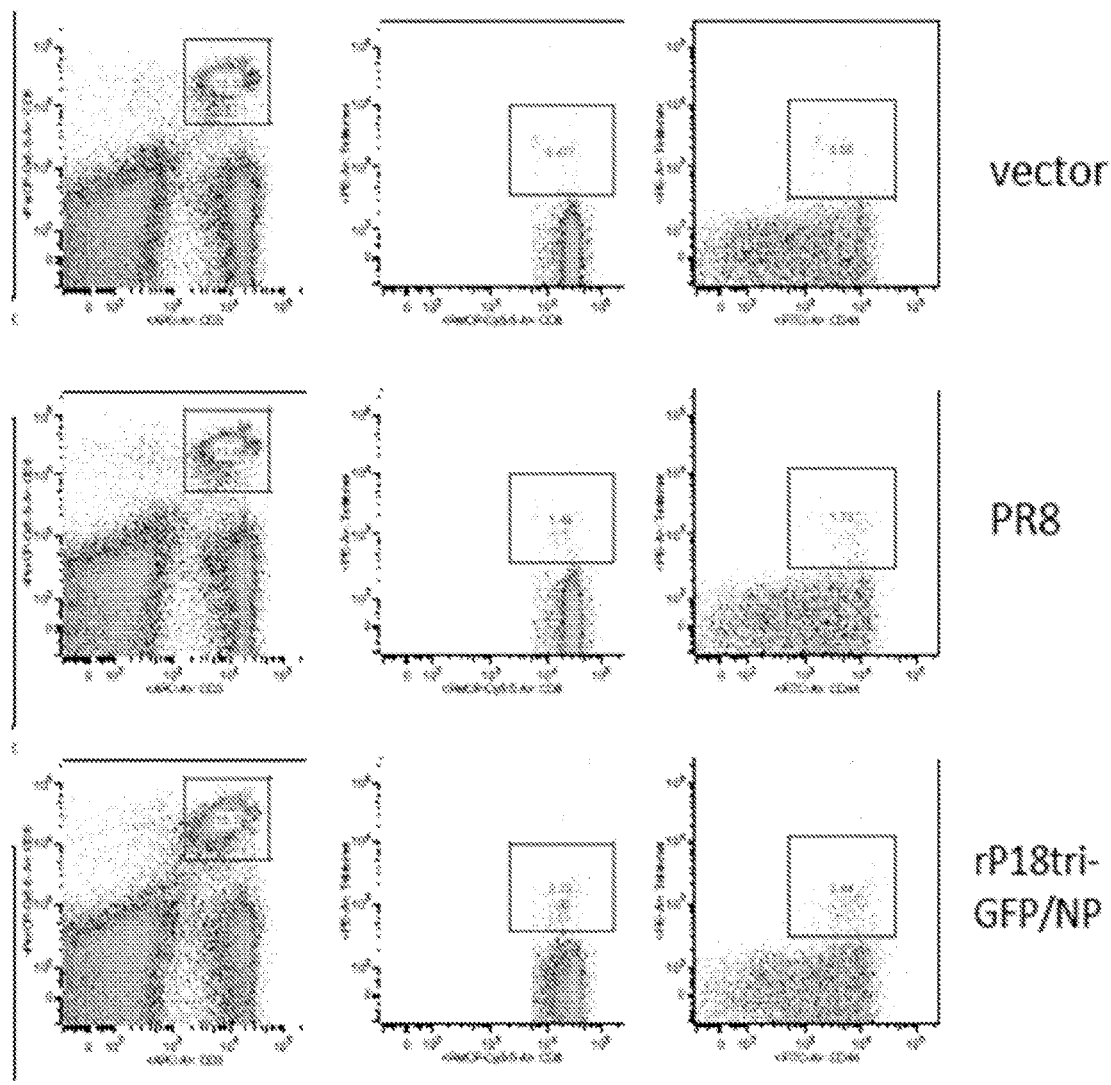
FIG. 11. Analysis of the NP-specific CTL responses by NP tetramer analysis.
Figure 12:
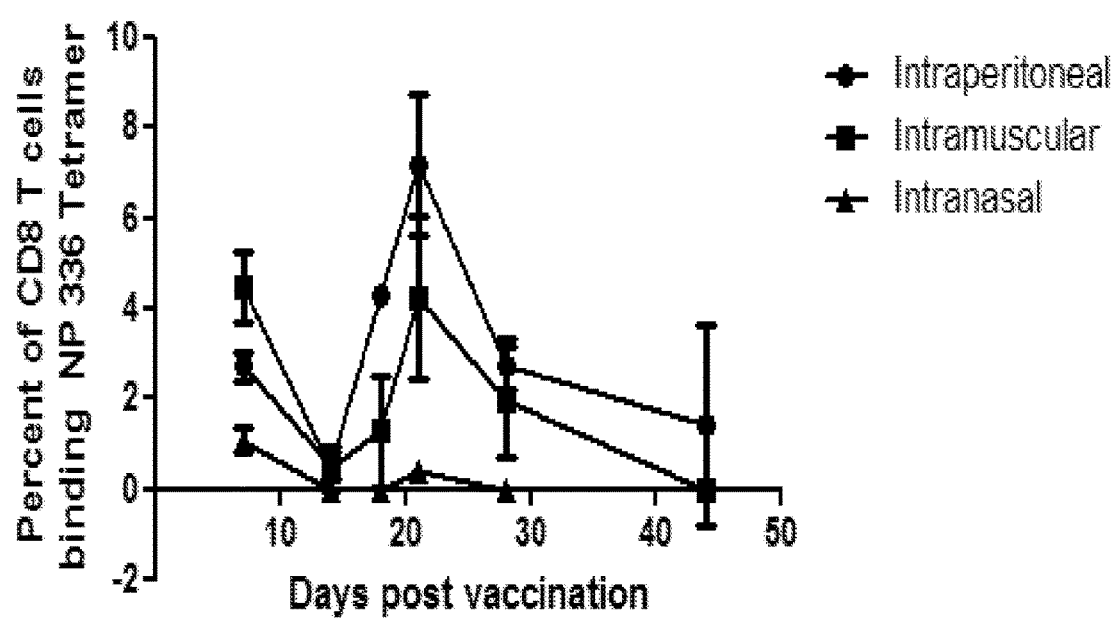
FIG. 12. Kinetics of CD8+ T cell responses elicited following different routes of vaccination.
Figure 14:
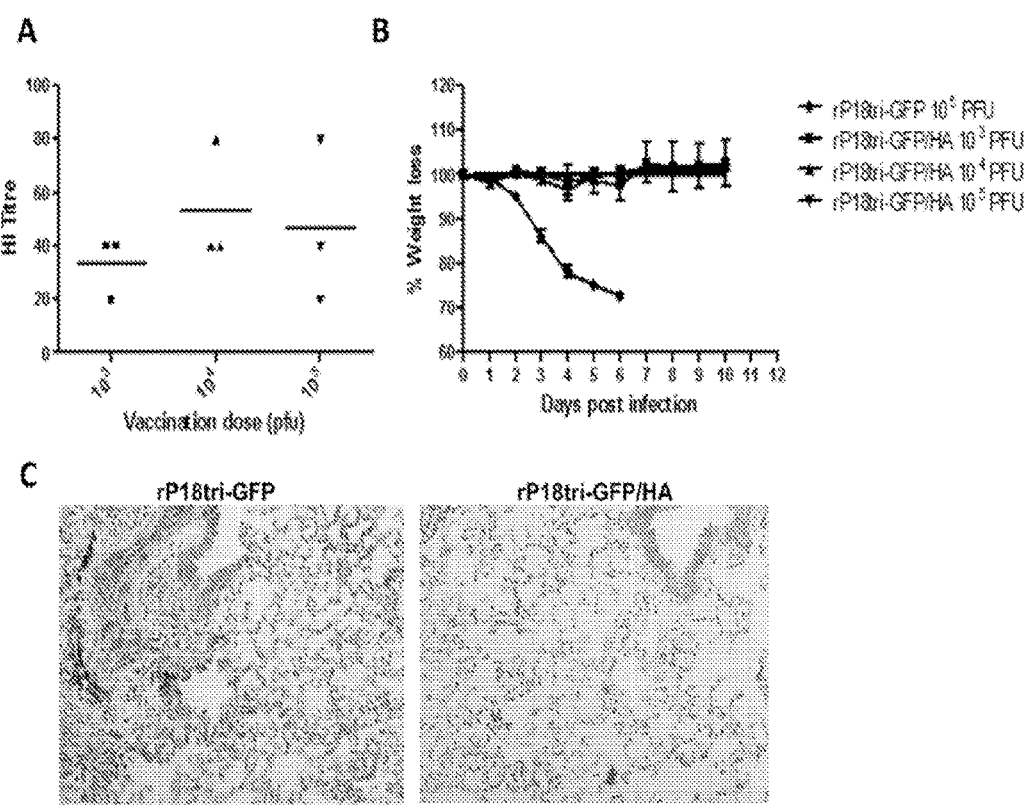
FIG. 14. Protection conferred by priming with the rP18tri-GFP/HA vaccine vector. A. Neutralizing antibody titres following different dosages of the rP18tri-GFP/HA vaccination. B. Percent weight loss. C. H&E stained lung sections.
Figure 16:
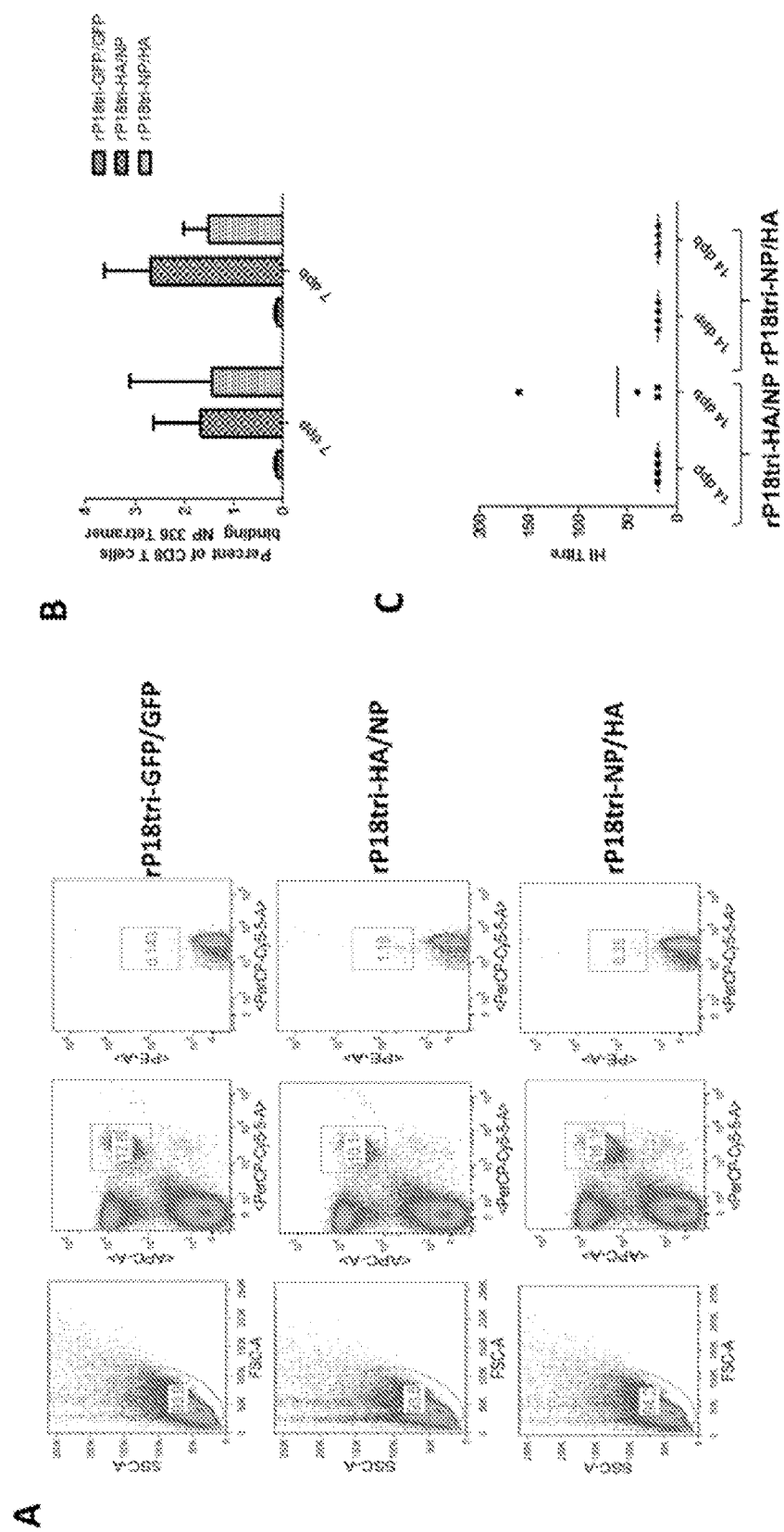
FIG. 16. T cell and humoral responses induced by vector expressing dual antigens (HA and NP). A. Representative FACS plots for $NP_{336}$ tetramer+ CD44+ CD8+ T cells in mouse blood at day 7 post-vaccination. B. Frequencies of NP specific CD8+ T cells in the peripheral blood tested 7 days post priming and 7 days after boosting by tetramer staining. C. Viral neutralizing antibody titres were determined using HI assay of sera collected at different time points.

NP is an intracellular viral protein and is known to induce CD8+ T cell response against it. Whether the rP18tri-GFP/NP vaccine can induce CTL responses was examined by conducting NP-specific tetramer analysis of splenic cells and PBMCs at different time points after prime and boost with rP18tri-GFP/NP intraperitoneally. As shown in FIG. 11 (top), NP-specific CD8+ and CD44+ T cells were detected in the rP18tri-GFP/NP vaccinated group even at 7 d post-prime, at comparable (if not higher) level to a low dose of PR8 infection, which increased further at 7 d post-boost, and were still present at 14 d post-boost (FIG. 11 middle). We also explored the effect of different inoculation routes on CTL responses. As shown in FIG. 12 both i.m. and i.p. inoculation routes induced stronger CTL responses than the i.n. route of infection. Collectively, our data demonstrate that rP18tri-based vector can induce strong CTL responses in vivo and that the intramuscular and intraperitoneal routes are better than intranasal route in inducing strong CTL responses. Since the i.m route elicited optimal humoral and T cell responses, subsequent experiments were conducted following the i.m route of immunization.

6. Can rP18Tri-Based Vaccine Trigger Long-Lasting Immunity?

Figure 13:
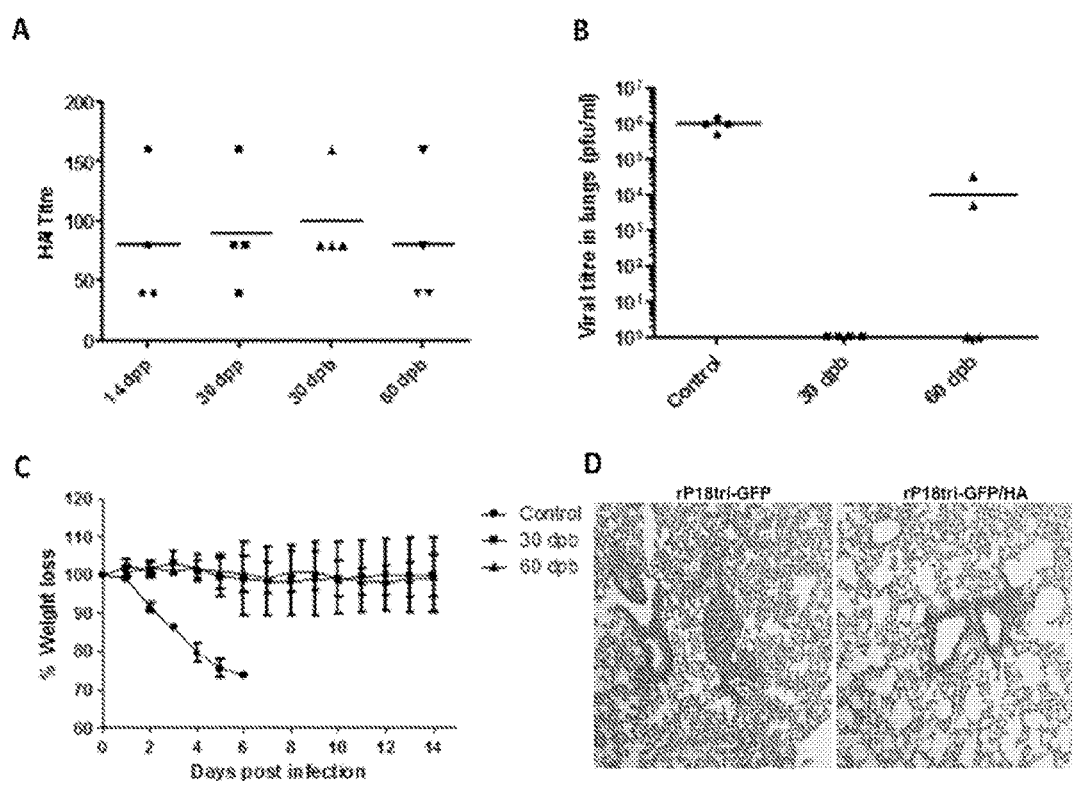

The potential of the rP18tri-GFP/HA vaccine vector to induce long lasting immunity was evaluated. C57BL6 mice were immunized twice at an interval of 4 wks and were challenged either 4 or 8 wks after second immunization with a lethal dose of the A/PR/8 (H1N1) virus. Serum samples analysed for HAI titres at days 14 and 30 post prime and days 30 and 60 post boost demonstrated a strong neutralizing antibody titer (FIG. 13A). The challenged virus A/PR/8 replicated well in the lungs of mock-vaccinated mice whereas there was no detectable virus titer in the lungs of vaccinated mice that were challenged after 4 wks of vaccination. However, there were significantly less viral titers in the lungs of immunized mice that were challenged after 8 wks of vaccination (FIG. 13B). As shown in FIG. 13C, complete protection was observed as there was no significant weight loss in the rP18tri-GFP/HA immunized mice challenged after either 4 wks or 8 wks of vaccination. Consistently, there were no significant pathological changes in the lungs of immunized mice (FIG. 13D). Overall, the levels of immunity and protection were comparable with those seen at 2 wks after immunization.

Single Immunization with rP18tri-GFP/HA Induced Protection Against Lethal H1N1 Challenge C57BL6 mice were immunized with rP18triGFP-HA through intramuscular route. Remarkably, a single dose of rP18tri-GFP/HA induced complete protection against lethal infection with the mouse-adapted A/PR/8 (H1N1) virus. As shown in FIG. 14B, rP18tri-GFP vaccinated control mice continued to lose weight after challenge until they required euthanasia. The results also demonstrated that a single immunization with a minimum dose of $10^3$ pfu of the rP18tri-GFP/HA vector elicited a robust hemagglutination inhibiting (HI) Ab response and was sufficient to confer protection (FIG. 14A). Histological analyses of the lung section conducted 5-6 days after challenge revealed a significant reduction in inflammation in mice vaccinated with rP18tri-GFP/HA whereas mice vaccinated with rP18tri-GFP showed massive infiltration of inflammatory cells into the lung, lung congestion and intra-alveolar edema (FIG. 14C).

Generation and Characterization of rP18tri-based Virus Expressing Dual Influenza Viral Protein Antigens To obtain the rP18tri-based vector expressing influenza HA and NP or HA1 and HA3, DNA encoding the respective influenza virus genes was inserted into plasmid vectors P18S-GPC/MCS and P18S-MCS/NP accordingly. The RT-PCR amplified HA1, NP and HA3 were cloned and each clone was sequence verified. The resulting plasmids were designated as P18S-GPC/HA1, P18S-NP1/NP and P18S-HA3/NP. The recombinant virus expressing dual antigens (influenza HA1 and NP1) was then rescued by co-transfecting 3 plasmids expressing the full-length P18 L agRNA segment, P18S-GPC/HA1 and P18S-NP1/NP. Simultaneously, a similar 3-segmented recombinant virus with swapped influenza genes was also generated by co-transfecting the full-length P18 L agRNA segment, P18S-GPC/NP1 and P18S-HA1/NP. Similarly, recombinant virus expressing dual antigens (influenza HA1 and HA3) was rescued by co-transfecting 3 plasmids expressing the full-length P18 L agRNA segment, P18S-GPC/HA1 and P18S-HA3/NP.

Interestingly, rP18tri-HA/NP had lower titres than rP18tri-NP/HA and formed smaller plaques in Vero cells (FIG. 15A). However, the expression level of the influenza viral protein antigens was higher in the rP18tri-HA/NP as compared to the rP18tri-NP/HA (FIG. 15B).

rP18tri-based Vector Encoding Multiple Influenza Viral Protein Antigens (HA and NP) Induced Both Humoral and T Cell Responses in Immunized Mice.

rP18tri-based vector encoding both influenza viral HA and NP successfully induced potent humoral and T cell responses in mice that were immunized with $10^4$ pfu/ml of either the rP18tri-HA/NP or rP18tri-NP/HA vector. Peripheral blood and spleen of mice were used to monitor the levels of T cell responses to immunodominant $NP_{336}$ epitope using an MHC class I tetramer. Anti-NP-specific CD8+ T cells were detected in peripheral blood and splenocytes of immunized mice. On day 7 post-immunization, mice had a significantly greater percentage of NP-specific T cells (FIG. 16A). Tetramer positive CD8+ T cells peaked after 7 days of boost and were maintained at a resting level until 14 days post boost (FIG. 16B). Both of the vaccine candidates also elicited a strong humoral response that was assessed by hemagglutination inhibition titre in sera collected at 14 days post prime and 14 days post boost. The HI titres were increased post boost in mice immunized with rP18tri-HA/NP whereas no such elevation was observed in mice immunized with the rP18tri-NP/HA (FIG. 16C).

Taken altogether, the rtriP18-HA/NP vaccine elicited a stronger immune response in comparison to the rP18tri-NP/HA vaccine. The better levels of immune response of the rP18tri-HA/NP could be attributed to a higher expression level of the influenza viral antigens (FIG. 15B). Nevertheless, both the vector vaccines rP18tri-HA/NP and rP18tri-NP/HA conferred complete protection against a lethal challenge of the A/PR/8 influenza virus. No disease symptoms were observed in the immunized mice. As shown in FIG. 17A, no significant histological changes could be detected in the lungs of mice immunized with either of the vaccine candidates. In contrast, infiltration of inflammatory cells was observed in lungs of mice vaccinated with the rP18tri-GFP. Viral titres in lungs were analyzed to determine the replication of the challenged virus at day 3 and 6 post infection. The mock-vaccinated mice showed high viral titres while mice vaccinated with the rP18tri-HA/NP and rP18tri-NP/

Figure 17:
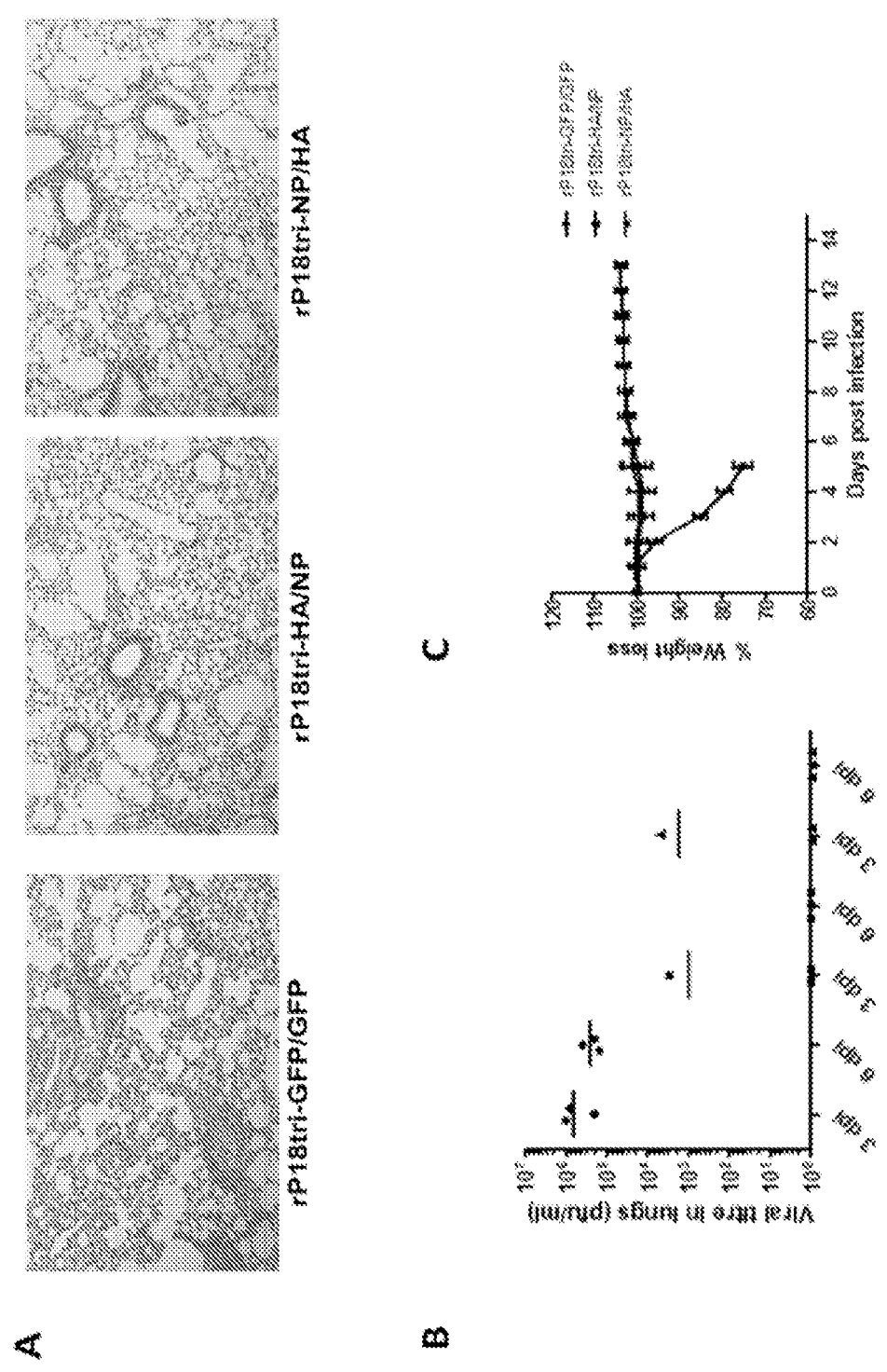
Figure 18:
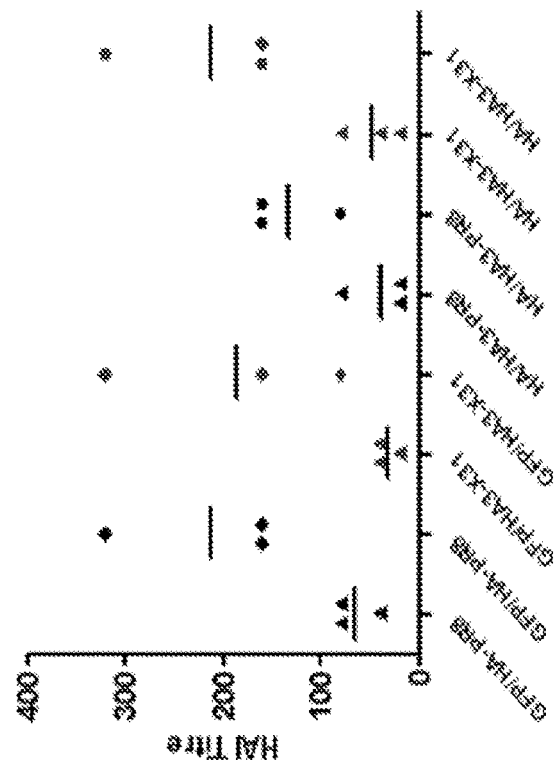
FIG. 18. Humoral response in C57BL6 mice and Balb/c mice induced by the rP18tri-based vector vaccine expressing HA proteins of both the H1N1 and H3N2 influenza virus subtypes. Mice were inoculated intramuscularly twice at an interval of 2 weeks between prime and boost, either with rP18tri-GFP/GFP or with $10^4$ pfu of rP18tri-GFP/HA, rP18tri-GFP/HA3 and rP18tri-HA/HA3. Two weeks after boosting, serum samples were collected and analysed for HI titres against the PR8 (H1N1) and X31 (H3N2) challenged viruses. Δ represents HI titre after 2 wks of priming and • represents HI titre after 2 wks of boosting. Left panel: HI titre in C57BL6 mice. Right panel: HI titre in Balb/c mice.
Figure 18:
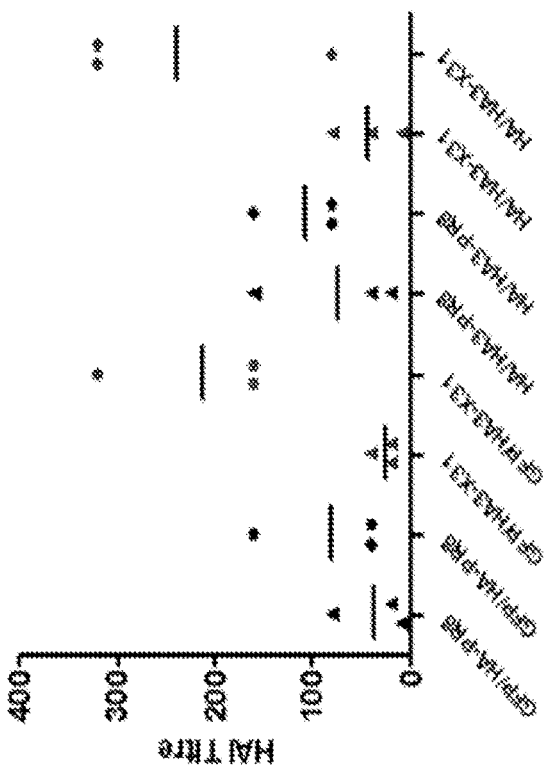
Figure 19:
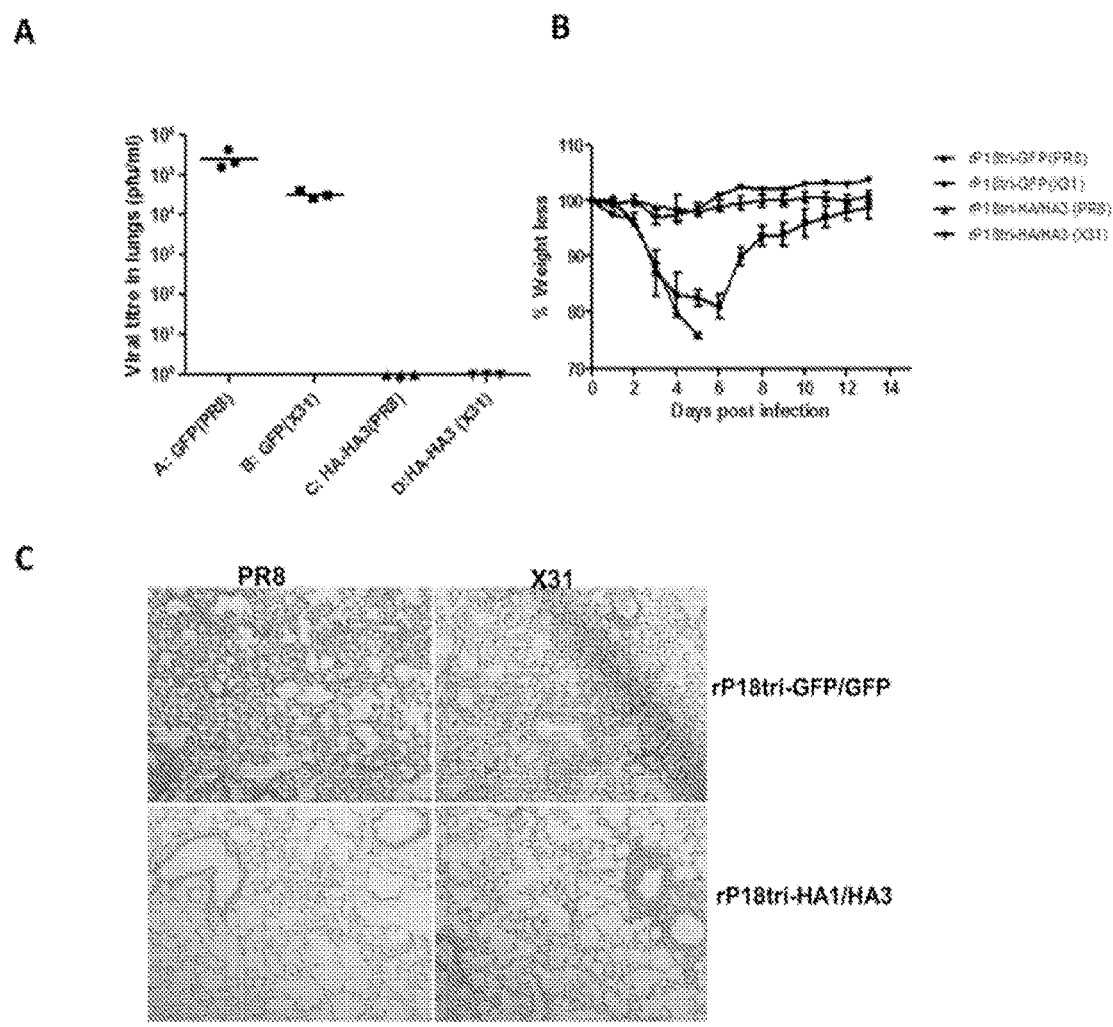
FIG. 19. Protection against dual influenza virus challenge. Mice were vaccinated with $10^4$ pfu/ml rP18tri-HA/HA3. Five or six days after virus challenge, virus titres in the lungs were determined. A. Graph shows viral titres when challenged with either the PR8 or X31 influenza virus. B. Weight loss after challenge with $10LD_{50}$ A/PR/8 or $10^5$ pfu X31. C. H&E stained sections of lungs harvested 6 days after challenge with $10LD_{50}$ of A/PR/8 virus and $10^5$ pfu of X31.

HA showed no detectable titres at day 6 and one out of three mice in each group showed titres of 3×10³ pfu/ml and 5×10³ pfu/ml respectively at day 3 post infection (FIG. 17B). Mice vaccinated with either of the vaccine candidate showed no weight loss (FIG. 17C).

rP18tri-based Vector Encoding Multiple Influenza Antigens (HA1 and HA3) Induced Protection Against Dual Challenges Different groups of C57BL6 female mice were immunized with two dosages of either the rtriP18-based vector vaccine encoding only HA of the H1-subtyped virus (rP18tri-HA1) or HA of the H3-subtyped (rP18tri-HA3) or both HA of the H1 subtype and the H3 subtype (rP18tri-HA1/HA3). The results indicated that the first dose of the rtriP18-based vector encoding HA1 and HA3 induced antibody responses to both the encoded influenza viral antigens as revealed by robust HI titres for PR8 and X31. The second dose of the vaccine further boosted the antibody response. Interestingly, the HI titres induced for PR8 (H1) and X31 (H3) by rP18tri encoding both HA1 and HA3 were comparable to that induced by the rtriP18-based vector encoding only HA1 or HA3 (FIG. 18A). Similar results were obtained in Balb/c mice (FIG. 18B). Upon challenge with a lethal dose of the PR8 (H1N1) or X31 (H3N2) virus, mice immunized with the rP18tri-based vector encoding both HA1 and HA3 (rP18tri-HA1/HA3) were protected against both viral challenges. The protective efficacy of the rP18tri-HA1/HA3 in preventing the replication of the challenged viruses was evaluated on day 5 following virus challenge. The challenged viruses PR8 (H1N1) and X31 (H3N2) replicated well in the lungs of mock-vaccinated mice with a mean titres of 10⁵ and 10⁴ pfu/ml respectively. Immunization with the rP18tri-HA1/HA3 protected mice from both of the viral challenges as there was no loss of body weight and none of the immunized mice had any detectable viral titres in the lungs (FIGS. 19A and B).

rP18tri-based Flu Vaccines do not Induce Anti-Vector Immunity.

A perceived weakness of live viral vector is the anti-vector immunity, which impairs the immune responses induced by the same vector and excludes its usage in a prime-boost vaccination strategy. PICV has little to no pre-existing immunity in general population (Trapido et al., 1971, Am J Trop Med Hyg 20:631-641). We determined the effect of anti-vector immunity against PICV vector by measuring the levels of antibody and CTL responses by prime-boost with the same vector. Surprisingly, we found no evidence for anti-vector immunity against rPICVtri vector. Shown in FIG. 8, boosting with the same vector further substantially increased the HAI titers, suggesting that HA-specific humoral responses increased after the $2^{nd}$ and even $3^{rd}$ boosting. Similar finding was observed for the CTL responses. The NP-specific CD8 and CD44 T cells in both spleen and PBMCs increased after boosting (FIG. 20). Taken together, our data suggest that rPICV vector does not induce strong anti-vector immunity and thus can be repeatedly used in the prime-boost vaccine strategy.

Summary

A novel PICV reverse genetic system has been developed to generate tri-segmented recombinant PICV viruses that can encode up to two foreign genes of interest. These rP18tri-based recombinant viruses can express the influenza HA and/or NP genes along with the GFP reporter gene in target cells. When tested in mice, the rP18tri-GFP/HA virus can induce high levels of HA-specific neutralizing antibodies, while the rP18tri-GFP/NP virus can induce strong NP-specific CTL responses. In addition, the rP18tri-based vector expressing dual influenza viral antigens HA and NP successfully induced both humoral and T cell responses that conferred complete protection in immunized mice against a lethal challenge with the A/PR8. More importantly, the triP18-based vector expressing HA of two different influenza virus subtypes i.e PR8 (H1N1) and X31 (H3N2) conferred protection against both of the viral challenges, demonstrating the prowess and versatility of these novel vaccine vectors against pathogenic influenza viruses. It is also important to note that there is no pre-existing immunity against PICV vector and that animals immunized with the tri-segmented PICV viruses generate little anti-PICV vector immunity, making this an ideal vector vaccine platform for inducing potent, long-lasting and cross-reactive immunity upon repeated vaccination in the event that a prime-boost vaccination strategy is needed.

Example 2

The Biological Role of NP Exoribonuclease in Arenavirus Infection In Vitro and In Vivo Arenavirus NP RNase activity is important for type I interferon (IFN) suppression but its biological role(s) have not been well characterized. Recombinant Pichinde viruses with RNase catalytic mutations induced high levels of IFNs and grew poorly in IFN-competent cells, and, when infecting guinea pigs, stimulated strong IFN responses, failed to replicate productively, and generated wild-type revertants. Thus, the NP RNase activity is essential for the IFN suppression and establishing productive replication early in arenavirus infection.

Figure 21:
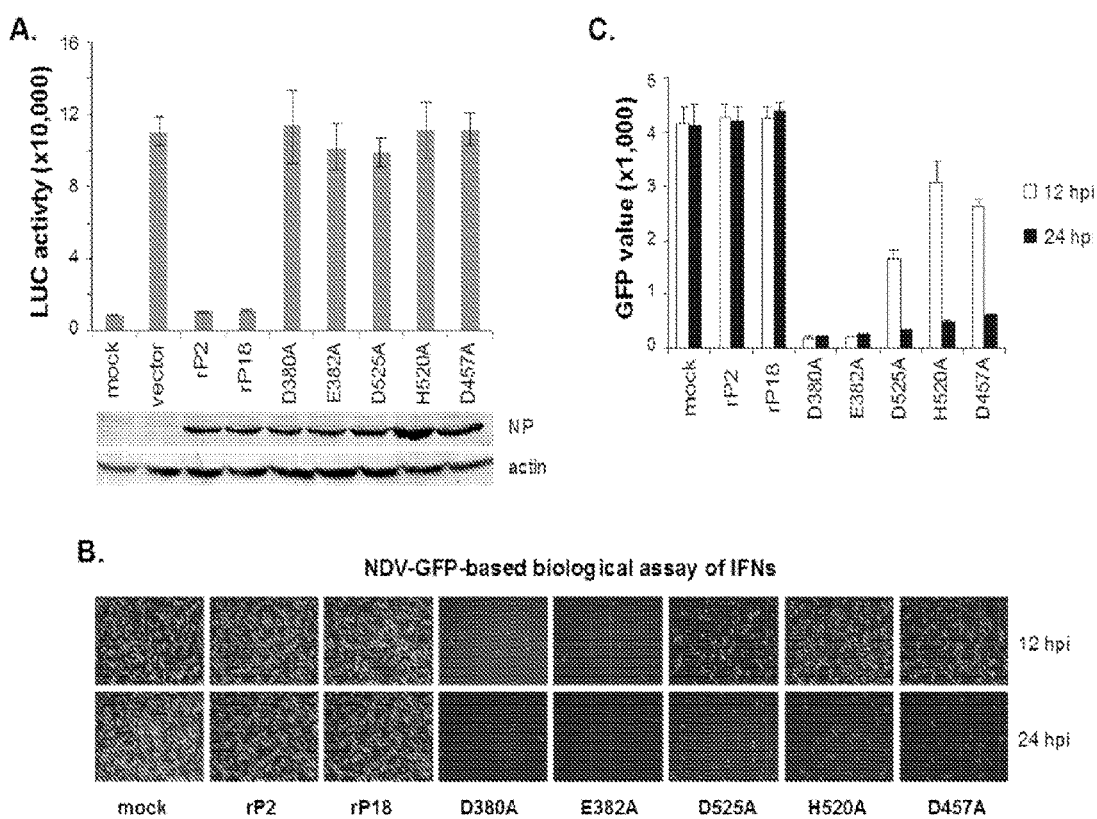
FIG. 21. Recombinant NP RNase mutant viruses induced type-I IFNs production in infected cells. (A) Alanine-substitution mutations at each of the 5 catalytic residues abolished the ability of PICV NP to suppress the Sendai virus-induced IFNβ activation (Qi et al., 2010, Nature 468:779-783). 293T cells were transfected with an IFNβ promoter directed-LUC plasmid and the β-gal plasmid, together with an empty vector or the respective NP plasmids, followed by Sendai virus infection. LUC activity was measured and normalized for transfection efficiency by β-gal activity. The results shown are the average of three independent experiments. Expression of the WT (rP2 and rP18) and mutant PICV NP proteins was detected by Western blotting using anti-myc antibody. (B) Recombinant PICV RNase mutant viruses produced high levels of type I IFNs upon viral infection. A549 cells were mock infected or infected with the respective recombinant PICV viruses at MOI of 1. Supernatants were collected at 12 and 24 hpi, UV-treated to inactivate viral particles, and subjected to the rNDV-GFP-based biological assay to measure the level of IFNs. Representative GFP images (B) and the average GFP values with standard deviations from three independent experiments (C) are shown.

Arenaviruses include several hemorrhagic fever (HF)-causing agents (e.g., Lassa virus—LASV), with limited preventative or therapeutic measures (McLay et al., 2013, Antiviral Res 97:81-92, McLay et al., 2014, J Gen Virol 95:1-15). Arenavirus pathogenesis is associated with high viremia and generalized immune suppression, the mechanism of which is poorly understood. It has been shown that viral NP can effectively mediate Type-I IFN suppression via its exoribonuclease (RNase) function (Jiang et al., 2013, J Biol Chem 288:16949-16959, Martinez-Sobrido et al., 2007, J Virol 81:12696-12703, Martinez-Sobrido et al., 2006, J Virol 80:9192-9199, Qi et al., 2010, Nature 468:779-783, Hastie et al., 2011, Proc Natl Acad Sci USA 108:2396-2401, Hastie et al., 2012, PLoS ONE 7:e44211). However, the role of the NP RNase activity in mediating host immune suppression in vivo has not been well characterized. In this study, Pichinde virus (PICV) infection of guinea pigs was used as a surrogate model of arenavirus hemorrhagic fevers (HFs) (Aronson et al., 1994, Am J Pathol 145:228-235, Lan et al., 2009, J Virol 83:6357-6362) to characterize the role of the NP RNase in viral infection and host IFN responses. Single alanine substitution at each of the RNase catalytic residues (D380A, E382A, D525A, H520A, and D457A) could abolish the NP ability to suppress Sendai virus-induced IFNβ activation by a luciferase (LUC) reporter assay (FIG. 21A), corroborating our previous observations with LASV NP (Qi et al., 2010, Nature 468:779-783). Using our developed rP18 PICV reverse genetics system (Lan et al., 2009, J Virol 83:6357-6362), we successfully generated recombinant viruses carrying individual RNase mutations, which were confirmed by sequencing. The 5 RNase mutants, together with the WT rP18 that causes virulent infection in guinea pigs, and PICV rP2 that causes avirulent infection, were used to infect human airway epithelial A549 cells at MOI=1. Type-I IFN productions at 12 hpi and 24 hpi were quantified by the rNDV-GFP biological assay (Park et al., 2003, J Virol 77:1501-1511). Both rP2 and rP18 produced low levels of IFNs similar to mock infection, as demonstrated by the high levels of GFP expression (FIG. 21B). This is not surprising as NP proteins of both strains encode a functional RNase domain and do not seem to differ in their ability to suppress IFN production (Lan et al., 2008, Arch Virol 153:1241-1250). In contrast, the RNase mutants produced significantly more IFNs, as shown by the greatly reduced GFP expression (FIG. 21B). Thus, the NP RNase activity is required for the efficient inhibition of type I IFNs in virus-infected cells.

Figure 22:
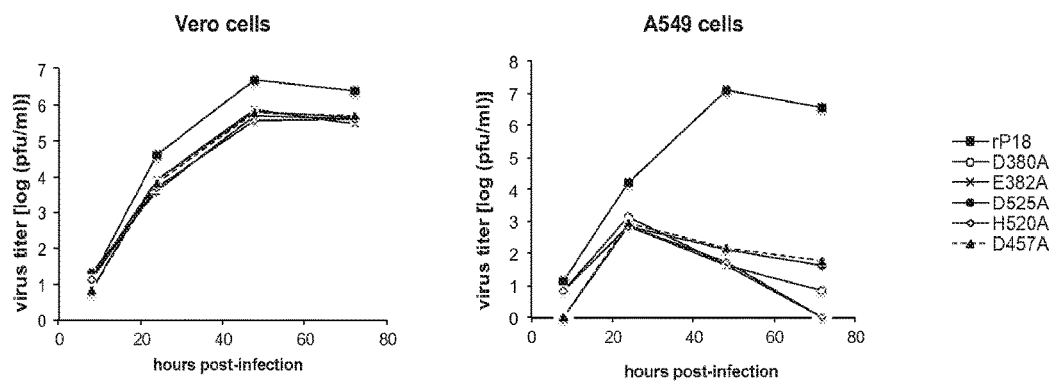
FIG. 22. The NP RNase activity is required for PICV replication in the IFN-competent cells in vitro and PICV infection in vivo. (A) Viral growth kinetics in the IFN-defective Vero and IFN-competent A549 cells. Cells were infected with the respective viruses at MOI of 0.01. At different times post infection, virus titers in the supernatants were quantified by plaque assay. The results shown are the average of three independent experiments. (B) Survival rate (left panel) and the normalized body weight (right panel) of guinea pigs (n=6) infected with the respective recombinant PICV viruses. Statistical analyses of the survival curves were performed using the Log-rank (Mantel-Cox) $\chi^2$ Test using GraphPad prism 5 software. *, $p<0.001$. , $p<0.01$.
Figure 22:
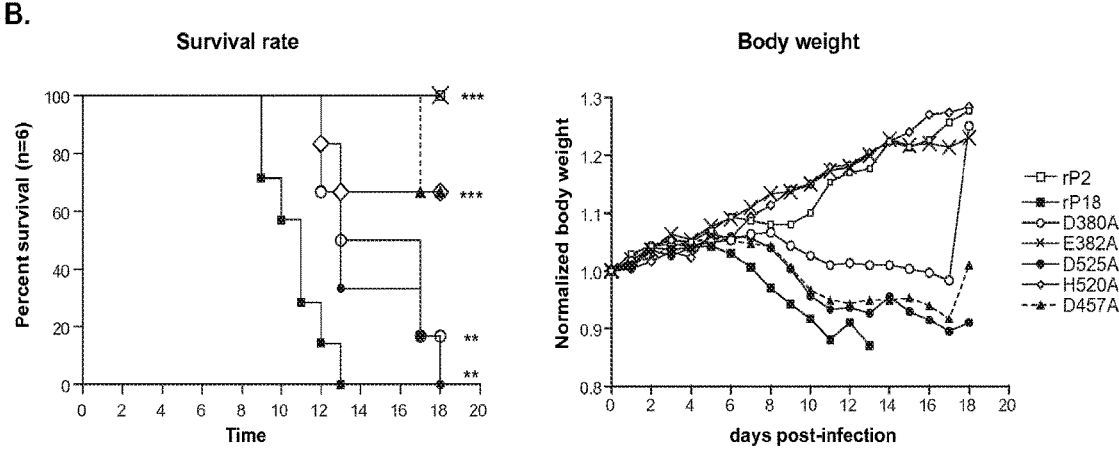

Viral growth kinetics was determined in the IFN-deficient Vero cells and IFN-competent A549 cells at moi=0.01. All 5 mutants replicated well in Vero cells, reaching $10^6$ pfu/ml at 48 hpi, albeit at ~0.5-1 log lower than the WT rP18 (FIG. 22A, left). In sharp contrast, these RNase mutant viruses barely grew in A549 cells (FIG. 22A, right). Our results suggest that the NP RNase activity is non-essential for the basic virus life cycle but is required for productive viral replication in the IFN-competent cells, consistent with the recently published data on the LASV double-mutant (D389A/G392A) (Carnec et al., 2011, J Virol 85:12093-12097).

To compare viral virulence in vivo, we infected 6 Hartley outbred guinea pigs intraperitoneally with $1 \times 10^4$ pfu of each virus as previously described (Lan et al., 2009, J Virol 83:6357-6362, Kumar et al., 2012, Virology 433:97-103, McLay et al., 2013, J Virol 87:6635-6643). All procedures were approved by the Institutional Animal Care and Use Committee (IACUC) at University of Minnesota. Animals were monitored daily for body weight and disease signs for up to 18 days, and were euthanized when they reached the predetermined terminal points (moribund), such as more than 30% weight loss compared to a nomogram or rectal temperature below 38° C. in combination with continuing weight loss. As expected, all rP2-infected animals survived and cleared the virus, while rP18-infected animals developed early onset of fever, showed significantly decreased body weight starting at 7 dpi, and reached terminal points by 13 dpi (FIG. 22B). The RNase mutant viruses caused variable disease outcomes (FIG. 22B and Table 1). All E382A mutant virus-infected animals survived without any evidence of body weight loss, while animals infected with each of 3 other mutant viruses (D525A, H520A, and D457A) showed various degrees of attenuation (FIG. 22B). Most D380A-infected animals, however, succumbed to the infection albeit at a later time point than the rP18. To determine whether WT revertants occurred, we measured the viremia levels at end point and sequenced the viruses (Table 1). As expected, moribund animals were associated with high viremia while all those who survived had very low to undetectable levels of virus infection. Without exception, viruses isolated from mutants-infected animals had reverted back to the WT NP sequence (Table 1). This is highly unlikely due to PCR contamination or sequencing error as the viruses isolated from other mutant virus-infected animals conducted at the same time still contain the expected mutations (data not shown). We therefore believe that the disease phenotypes are caused by WT viruses, including the WT revertants, and that the disease severity is determined by how fast the reversion occurs in vivo (a few surviving animals were found to carry low levels of WT virus at day 18). Our results strongly suggest an essential role of the NP RNase activity in arenaviral infection in vivo.

TABLE 1

Guinea pigs infected with the respective recombinant PICVs.

| Recombinant PICV strains | Disease | Viremia[1] (PFU/ml) | Viral sequences[2] |
|---|---|---|---|
| rP2[3] | survived | ND[4] | |
| rP18 | moribund | 2.00E+06 | |
|  | moribund | 5.80E+05 | |
|  | moribund | 2.80E+05 | |
|  | moribund | 1.80E+06 | |
|  | moribund | 2.30E+05 | |
|  | moribund | 8.00E+05 | |
| D380A | moribund | 5.00E+04 | WT reversion |
|  | moribund | 3.10E+05 | WT reversion |
|  | moribund | 3.30E+06 | WT reversion |
|  | moribund | 1.60E+04 | WT reversion |
|  | moribund | 5.00E+04 | WT reversion |
|  | survived | ND | |
| E382A | survived | ND | |
|  | survived | 2.13E+03 | WT reversion |
|  | survived | ND | |
|  | survived | 9.00E+02 | WT reversion |
|  | survived | ND | |
|  | survived | ND | |
| D525A | moribund | 7.50E+04 | WT reversion |
|  | moribund | 6.25E+04 | WT reversion |
|  | moribund | 1.75E+05 | WT reversion |
|  | moribund | 1.40E+04 | WT reversion |
|  | moribund | 2.40E+04 | WT reversion |
|  | moribund | 2.10E+05 | WT reversion |
| H520A | moribund | 5.75E+05 | WT reversion |
|  | survived | ND | |
|  | moribund | 7.50E+05 | WT reversion |
|  | moribund | ND | |
|  | moribund | ND | |
|  | moribund | ND | |
| D457A | survived | ND | |
|  | survived | ND | |
|  | survived | ND | |
|  | survived | 6.20E+02 | WT reversion |
|  | moribund | 5.50E+04 | WT reversion |
|  | moribund | 1.10E+05 | WT reversion |

[1]Virus titers in the blood collected at the time of euthanization when animals reached terminal points or at day 18 post infection.
[2]Sequences of viruses isolated from animals at the time of euthanization when animals reached terminal points or at day 18 post infection.
[3]All 6 animals in the rP2-infected group survived with no detectable viremia at day 18 post infection.
[4]ND, not detectable by plaque assay To examine the role(s) of RNase in early viral infection and host innate immune responses in infected animals, we monitored viral spread and quantified innate antiviral genes at 1 dpi and 3 dpi. At day 1, viruses were detected at low levels in the livers and spleens of rP18-infected animals and in the livers of some animals infected with rP2 and the RNase mutant viruses (FIG. 23A). At day 3, both rP18 and rP2 replicated to relatively high levels in both livers and spleens. In contrast, RNase mutant viruses appeared to be cleared from the livers and only detected in a few spleens at very low levels (FIG. 23A), Representative innate immune response genes, IFN-α1, IFN-β1, ISG15, IRF7, RIG-I, and MDA5, in the peritoneal cavity cells at day 1 were quantified by qRT-PCR (FIG. 23B). These genes were highly activated by the RNase mutant viruses but not by the WT viruses (rP2 and rP18), demonstrating that NP RNase is required for arenavirus-induced innate immune suppression in vivo.

In summary, our study with recombinant PICV RNase mutants has not only confirmed the important role of NP RNase in type I IFNs suppression and viral replication in vitro, but also provided unequivocal evidence for its essential role in early innate immune suppression to allow establishment of a productive infection in vivo. Given that the NP RNase-dependent IFN suppression mechanism is conserved among arenaviruses (Jiang et al., 2013, J Biol Chem 288:

16949-16959), our results can be extrapolated to other arenaviral pathogens and implicate NP RNase as an ideal target for antivirals development.

Example 3

The Arenavirus-Based Vaccine Vector Delivers Two Antigens and Confers Immunity to Each of the Antigens 1. Generation of rP18tri Live Vaccine Vectors Expressing Dual Influenza Antigens HA and NP Example 1 discloses a replication-competent tri-segmented rPICV system (rP18tri) and using this rP18tri vector to express either the influenza HA (abbreviated as H) or NP antigen (P), it was demonstrated that the vector can induce strong antibody and CTL responses in mice. To determine whether a single rP18tri virion particle can be used to deliver both HA and NP genes, S1 and S2 viral genomic RNA segments were generated to encode the influenza HA and NP genes, respectively. By using different combinations of plasmids in the transfection reactions, we have successfully generated live vaccine vectors, rP18tri-P/H and rP18tri-H/P, which encode HA and NP genes on different S segments as illustrated in FIG. 24A. As a control vector, the rP18tri vector encoding the eGFP reporter gene on both the S1 and S2 segments—rP18tri-G/G—was also generated. To examine the antigens expression, Vero cells were infected with rP18tri-G/G, rP18tri-P/H, and rP18tri-H/P respectively. At 24 hpi, cells were examined for the expression of HA and NP by IFA using the mouse anti-HA and anti-NP antibodies, respectively, followed by detection with a PE-conjugated anti-mouse antibody. Expression of both HA and NP proteins was detected in cells infected with rP18tri-P/H and rP18tri-H/P but not in those infected with the vector control rP18tri-G/G. The lower number of cells expressing HA and NP by the rP18tri-H/P infection than by the rP18tri-P/H is due to a lower viral titer used in the infection (FIG. 24B). Subsequent viral growth analysis in BHK-21 cells at moi of 0.01 suggests that rP18tri-P/H and rP18tri-H/P replicate at similar kinetics and are <0.5 log lower than the vector control rP18tri-G/G (FIG. 24C).

2. The HA/NP Dual Antigen Vaccine Vectors can Induce Protective Immunity in Mice.

To test the protective immunity of rP18tri-P/H and rP18tri-H/P live vectors in vivo, we immunized a group of mice (n>=3) with the rP18tri-G/G control vector, rP18tri-P/H, or rP18tri-H/P at $1 \times 10^4$ pfu through the IM route, boosted with the same vectors 14 days later, and challenged with a lethal dose of the mouse-adapted A/PR8 influenza virus ($10 \times MLD_{50}$) 14 days after vaccination. All the control vector-immunized mice succumbed to the infection by day 6, while all mice receiving rP18tri-P/H or rP18tri-H/P survived the challenge without any disease signs or body weight loss (FIG. 25A). Compared to the control vector-immunized mice that had high viral titers ($2-10 \times 10^5$ pfu/g) in the lungs at 3 and 6 dpi, the rP18tri-P/H or rP18tri-H/P-immunized mice (n=3 in each group) had no detectable viruses at 6 dpi and only one of three had a relatively low level of viruses ($<5 \times 10^3$ pfu/g) at 3 dpi (FIG. 25B). Our data suggest that the dual antigen expressing viral vectors can induce strong protective immunity against influenza virus, which is conferred by HA-specific neutralizing antibody.

3. The H1/H3 Dual Antigen Vector Induces Balanced HA Neutralizing Antibodies.

Whether two different HA subtypes can be used to induce neutralizing antibodies at equal efficiency was determined. Toward this end, we have cloned the H3 HA gene of the A/x31 (H3N2 subtype of the influenza virus) to the S2 segment and when transfected with the full-length L segment, and the S1 segment encoding the H1 HA of A/PR8, live rP18tri-H3/H1 vector can be generated (FIG. 26A). As controls, we have also generated the rP18tri vectors encoding eGFP on the S2 segment and either H1 or H3 on the S1 segment, respectively called rP18tri-G/H1 or rP18tri-G/H3 (FIG. 26A). To test their immunogenicity, groups of C57BL6 mice (n=3 per group) were primed and boosted with the three vectors respectively at a 14-day interval through the IM route. Blood collected 14 days after prime and boost were measured for the levels of neutralizing antibody against A/PR8/H1N1 and A/x31/H3N2 (FIG. 26B top panel). The rP18tri vectors encoding single HA subtypes, rP18tri-G/H1 and rP18tri-G/H3, each induced strong homosubtypic neutralizing antibodies that increase over a boost dose, but did not induce detectable levels of cross-reactive antibodies after prime or boost. The rP18tri-H1/H3 dual antigen vector induced both H1 and H3 neutralizing antibodies that increased upon a booster dose and that the level of each neutralizing antibody was comparable to that induced by the respective single antigen vectors (FIG. 26B top). Similar findings were obtained with Balb/c mice (FIG. 26B bottom). Taken together, our data strongly suggest that the H1/H3 dual antigen vector induces balanced neutralizing antibodies against both antigens in mice. In other words, there is no preference (skewing) of production of neutralizing antibodies against one or the other HA antigen.

4. Induction of Heterosubtypic Neutralizing Antibodies by a Prime-and-Boost Strategy with Different HA Subtypes Recent studies have suggested that broadly neutralizing antibodies can be generated by prime-and-boost vaccinations or sequential infections (Wei et al., 2010, Science 329:1060-1064, Wei et al., 2012, Sci Transl Med 4:147ra114, Miller et al., 2013, Sci Transl Med 5:198ra107, Wrammert et al., 2011, J Exp Med 208:181-193, Krammer et al., 2012, J Virol 86:10302-10307, Miller et al., 2013, J Infect Dis 207:98-105, Margine et al., 2013, J Virol 87:4728-4737). As the rP18tri vector enhances immune responses upon a booster dose, whether it can induce cross-reactive immunity using a prime and boost strategy with different HA subtypes was tested. Toward this end, live rP18tri-P/H1 and rP18tri-P/H3 vectors were generated, each encoding A/PR8 NP, a conserved viral protein (see GenBank Accession number NP_040982.1) that is known to elicit T cell responses, together with either H1 (A/PR8) or H3 (x31) HA (FIG. 27A). Mice were primed with rP18tri-P/H1, boosted with rP18tri-P/H3, and boosted again with rP18tri-P/H1, each time at a 14-d interval. As expected, NP-specific CTLs were detected after prime (7 dpp), significantly increased upon a booster dose (7 dpb), and still remained at high levels (3-5%) after a second booster dose (FIG. 27B). Blood were collected 14 days after each administration and tested for the levels of neutralizing antibodies against A/PR8, A/x31, and A/WSN. Neutralizing antibodies specific to homologous viruses A/PR8 (H1) and A/31 (H3) were highly induced upon the exposure of the same HA antigens and were not generally enhanced by the heterologous HA boosting, whereas neutralizing antibodies against heterosubtypic virus A/WSN (H1) were steadily increased upon the booster doses (FIG. 27C). These immunized mice showed a significantly improved survival after a lethal challenge with the heterosubtypic virus A/WSN (FIG. 27D). Taken together, our data suggest that prime-and-boost with heterologous HA subtypes using the rP18tri vector can elicit cross-reactive neutralizing antibodies and cause cross protection against heterosubtypic influenza virus challenge.

5. The rP18tri Vector can Induce Both Humoral and T Cell Responses Through Oral Route.

To determine whether the rP18tri vector can be conveniently given through oral route, C57BL6 mice were immunized with $1\times10^4$ pfu of the rP18tri-G vector (n=3) or rP18tri-P/H (n=4) through oral gavage and boosted with the same vector 42 days later. The NP tetramer-positive effector T cells (CD8$^+$ CD44$^{high}$) at 7 days post prime and post boost were measured by the established NP tetramer analysis. At 7 days post prime, two out of three tested mice from the rP18tri-P/H-immunized mice had NP$^+$ CD8$^+$ CD44$^{high}$ cells (1.24% and 0.55%) that were clearly higher than the background level seen in the vector-immunized mice (0.13% and 0.09%). The NP-specific effector cells increased significantly at 7 days post boost, ranging from 5.7 to 7.1% in all 4 immunized mice (FIG. 28A). Similar patterns were observed for the neutralizing antibodies. Two out of four immunized mice showed a positive HAI titer (HAI=20) at 14 days post-prime. At 42 days post-prime, all 4 mice showed HAI titers in average of 40. After a boost dose, the HAI titer increased significantly for all 4 mice, ranging from 80 to 160 (FIG. 28B). Taken together, our data strongly suggest that the rP18tri vector can induce high levels of both humoral and T cell responses through oral route after a booster dose.

6. Inactivated rP18tri Vector can Induce both Humoral and T Cell Responses.

Whether inactivated rP18tri vector can induce vaccine immunity was determined. Live or hydrogen peroxide-treated rP18tri-P/H vaccine vector (i.e., inactivated vaccine vector) was used to immunize mice in 2 doses at a 34-day interval. Neither neutralizing antibodies nor NP-specific T cells were detected immediately after prime (7 days post-prime, 7 dpp). However, high levels of NP-specific effector T cells were detected after a booster dose (7 days post-boost, 7 dpb) with the inactivated vaccine vector (FIG. 29, left). Neutralizing antibodies were detected at a low level (HAI=20) in all three mice 34 days after prime (34 dpp), and increased significantly after a booster dose (14 days post-boost, 14 dpb), ranging from 40 to 80 with the inactivated vaccine vector (FIG. 29, right). It is worth noting that the levels of both T cell and humoral responses induced by the chemically inactivated rP18tri-P/H vaccine vector are significantly lower than those induced by the live vaccine vector. Nevertheless, that the inactivated rP18tri-P/H can still induce both humoral and T cell responses after a booster dose suggests the versatility of this viral vector as a vaccine platform as both a live and inactivated vaccines.

7. The rP18tri Vector Induces Protective Immunity Against Virulent P18 Virus in a Guinea Pig Model.

WT P18 virus was obtained after serial passages of the Pichinde virus (PICV) in guinea pigs and causes a hemorrhagic fever-like disease in the animals, which has been used as a safe surrogate model for studying pathogenesis of Lassa fever virus infection in humans (Jahrling et al., 1981, Infect Immun 32:872-880, Aronson et al., 1994, Am J Pathol 145:228-235, Liang et al., 2009, Ann NY Acad Sci 1171 Suppl 1:E65-74). Compared to WT P18 virus, the tri-segmented rP18tri vectors grow at least 1 log lower in vitro. We also determined the virulence potential of the rP18tri-G vector in guinea pigs. Guinea pigs infected with $1\times10^4$ pfu of rP18 virus developed early onset fever, rapidly lost weight after 7 days post-infection, and reached terminal points by day 14 (FIG. 30A). In contrast, guinea pigs infected with $1\times10^6$ pfu of rP18tri-G (100-fold higher titer than rP18 control) showed a similar body weight growth as the mock-infected animals and did not experience fever of more than 1 day (FIG. 30A).

Whether this non-pathogenic rP18tri vectors could induce protective immunity against a lethal rP18 challenge in guinea pigs was determiend. Guinea pigs were injected with either phosphor buffer saline (PBS) to represent mock infection or with $1\times10^4$ pfu of rP18tri-G through IP route and, 14 days later, challenged with a lethal dose of rP18 virus. PBS-immunized guinea pigs (n=3) soon developed fevers and lost body weight significantly and all animals reached predetermined terminal points by day 11 (FIG. 30B). In contrast, rP18tri-G-immunized guinea pigs (n=3) were completely protected with no appreciable body weight loss (FIG. 30B). The protective immunity against PICV is likely mediated by T cell responses as neutralizing antibodies have yet to develop at the time of challenge. Previous studies have demonstrated the cross-protection among different arenaviruses, such as LCMV and PICV, Lassa and Mopeia virus, Junin and Tacaribe complex viruses, and that apathogenic arenaviruses have been explored as live vaccines (reviewed in Olschlager et al., 2013, PLoS Pathog 9:e1003212). We propose that the rP18tri vector incorporating protective T cell epitopes into PICV proteins can induce cross-protective immunity against other arenavirus pathogens. With a capacity of encoding up to two additional antigens, the rP18tri vector can be developed as a dual (or triple) vaccine vector against both arenavirus pathogen and other desired pathogen(s).

In summary, a novel Pichinde virus (PICV)-based live viral vector rP18tri was developed that packages 3 RNA segments and encodes 2 foreign protein antigens. The viral vector was attenuated in vitro and in vivo. Using influenza HA as a model antigen, rP18tri-G/H can induce long-lasting protective immunity in mice. The rP18tri vector can induce strong humoral responses in mice and in guinea pigs and high levels of virus-specific effector T cells. The rP18tri-vector-induced antibody and T cell responses were significantly increased by a booster vaccination and were at high levels even after four applications, a unique feature of this live viral vector that is ideal for a prime-and-boost vaccination strategy. The vector can be given via various routes including intramuscular (IM), intraperitoneal (IP), intranasal (IN), and oral. Priming and boosting with different HA proteins from different influenza virus strains induced heterosubtypic immunity, thus there is potential to develop universal flu vaccines. Chemically inactivated rP18tri-P/H induced both humoral and CTL responses after a boost dose. The rP18tri vector induced protective immunity against virulent rP18 virus, thus there is the potential for developing cross-reactive vaccines against other pathogenic arenaviruses such as Lassa fever virus, and dual (triple) vaccines against combinations of other pathogens.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A genetically engineered Pichinde virus comprising: three separate ambisense genomic segments,
    wherein the first genomic segment comprises a coding region encoding a Z protein and a coding region encoding a L RNA-dependent RNA polymerase protein,
    wherein the second genomic segment comprises a coding region encoding a nucleoprotein (NP) and a first restriction enzyme site, and
    wherein the third genomic segment comprises a coding region encoding a glycoprotein and a second restriction enzyme site.

2. The virus of claim 1 wherein the second genomic segment comprises a multiple cloning site, and wherein the first restriction enzyme site is part of the multiple cloning site.

3. The virus of claim 1 wherein the third genomic segment comprises a multiple cloning site, and wherein the second restriction enzyme site is part of the multiple cloning site.

4. The virus of claim 1 wherein the second genomic segment further comprises a coding region encoding a first protein inserted at the first restriction site.

5. The virus of claim 1 wherein the third genomic segment further comprises a coding region encoding a second protein inserted at the first restriction site.

6. The virus of claim 1 wherein the second genomic segment further comprises a coding region encoding a first protein inserted at the first restriction site, and the third genomic segment further comprises a coding region encoding a second protein inserted at the first restriction site.

7. The virus of claim 6 wherein the first protein and the second protein are selected from an antigen and a detectable marker.

8. The virus of claim 7 wherein the antigen is a protein expressed by a viral pathogen, a prokaryotic pathogen, or a eukaryotic pathogen.

9. The virus of claim 6 wherein the first protein and the second protein are different.

10. The virus of claim 6 wherein the first protein and the second protein are the same.

11. The virus of claim 1 wherein the nucleoprotein comprises at least one mutation that reduces exoribonuclease activity of the nucleoprotein, wherein the mutation is a mutation of at least one RNase catalytic residue.

12. The virus of claim 11 wherein the at least one mutation is selected from the group consisting of an aspartic acid at amino acid 380 of SEQ ID NO:3, a glutamic acid at amino acid 382 of SEQ ID NO:3, an aspartic acid at amino acid 525 of SEQ ID NO:3, a histidine at amino acid 520 of SEQ ID NO:3, an aspartic acid at amino acid 457 of SEQ ID NO:3, or a combination thereof, wherein the aspartic acid, glutamic acid, or histidine is substituted with any other amino acid.

13. The virus of claim 1 wherein the glycoprotein comprises at least one mutation that alters the activity of the glycoprotein, wherein when the glycoprotein comprises SEQ ID NO:4 the mutation is selected from an asparagine at amino acid 20, an asparagine at amino acid 404, or a combination thereof, and wherein the asparagine is substituted with any other amino acid.

14. The genetically engineered Pichinde virus of claim 1 wherein the NP comprises an amino acid sequence having at least 80% identity to SEQ ID NO:3 and wherein any substitution is a conservative substitution.

15. The genetically engineered Pichinde virus of claim 1 wherein the NP comprises an amino acid sequence having at least 95% identity to SEQ ID NO:3.

16. An infectious virus particle comprising the three genomic segments of claim 1.

17. A composition comprising the infectious virus particle of claim 16, wherein the infectious virus particle is isolated.

18. A method for producing an immune response in a subject, comprising
administering to a subject the infectious virus particle of claim 16, wherein the second genomic segment further comprises a coding region encoding a first antigen inserted at the first restriction site, or the third genomic segment further comprises a coding region encoding a second antigen inserted at the first restriction site.

19. The method of claim 18 wherein the subject is a vertebrate.

20. The method of claim 19 wherein the vertebrate is a mammal.

21. The method of claim 20 wherein the mammalian is a human.

22. The method of claim 18 wherein the vertebrate is avian.

23. The method of claim 18 wherein the immune response comprises a humoral immune response.

24. The method of claim 18 wherein the immune response comprises a cell-mediated immune response.

25. The method of claim 18 wherein the first antigen or the second antigen is a protein expressed by a viral pathogen, a prokaryotic pathogen, or a eukaryotic pathogen, and wherein the subject is at risk of exposure to the viral pathogen, the prokaryotic pathogen, or the eukaryotic pathogen.

26. The method of claim 18 wherein the administering comprises administering at least two populations of infectious virus particles, wherein each population of infectious virus particle encodes a different antigen.

27. The method of claim 18, wherein the second genomic segment encodes the first antigen and the third genomic segment encodes the second antigen.

28. A collection of vectors comprising:
a first vector encoding a first genomic segment comprising a coding region encoding a Z protein and a coding region encoding a L RdRp protein, wherein the coding region encoding the Z protein is antigenomic,
a second vector encoding a second genomic segment comprising a coding region encoding a nucleoprotein (NP) and a first restriction enzyme site, wherein the coding region encoding the NP is antigenomic, and
a third vector encoding a third genomic segment comprises a coding region encoding a glycoprotein and a second restriction enzyme site, wherein the coding region encoding the glycoprotein is antigenomic.

29. The collection of claim 28 wherein the vectors are plasmids.

30. The collection of claim 28 wherein the plasmids further comprise a T7 promoter.

31. The collection of claim 28 wherein the second genomic segment comprises a multiple cloning site, and wherein the first restriction enzyme site is part of the multiple cloning site.

32. The collection of claim 28 wherein the third genomic segment comprises a multiple cloning site, and wherein the second restriction enzyme site is part of the multiple cloning site.

33. The collection of claim 28 wherein the second genomic segment further comprises a coding region encoding a first protein inserted at the first restriction site.

34. The collection of claim 28 wherein the third genomic segment further comprises a coding region encoding a second protein inserted at the first restriction site.

35. The collection of claim 28 wherein the second genomic segment further comprises a coding region encoding a first protein inserted at the first restriction site, and the third genomic segment further comprises a coding region encoding a second protein inserted at the first restriction site.

36. The collection of claim 35 wherein the first protein and the second protein are selected from an antigen and a detectable marker.

37. The collection of claim 36 wherein the antigen is a protein expressed by a viral pathogen, a prokaryotic pathogen, or a eukaryotic pathogen.

38. The collection of claim 35 wherein the first protein and the second protein are different.

39. The collection of claim 35 wherein the first protein and the second protein are the same.

40. The collection of vectors of claim 28 wherein the NP comprises an amino acid sequence having at least 80% identity to SEQ ID NO:3, and wherein any substitution is a conservative substitution.

41. The collection of vectors of claim 28 wherein the NP comprises an amino acid sequence having at least 95% identity to SEQ ID NO:3.

42. A method for making a genetically engineered Pichinde virus comprising:
introducing into a cell the collection of vectors of claim 28; and
incubating the cells in a medium wherein the first, second, and third genomic segments are expressed and packaged.

43. The method of claim 42 further comprising isolating an infectious virus particle from the medium.

44. The method of claim 42 wherein the cells express a T7 polymerase.

45. The isolated infectious virus particle of claim 42.

46. A composition comprising the isolated infectious virus particle of claim 45.

47. A method for using a reverse genetics system, comprising:
   introducing into a cell the three vectors of genomic segments of claim 42;
   incubating the cell wherein the three genomic segments are transcribed and the coding regions of each genomic segment are expressed.

48. The method of claim 47 further comprising isolating infectious virus particles produced by the cell, wherein each infectious virus particle comprises the three genomic segments.

49. The method of claim 47 wherein the introducing comprises transfecting a cell with the three genomic segments.

50. The method of claim 47 wherein the introducing comprises contacting the cell with an infectious virus particle comprising the three genomic segments.

51. The method of claim 47 wherein the cell is ex vivo.

52. The method of claim 47 wherein the cell is a vertebrate cell.

53. The method of claim 52 wherein the vertebrate cell is a mammalian cell.

54. The method of claim 53 wherein the mammalian cell is a human cell.

55. The method of claim 52 wherein the vertebrate cell is an avian cell.

56. The method of claim 55 wherein the avian cell is a chicken embryonic fibroblast.

57. A reverse genetics system for making a genetically engineered Pichinde virus comprising three vectors,
   wherein a first vector encodes a first genomic segment comprising a coding region encoding a Z protein and a coding region encoding a L RdRp protein, wherein the coding region encoding the Z protein is antigenomic,
   wherein the second vector encodes a second genomic segment comprising a coding region encoding a nucleoprotein (NP) and a first restriction enzyme site, wherein the coding region encoding the NP is antigenomic,
   wherein the third vector encodes a third genomic segment comprises a coding region encoding a glycoprotein and a second restriction enzyme site, wherein the coding region encoding the glycoprotein is antigenomic.

58. The reverse genetics system of claim 57 wherein each plasmid comprises a T7 promoter.

59. The reverse genetics system of claim 57 wherein the NP comprises an amino acid sequence having at least 80% identity to SEQ ID NO:3, and wherein any substitution is a conservative substitution.

60. The reverse genetics system of claim 57 wherein the NP comprises an amino acid sequence having at least 95% identity to SEQ ID NO:3.

* * * * *